US008093346B2

United States Patent
Suzuki et al.

(10) Patent No.: US 8,093,346 B2
(45) Date of Patent: Jan. 10, 2012

(54) METHOD FOR PRODUCING AN AMINOHYDROXYBENZOIC ACID-TYPE COMPOUND

(75) Inventors: Mototaka Suzuki, Kawasaki (JP);
Keiichi Yokoyama, Kawasaki (JP);
Yoshimi Kikuchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/983,500

(22) Filed: Jan. 3, 2011

(65) Prior Publication Data

US 2011/0137007 A1    Jun. 9, 2011

Related U.S. Application Data

(63) Continuation of application No. PCT/JP2009/062650, filed on Jul. 7, 2009.

(30) Foreign Application Priority Data

Jul. 9, 2008   (JP) .................................. 2008-178665

(51) Int. Cl.
*C08G 64/00* (2006.01)
*C08G 63/02* (2006.01)

(52) U.S. Cl. ........ 528/208; 435/183; 435/189; 435/190; 435/195

(58) Field of Classification Search .................. 435/183, 435/189, 190, 195; 528/208
See application file for complete search history.

(56) References Cited

U.S. PATENT DOCUMENTS

| 7,252,972 | B2 | 8/2007 | Kikuchi et al. |
| 7,704,707 | B2 | 4/2010 | Umezawa et al. |
| 7,723,081 | B1 | 5/2010 | Nakanishi et al. |
| 2004/0191875 | A1 | 9/2004 | Takeshita et al. |
| 2007/0184525 | A1 | 8/2007 | Date et al. |
| 2010/0143970 | A1 | 6/2010 | Yokoyama et al. |
| 2010/0159560 | A1 | 6/2010 | Umezawa et al. |
| 2010/0173368 | A1 | 7/2010 | Nakanishi et al. |

FOREIGN PATENT DOCUMENTS

| EP | 0 206 635 | 12/1986 |
| JP | 7-309946 | 11/1995 |
| JP | 8-11745 | 2/1996 |
| JP | 3354568 | 9/2002 |
| JP | 2003-159065 | 6/2003 |
| JP | 2004-261150 | 9/2004 |
| JP | 2004-283163 | 10/2004 |
| WO | WO91/01304 | 2/1991 |

OTHER PUBLICATIONS

Li, Y., et al., "Biosynthesis of 3-amino-4-hydroxybenzoic acid in *Streptomyces murayamaensis*: incorporation of [4-$^{13}$C]oxalacetate," Tetrahedron Letters 2000;41:5181-5185.
Suzuki, H., et al., "Novel Benzene Ring Biosynthesis from $C_3$ and $C_4$ Primary Metabolites by Two Enzymes," J. Biol. Chem. 2006;281(48):36944-36951.
International Search Report for PCT Patent App. No. PCT/JP2009/062650 (Sep. 1, 2009).
International Preliminary Report on Patentability for PCT Patent App. No. PCT/JP2009/062650 (Mar. 31, 2011).

*Primary Examiner* — Terressa Boykin
(74) *Attorney, Agent, or Firm* — Shelly Guest Cermak; Cermak Nakajima LLP

(57) ABSTRACT

Provided is a method for efficiently producing a 3-amino-4-hydroxybenzoic acid-type compound by culturing a coryneform bacterium that has a gene encoding a mutated aspartokinase not subject to feedback inhibition, and that is transformed with a recombinant vector containing a DNA encoding a protein having an activity to form 3-amino-4-hydroxybenzoic acid from dihydroxyacetone phosphate and aspartate semialdehyde.

9 Claims, 5 Drawing Sheets

```
                                        241                                                                      300
Translation of Ecoli DhnA      (241)  AENNGGYKAINYGYTDDRVYSKLTSEN-PIDLVRYQLANCYMGRAGLINSGGAAGGETDL
Translation of Bcep18194_C6861 Gril  (186)  SGDAASMADIAGSSLPVLVAGGAK-LPEDEFVAFTSRVMNAGALGIAAGRNVFAAPKAA
Translation of MJ0400 Gril     (188)  TGDIDSFRDWVKGPAPVVVAGGPKTNTDEEFLQMIKDAMEAGAAGVAVGRNIFQHDDVV
Translation of Francci3_2070 Gril  (184)  LGSTDELRDVVAASPIPTVAGGSSME-PEEYLAELAAAMRSGVGGVAIGRNVFQAPDPC
Translation of Francci3_4205 Gril  (185)  PGSVPALRDLTDACPVPLLCAGGPRRS-EDDVLAYVRDVLHGGAAGYAMGRSIFQADDPR
Translation of S.griseus Gril  (185)  VGSVAAMAEITAASPVPVVVGGPRDSDESRILAYVDDALRGGAAGVAMGRNVFQAPDPG
Translation of S.scabies Gril  (193)  ALPLERWSEVVAHSPIPVLAGGP---PDGSDLIFYGTAVMAAGCRGLAVGRNVFSSPST
                    Consensus  (241)  XGXVXAMRDIVAASPIPVVVAGGPKXXXEDDLLAYVXXXMXAGAAGYAMGRNVFQAPDPX
                                        301                                                 352
Translation of Ecoli DhnA      (300)  SDAVRTAVINKRAGGMGLILGRKAFKKSMADGVKLINAVQDVYLDSKITIA-
Translation of Bcep18194_C6861 Gril  (245)  PLIRRLSDAVIGVERRAAHLAA------------------------------
Translation of MJ0400 Gril     (248)  GITRAVCKIVIENADVEEALKEIRKK--------------------------
Translation of Francci3_2070 Gril  (243)  AMARRIAQIVHDPLEVARKQPRVQHSGAVG----------------------
Translation of Francci3_4205 Gril  (244)  RMAAVAQLVHAESEPRLEPTAEGQRSERKEAVLA------------------
Translation of S.griseus Gril  (245)  AMADKLSDLIHNSGTRGAARAPAGAAAGAA----------------------
Translation of S.scabies Gril  (251)  SLVSRLAAVHGTAGDGLPDGRGMSNQSSSSSRYSTIVAGVA-----------
                    Consensus  (301)  AMAXRLAXIVHXXAXXGXXXA
```

Ecoli DhnA: SEQ ID NO:21
Bcep18194_C6861 griI: SEQ ID NO:17
MJ0400 griI: SEQ ID NO:19
Francci3_2070 griI: SEQ ID NO:13
Francci3_4205 griI: SEQ ID NO:11
S.griseus griI: SEQ ID NO:9
S.scabies griI: SEQ ID NO:15
griI consensus sequence: SEQ ID NO:36

Figure 4:
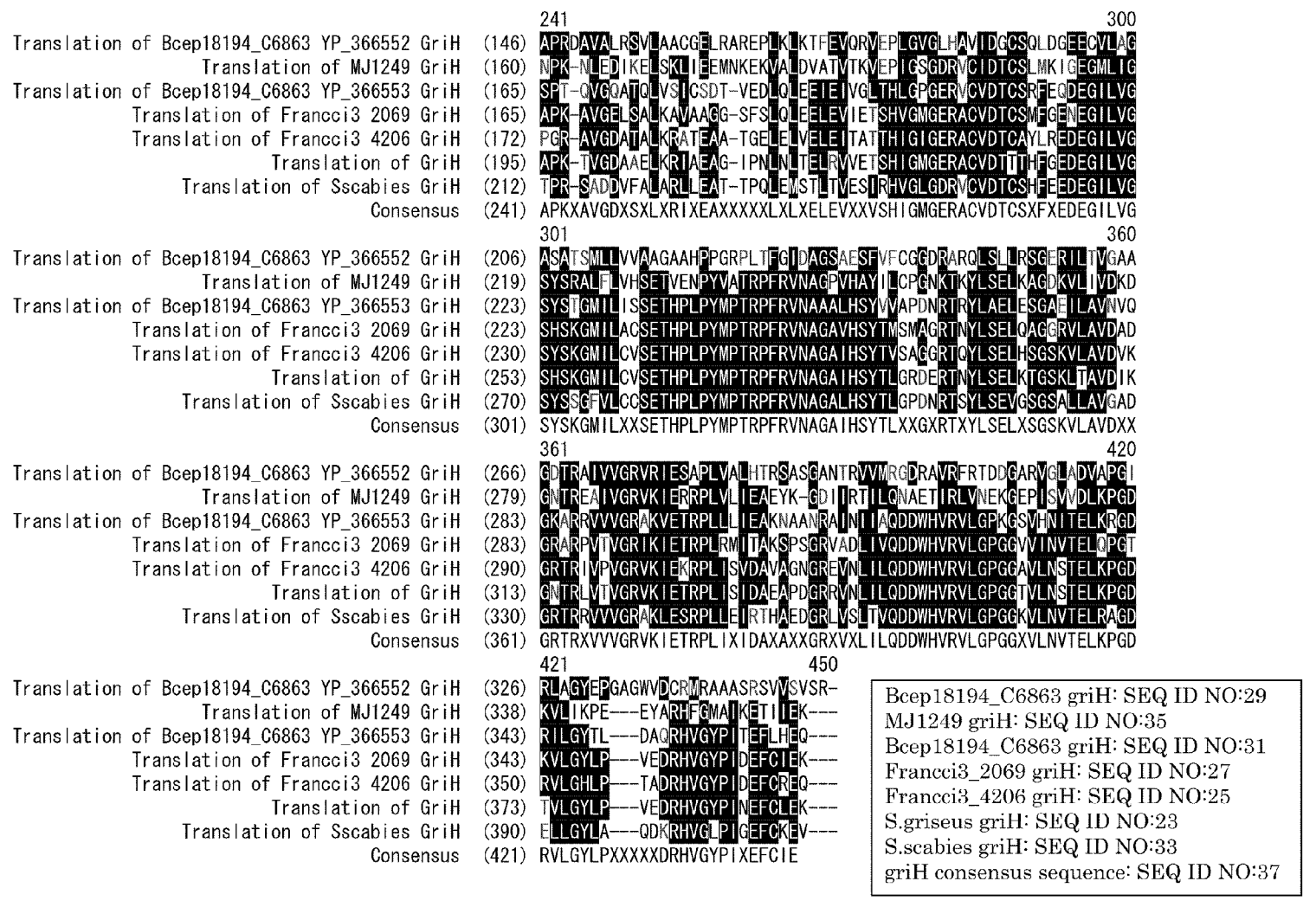

Figure showing multiple sequence alignment of GriH protein translations with consensus sequence, spanning residues 241-450.

Sequences shown:
- Bcep18194_C6863 griH: SEQ ID NO:29
- MJ1249 griH: SEQ ID NO:35
- Bcep18194_C6863 griH: SEQ ID NO:31
- Francci3_2069 griH: SEQ ID NO:27
- Francci3_4206 griH: SEQ ID NO:25
- S.griseus griH: SEQ ID NO:23
- S.scabies griH: SEQ ID NO:33
- griH consensus sequence: SEQ ID NO:37

US 8,093,346 B2

METHOD FOR PRODUCING AN AMINOHYDROXYBENZOIC ACID-TYPE COMPOUND

This application is a Continuation of, and claims priority under 35 U.S.C. §120 to, International Application No. PCT/JP2009/062650, filed Jul. 7, 2009, and claims priority therethrough under 35 U.S.C. §119 to Japanese Patent Application No. 2008-178665, filed on Jul. 9, 2008, the entireties of which are incorporated by reference herein. Also, the Sequence Listing in electronic format filed herewith is also hereby incorporated by reference in its entirety (File Name: 2010-12-29T_US-455_Seq_List; File Size: 156 KB; Date Created: Dec. 29, 2010).

FIELD OF THE INVENTION

The present invention relates to a method for producing an aminohydroxybenzoic acid-type compound. More particularly, the present invention relates to a method for conveniently and inexpensively producing an aminohydroxybenzoic acid-type compound, which is useful as an intermediate in the production of dyes, agricultural chemicals, pharmaceuticals and other synthetic organic compounds, and is also useful as a monomer of the high performance heat resistant polymer polybenzoxazole. Specifically, the present invention provides a method for producing a 3-amino-4-hydroxybenzoic acid-type compound using a coryneform bacterium having an enzymatic activity to form a 3-amino-4-hydroxybenzoic acid-type compound using dihydroxyacetone phosphate and aspartate semialdehyde as substrates.

The present invention further relates to a method for producing a polybenzoxazole polymer from an aminohydroxybenzoic acid-type compound.

BRIEF DESCRIPTION OF THE RELATED ART

Conventional methods for producing an aminohydroxybenzoic acid-type compound are known. Such compounds are useful as intermediates in the manufacturing of dyes, agricultural chemicals, pharmaceuticals and other synthetic organic compounds. When the aminohydroxybenzoic acid-type compound is a 3-amino-4-hydroxybenzoic acid-type compound, which is a monomer of polybenzoxazole, a method is known in which a raw material of 4-hydroxybenzoic acid or an ester thereof is nitrated with nitric acid to make 3-nitro-4-hydroxybenzoic acid or a derivative thereof, and subsequently the nitro group of this intermediate is reduced with a reducing agent such as palladium carbon to isolate a phosphate salt (see U.S. Pat. No. 3,354,568). In addition, when 4-halobenzoic acid or an ester thereof is used as the raw material, a method is known in which it is nitrated with nitric acid to obtain 3-nitro-4-chlorobenzoic acid, and subsequently the halo group is treated with alkali metal hydroxide to make 3-nitro-4-hydroxybenzoic acid, which is then reduced (see JP 8-11745).

However, in these methods, the reactions for isolation, purification, and the like require several steps in order to avoid production of a poly-nitrated chemical, which is hazardous in nature, and enhance purity of the product, resulting in higher costs. In addition, another problem is that the yield is greatly decreased due to the production of isomers.

It has been reported that the presence of impurities in a product of an aminohydroxybenzoic acid-type compound prevents polymer formation.

Polybenzoxazoles are well-known as rigid polymers having high strength, and can be used for films for print wiring plates and protection films for semiconductor elements. However, conventional methods for producing polybenzoxazole using a chemical catalyst include an extreme reaction using an unsafe catalyst. No method for inexpensively producing a monomer precursor with high purity is available. Thus, practical application of these polymers has been delayed.

Various chemical synthesis methods have been reported for 3-amino-4-hydroxybenzoic acid. However, these methods are unsuitable for production because multiple steps of the reactions are required and the cost becomes high.

Generally, the production of a substance by biosynthesis has several advantages compared with chemical synthesis. For example, an inexpensive and regenerable raw material can be used and the biosynthesis can be performed under mild reaction conditions.

A method for producing an aminohydroxybenzoic acid-type compound utilizing a biosynthetic reaction in a microorganism has been reported. For example, it has been reported that *Actinomycetes* biosynthesizes 3-amino-4-hydroxybenzoic acid (see Yongfu Li et al., Tetrahedron Letters, 41, p5181-5185 (2000)). However, this 3-amino-4-hydroxybenzoic acid is unstable in weakly acidic conditions to around alkaline conditions, thus it is easily oxidized and dimerized in culture medium, and the yield decreases. It has been also reported that 2-amino-3-hydroxybenzoic acid (3-hydroxyanthranilic acid) can be obtained by cultivation of *Actinomycetes* (e.g., see JP Hei-7-309946-A). In this case, 2-amino-3-hydroxybenzoic acid is not directly produced by the cultivation, but 2,3-dihydroxy-3-anthranilic acid is obtained by the cultivation, and then this is dehydrogenated by palladium carbon catalyst to produce 2-amino-3-hydroxybenzoic acid. The palladium carbon catalyst is expensive, and a large amount of the catalyst is required to efficiently perform the reaction. Thus, this method is not industrially practical.

Recently, a gene involved in the biosynthesis of 3-amino-4-hydroxybenzoic acid was found in *Actinomycetes*, and its biosynthetic pathway was elucidated. Specifically, it has been elucidated that 3-amino-4-hydroxybenzoic acid is biosynthesized via two steps with GriI, which catalyzes a carbon-carbon binding reaction between a C4 compound having an amino group and a C3 or C4 compound using dihydroxyacetone phosphate and aspartate semialdehyde as substrates, and with GriH, which catalyzes cyclization of a C7 compound or cyclization of a C8 compound with decarboxylation (J. Biol. Chem., 281, 48, 36944-36951, 2006). It has been also reported that when *Streptomyces lividans*, which is an *Actinomycetes*, was transformed with a recombinant vector containing a griI gene and a griH gene, 3-amino-4-hydroxybenzoic acid is produced (see JP 2004-283163-A). However, regardless of studies on the compositions of production media and cultivation methods, its maximum productivity is 5 g/L of medium, and there are still many problems for practical production. The 3-amino-4-hydroxybenzoic acid product is a mixture with an acetylated form produced in the biosynthesis process, and deacetylation is unavoidable. Because of these issues, an efficient production process using biosynthesis has not been established.

SUMMARY OF THE INVENTION

It is an aspect of the present invention to provide a method for producing aminohydroxybenzoic acid-type compounds such as 3-amino-4-hydroxybenzoic acid conveniently and inexpensively.

A method is described for producing non-acetylated 3-amino-4-hydroxybenzoic acid in a large amount by culturing a coryneform bacterium that has a gene encoding a mutated aspartokinase in which feedback inhibition is suppressed, and that is transformed with a recombinant vector incorporating a griI gene and a griH gene.

It is an aspect of the present invention to provide a method for producing a 3-amino-4-hydroxybenzoic acid-type compound, comprising culturing a coryneform bacterium comprising a gene encoding a aspartokinase which is not subject to feedback inhibition, and a recombinant vector comprising a DNA encoding a protein having an activity to form 3-amino-4-hydroxybenzoic acid from dihydroxyacetone phosphate and aspartate semialdehyde.

It is an aspect of the present invention to provide the method as described above, wherein expression of a gene encoding said aspartokinase is enhanced.

It is an aspect of the present invention to provide the method as described above, wherein expression of a pyruvate carboxylase gene is enhanced.

It is an aspect of the present invention to provide the method as described above, wherein said DNA comprises a griI gene and a griH gene.

It is an aspect of the present invention to provide the method as described above, wherein said griI gene and griH gene are derived from *Actinomycetes*.

It is an aspect of the present invention to provide the method as described above, wherein said coryneform bacterium is *Corynebacterium glutamicum*.

It is a further aspect of the present invention to provide a method for producing a polybenzoxazole polymer, comprising polymerizing a 3-amino-4-hydroxybenzoic acid-type compound produced by a method as described above.

BRIEF DESCRIPTION OF DRAWINGS

FIG. 1 is a view showing griI gene homologs and a consensus sequence.

FIG. 2 is a view showing the alignments of the griI gene homologs and the consensus sequence (continued).

FIG. 3 is a view showing alignments of griH gene homologs and a consensus sequence.

FIG. 4 is a view showing the alignments of the griH gene homologs and the consensus sequence (continued).

DESCRIPTION OF THE PREFERRED EMBODIMENTS

Figure 5:
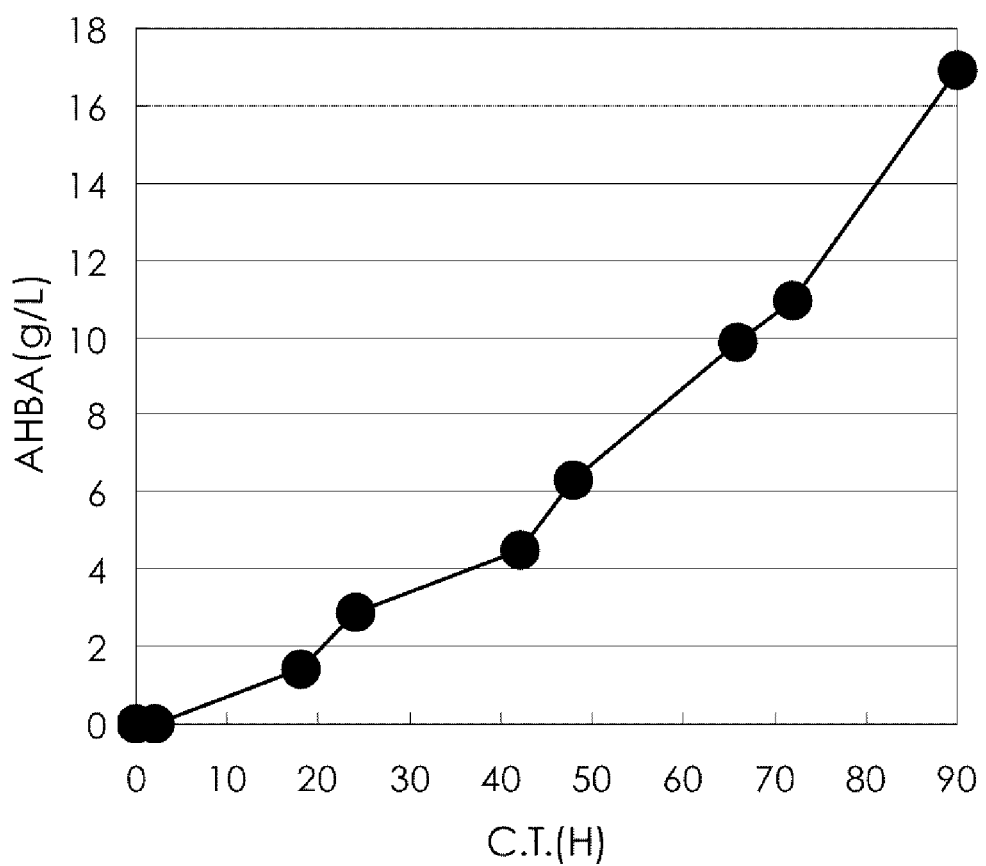
FIG. 5 is a view showing the production of 3-amino-4-hydroxybenzoic acid by *Corynebacterium glutamicum*.

Hereinafter, the present invention will be described in detail.

The present invention relates to a method for producing a 3-amino-4-hydroxybenzoic acid-type compound by culturing a coryneform bacterium transformed with a recombinant vector which contains a DNA encoding a protein having an activity to form 3-amino-4-hydroxybenzoic acid from dihydroxyacetone phosphate and aspartate semialdehyde.

The 3-amino-4-hydroxybenzoic acid-type compound can include 3-amino-4-hydroxybenzoic acid (hereinafter sometimes abbreviated as "3,4-AHBA") having the following structure, and derivatives thereof and salts thereof.

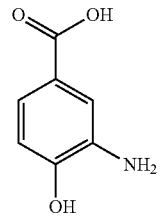

The derivatives can include, for example, 3-amino-4-hydroxybenzaldehyde obtained by aldehydizing a carboxyl group in 3-amino-4-hydroxybenzoic acid, and the like. The salts includes basic salts of carboxylic acid such as alkali metal (sodium, potassium and lithium) salts and alkali earth metal (calcium and magnesium) salts, and acid addition salts such as hydrochloride salts, sulfate salts, nitrate salts, and phosphate salts.

<1> DNA Encoding Protein Having Activity to Form 3-amino-4-hydroxybenzoic Acid-Type Compound DNA can include a gene involved in biosynthesis of the 3-amino-4-hydroxybenzoic acid-type compound. In other words, the DNA includes a gene having a function of recovering, imparting, promoting, or regulating the biosynthesis of the 3-amino-4-hydroxybenzoic acid-type compound.

Specifically, the DNA can include a DNA encoding a protein having an activity to form a 3-amino-4-hydroxybenzoic acid-type compound from dihydroxyacetone phosphate and aspartate semialdehyde (hereinafter sometimes also referred to as a "3,4-AHBA forming activity"). The DNA includes a gene encoding a protein having an enzymatic activity to catalyze carbon-carbon bond formation between dihydroxyacetone phosphate and aspartate semialdehyde, and a gene encoding a protein having an enzymatic activity to catalyze cyclization of a C7 compound obtained by forming the carbon-carbon bond between dihydroxyacetone phosphate and aspartate semialdehyde (see JP 2004-283163-A). Hereinafter, both enzyme activities are sometimes collectively referred to as the 3,4-AHBA biosynthesis ability.

The gene encoding a protein which has an enzymatic activity to catalyze the carbon-carbon bond formation between dihydroxyacetone phosphate and aspartate semialdehyde can include the griI gene (SEQ ID NOS:8 and 9) derived from *Streptomyces griseus*, and griI gene homologs. A griI gene homolog can refer to a gene which is derived from another microorganism, has high homology to the above gene derived from *Streptomyces griseus*, and encodes a protein having the same enzymatic activity. Such a gene with high homology can be elucidated by performing a Blast search using the sequences of SEQ ID NOS:8 and 9. For example, the gene can include a fructose-bisphosphate aldolase gene derived from *Frankia* sp. (Accession no. YP_483282, SEQ ID NOS: 10 and 11), a fructose-bisphosphate aldolase gene derived from *Frankia* sp. (Accession no. YP_481172, SEQ ID NOS:12 and 13), a fructose-bisphosphate aldolase gene derived from *Streptomyces scabies* (http://www.sanger.ac.uk/cgi-bin/blast/submitblast/s_scabies, SEQ ID NOS:14 and 15), a fructose-bisphosphate aldolase gene derived from *Burkholderia* sp 383 (Accession no. Q39NQ9, SEQ ID NOS:16 and 17), a fructose-bisphosphate aldolase gene derived from *Methanococcus jannaschii* (Accession no. NP_247374, SEQ ID NOS:18 and 19), and a dhnA gene derived from *Escherichia coli* (Accession no. NC_000913, SEQ ID NOS:20 and 21) (Journal of Biochemistry vol. 281, NO. 48, pp. 36944-36951, supplementary data).

The gene encoding the protein having the enzymatic activity to catalyze the cyclization of the C7 compound obtained by forming the carbon-carbon bond between dihydroxyacetone phosphate and aspartate semialdehyde can include the griH gene (SEQ ID NOS:22 and 23) derived from *Streptomyces griseus* and griH gene homologs. A griH gene homolog can refer to a gene which is derived from the another microorganism, has high homology to the above gene derived from *Streptomyces griseus*, and encodes a protein having the same enzymatic activity. Such a gene with high homology can be elucidated by performing a Blast search using the sequences of SEQ ID NOS:22 and 23. For example, the gene may include a 3-dehydroquinate synthase gene derived from *Frankia* sp. (Accession no. YP_483283, SEQ ID NOS:24 and 25), a 3-dehydroquinate synthase gene derived from *Frankia* sp. (Accession no. YP_481171, SEQ ID NOS:26 and 27), a 3-dehydroquinate synthase gene derived from *Burkholderia* sp. (Accession no. YP_366552, SEQ ID NOS: 28 and 29), a 3-dehydroquinate synthase gene derived from *Burkholderia* sp. (Accession no, YP_366553, SEQ ID NOS: 30 and 31), a 3-dehydroquinate synthase gene derived from *Streptomyces scabies* (<http://www.sanger.ac.uk/cgi-bin/blast/submitblast/s_scabies>, SEQ ID NOS:32 and 33), and a 3-dehydroquinate synthase gene derived from *Methanococcus jannaschii* (Accession no. NP_248244, SEQ ID NOS:34 and 35) (Journal of Biochemistry vol. 281, NO. 48, pp. 36944-36951, supplementary data).

In addition, the griI gene homolog can include those having 90% or more, 95% or more, 98% or more, and even 99% or more homology to the amino acid sequences of SEQ ID NOs: 9, 11, 13, 15, 17, 19 or 21 and encoding a protein having the aforementioned enzymatic activity. The griH gene homolog can include those having 90% or more, 95% or more, 98% or even 99% or more homology to the amino acid sequences of SEQ ID NOs: 23, 25, 27, 29, 31, 33 or 35 and encoding a protein having the aforementioned enzymatic activity. The homology of the amino acid sequences and nucleotide sequences can be determined using, for example, algorithm BLAST by Karlin and Altschul (Pro. Natl. Acad. Sci. USA, 90, 5873 (1993)) or FASTA (Methods Enzymol., 183, 63 (1990)). Programs referred to as BLASTIN and BLASTX have been developed based on this algorithm BLAST (see <http://www.ncbi.nlm.nih.govbi.nlm.nih.gov>).

Figure 1:
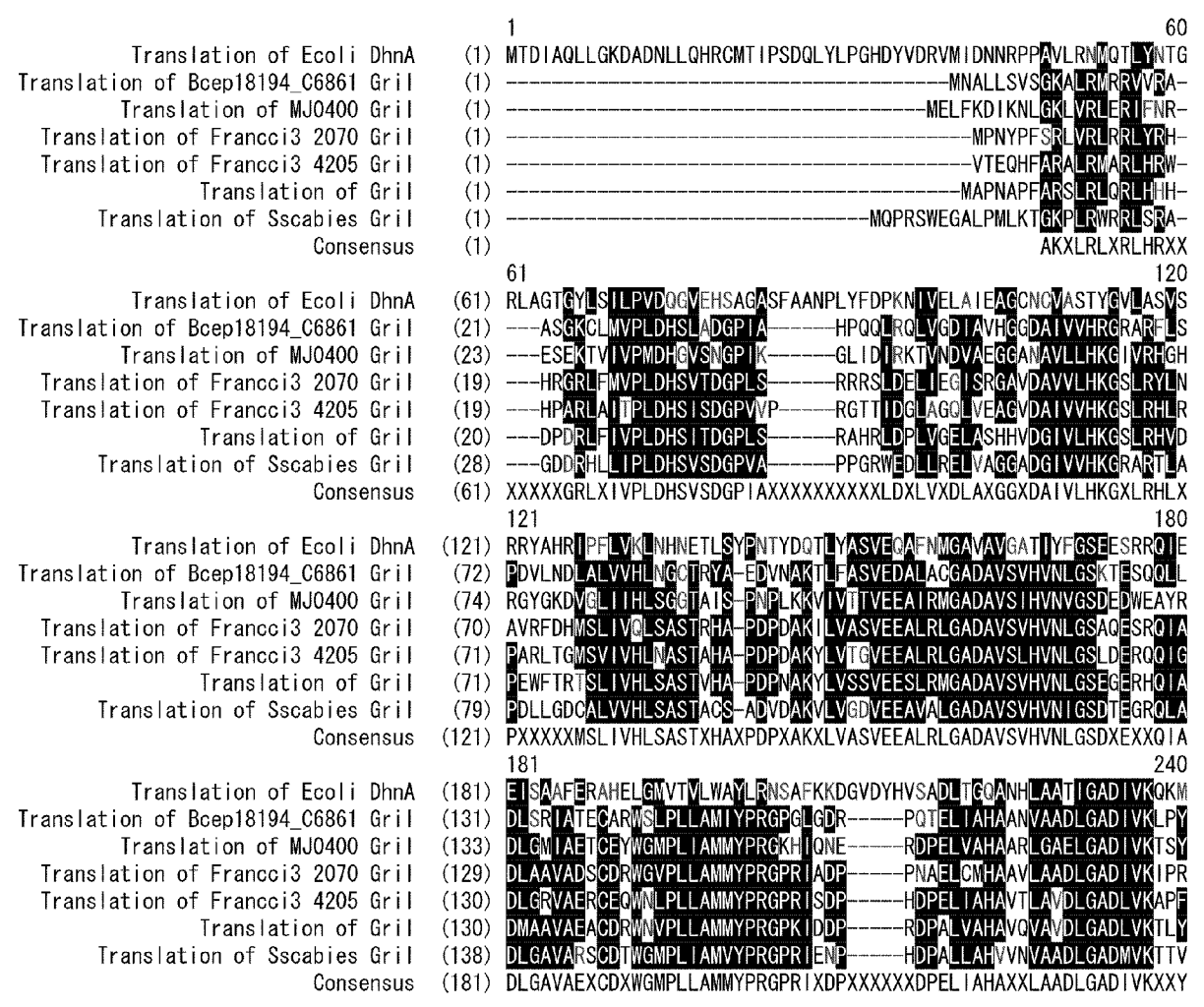
Figure 3:
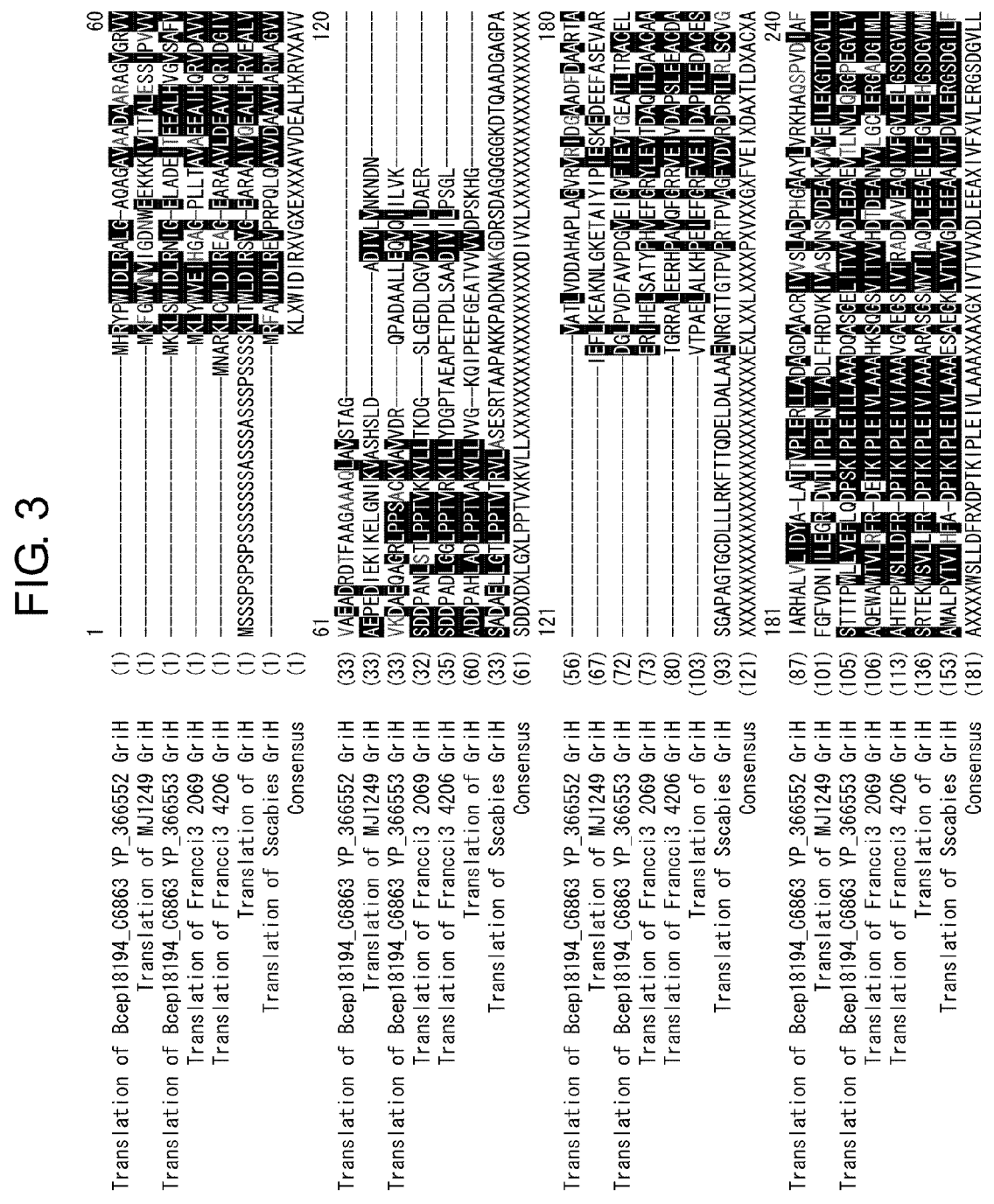

Alignments of the amino acid sequences of SEQ ID NOs: 9, 11, 13, 15, 17, 19 and 21 are shown in FIGS. 1 and 2, and the alignments of the amino acid sequences of SEQ ID NOs: 23, 25, 27, 29, 31, 33 and 35 are shown in FIGS. 3 and 4. In addition, their consensus sequences are shown in SEQ ID NOS: 36 and 37. The above griI gene homologs include a gene encoding the amino acid sequence of SEQ ID NO: 36, and the griH gene homologs include a gene encoding the amino acid sequence of SEQ ID NO: 37.

Several sequences of the griI gene and the griH gene have been already revealed as mentioned above, and thus the griI gene and the griH gene can be obtained using primers made based on their nucleotide sequences. For example, coding regions of griI and griH derived from *Streptomyces griseus* and their flanking regions including their regulatory regions can be obtained simultaneously by the PCR method (PCR: polymerase chain reaction; see White, T. J. et al., Trends Genet. 5, 185 (1989)) with chromosomal DNA from *Streptomyces griseus* as a template using the primers shown in SEQ ID NOs:1 and 2. Specific examples of *Streptomyces griseus* include the IFO13350 (NRBC13350) strain. This strain is available from Biological Resource Center, National Institute of Technology and Evaluation (http://www.nbrc.nite.go.jp/e/gene-e.html). The homologs of griI or griH derived from other microorganisms can be obtained likewise.

There can be differences in the nucleotide sequences of the griI genes or the griH genes depending on species and strains of the microorganisms. Thus, the griI and the griH genes used for obtaining the coryneform bacterium are not limited to the genes encoding the amino acid sequences of SEQ ID NOs: 9, 11, 13, 15, 17, 19 or 21 and SEQ ID NOs: 23, 25, 27, 29, 31, 33 or 35, respectively. As long as the genes can improve the ability to produce 3,4-AHBA in the coryneform bacterium by co-expressing the genes and augmenting the expression of the genes in the coryneform bacterium, the genes may be mutated genes or artificially modified genes encoding proteins having sequences containing substitution, deletion, insertion or addition of one or several amino acids at one or multiple positions in the amino acid sequences of SEQ ID NOs: 9, 11, 13, 15, 17, 19 or 21 and SEQ ID NOs: 23, 25, 27, 29, 31, 33 or 35, respectively. The "several amino acids" can vary depending on the positions and the kinds of amino acid residues in the three dimensional structure of the protein, and can be 1 to 50, 1 to 20, 1 to 10, and even 1 to 5 amino acids. Such substitution, deletion, insertion, addition, or inversion can include naturally occurring mutants or variants, e.g., those which occur based on individual differences or species differences of the microorganism which carries the griI gene or the griH gene.

The above substitution can be a conservative substitution which is a neutral mutation and in which no functional change occurs. The conservative substitution includes substitution between Phe, Trp and Try when the amino acid to be substituted is an aromatic amino acid, a substitution between Leu, Ile and Val when the amino acid to be substituted is a hydrophobic amino acid, a substitution between Gln and Asn when the amino acid to be substituted is a polar amino acid, a substitution between Lys, Arg and His when the amino acid to be substituted is a basic amino acid, a substitution between Asp and Glu when the amino acid to be substituted is an acidic amino acid, or a substitution between Ser and Thr when the amino acid to be substituted is an amino acid having a hydroxyl group. More specifically, the conservative substitution can include a substitution from Ala to Ser or Thr, a substitution from Arg to Gln, His or Lys, a substitution from Asn to Glu, Gln, Lys, His or Asp, a substitution from Asp to Asn, Glu or Gln, a substitution from Cys to Ser or Ala, a substitution from Gln to Asn, Glu, Lys, His, Asp or Arg, a substitution from Glu to Gly, Asn, Gln, Lys or Asp, the substitution from Gly to Pro, a substitution from His to Asn, Lys, Gln, Arg or Tyr, a substitution from Ile to Leu, Met, Val or Phe, a substitution from Lys to Asn, Glu, Gln, His or Arg, a substitution from Met to Ile, Leu, Val or Phe, a substitution from Phe to Trp, Tyr, Met, Ile or Leu, a substitution from Ser to Thr or Ala, a substitution from Thr to Ser or Ala, a substitution from Trp to Phe or Tyr, a substitution from Tyr to His, Phe or Trp, and a substitution from Val to Met, Ile or Leu.

Furthermore, codons may be substituted so as to be easily utilized in the host into which the griI gene and the griH gene are introduced since the degeneracy of the genetic code can be different depending on the chosen host. Likewise, as long as the griI gene and the griH gene function to improve production of 3,4-AHBA in a coryneform bacterium by enhancing the expression of both genes, these genes can encode a protein which is extended or deleted at either the N terminal or C terminal side. For example, the length of amino acid residues to be extended or deleted can be 50 amino acids or less, 20 or less, 10 or less, and even 5 or less. More specifically, the griI gene and the griH gene can encode proteins in which 50 to 5 amino acids from the N terminal side or 50 to 5 amino acids from the C terminal side is extended or deleted.

Such genes homologous to the griI gene and the griH gene can be obtained by modifying the genes encoding the amino acid sequences of SEQ ID NOs: 9, 11, 13, 15, 17, 19 or 21 and SEQ ID NOs: 23, 25, 27, 29, 31, 33 or 35 so that an amino acid residue at a particular position of the encoded protein is substituted, deleted, inserted or the added by site-specific mutagenesis. The homologous gene can also be obtained by conventionally known mutation treatments. The mutation treatment can include by treating the griI gene or the griH gene with hydroxylamine and the like in vitro, or treating the microorganism carrying the gene, e.g., the coryneform bacterium, with a mutagen such as an ultraviolet ray, N-methyl-N'-nitro-N-nitrosoguanidine (NTG) or ethyl methanesulfonate (EMS) typically used for mutation treatments. Furthermore, the gene encoding the enzyme with high activity can also be obtained by artificially introducing a mutation into the griI gene or the griH gene by gene recombination using error prone PCR (Cadwell, R. C. PCR Meth. Appl. 2, 28 (1992)), DNA shuffling (Stemmer, W. P. Nature 370, 389 (1994)), or StEP-PCR (Zhao, H. Nature Biotechnol. 16, 258 (1998)).

The griI gene and the griH gene can also include DNAs which hybridize under stringent conditions with nucleotide sequences complementary to the nucleotide sequences of SEQ ID Nos: 8, 10, 12, 14, 16, 18 or 20 and SEQ ID NOs: 22, 24, 26, 28, 30, 32 or 34, or probes which can be prepared from these sequences, and the DNAs encode proteins which function to improve the ability to biosynthesize 3,4-AHBA in a coryneform bacterium by expressing both genes. Here, the expression "stringent conditions" can refer to conditions wherein a so-called specific hybrid is formed and non-specific hybrids are not formed. By way of example, an example includes conditions where a pair of DNAs with high homology, e.g., DNAs having homology of 80% or more, 90% or more, 95% or even 97% or more are hybridized, whereas DNAs with lower homology than that are not hybridized, or conditions of washing once, or even twice to three times under washing conditions of an ordinary Southern hybridization, i.e., hybridization at salt concentrations equivalent to 1×SSC and 0.1% SDS at 60° C., 0.1×SSC and 0.1% SDS at 60° C., or even 0.1×SSC and 0.1 SDS at 68° C.

As the probe, it is possible to use partial sequences of the nucleotide sequence complementary to the nucleotide sequences of SEQ ID Nos: 8, 10, 12, 14, 16, 18 or 20, or SEQ ID NOs: 22, 24, 26, 28, 30, 32 or 34. Such a probe can be made by PCR with a DNA fragment containing this sequence as the template using oligonucleotides made based on these nucleotide sequences as the primers. For example, when the DNA fragment of about 300 bp in length is used as the probe, the washing conditions for the hybridization can include 2×SSC and 0.1% SDS at 50° C.

The description concerning the above gene homologs and the conservative mutation can be likewise applied to the other genes described herein.

Whether these griI and griH homologous genes encode the proteins which improve the ability to produce 3,4-AHBA or not can be confirmed by introducing these genes into the coryneform bacterium, e.g., C. glutamicum AJ110135 strain (see JP 2004-261150-A), having the gene encoding a mutated aspartokinase in which feedback inhibition is suppressed, and examining whether the activity to form 3,4-AHBA is improved or not. In that case, the effect can be clearly verified by quantifying 3,4-AHBA using reverse phase chromatography according to Suzuki et al's method (J. Bio. Chem., 281, 823-833 (2006)).

<2> Recombinant Vector

A recombinant vector can be obtained by introducing a DNA in accordance with the presently disclosed subject matter into a plasmid, which is an expression vector. The griI and griH genes can be on separate recombinant vectors, or can be linked via an appropriate spacer and on the same recombinant vector as long as they are able to be expressed in the chosen host. The griI and griH genes can be derived from the same microorganism, or they can be derived from different microorganisms. When the griI and griH genes are derived from the same microorganism and are located close together on the chromosome, a portion of DNA containing both the griI and griH genes can be cut out and carried in the vector.

The recombinant vector can generally have a promoter, the aforementioned DNA, e.g., griI and griH, and regulatory regions (operator and terminator) required for expressing the genes in the coryneform bacterium in appropriate positions so that they are functional.

The expression vector which can be used as the recombinant vector is not particularly limited and may be a vector which can function in the coryneform bacterium. It may replicate independently outside of the chromosome like a plasmid, or it may be integrated into the bacterial chromosome. Plasmids derived from the coryneform bacterium can be used, and include, for example, pHM1519 (Agric, Biol. Chem., 48, 2901-2903 (1984), pAM330 (Agric, Biol. Chem., 48, 2901-2903 (1984)), and plasmids having a drug resistant gene.

The promoter is not particularly limited, and a promoter which can function in a microbial cell of the coryneform bacterium can be generally used. The promoter may be derived from other species, e.g., a promoter derived from *Escherichia coli*, such as a tac promoter.

The promoter derived from a coryneform bacterium includes promoters of the genes encoding cell surface layer proteins PS1, PS2, and SlpA, and promoters of genes in biosynthetic systems of various amino acids.

<3> Transformant

The coryneform bacterium is not particularly limited as long as the coryneform bacterium has the gene encoding the mutated aspartokinase which is not subject to feedback inhibition. Also, the ability to produce 3-amino-4-hydroxybenzoic acid is imparted by transforming the chosen coryneform bacterium with a recombinant vector incorporating DNA encoding a protein having the activity to form a 3-amino-4-hydroxybenzoic acid-type compound from dihydroxyacetone phosphate and aspartate semialdehyde. The coryneform bacterium which can be a parent strain can include bacteria which were conventionally classified into genus *Brevibacterium*, but are currently integrated into genus *Corynebacterium* (Int. J. Syst. Bacteriol., 41, 255 (1991)), and bacteria belonging to genus *Brevibacterium*, which is very closely related to genus *Corynebacterium*. Specifically, the following are exemplified.

*Corynebacterium acetoacidfilum*
*Corynebacterium acetoglutamicum*
*Corynebacterium alkanoliticum*
*Corynebacterium callunae*
*Corynebacterium glutamicum*
*Corynebacterium lilium* (*Corynebacterium glutamicum*)
*Corynebacterium melasecola*
*Corynebacterium themoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*

*Brevibacterium lactofermentum* (*Corynebacterium glutamicum*)

*Brevibacterium roseum*
*Brevibacterium saccharoliticum*
*Brevibacterium thiogenitalis*
*Brevibacterium album*
*Brevibacterium selinum* and
*Microbacterium ammoniafilum*

The coryneform bacterium which can act as the parent strain can efficiently supply dihydroxyacetone phosphate and aspartate semialdehyde, which are the substrates in the biosynthesis of a 3-amino-4-hydroxybenzoic acid-type compound. In the native state, aspartokinase in the coryneform bacterium undergoes cooperative feedback inhibition by lysine and threonine, but a coryneform bacterium in which the aspartokinase gene is mutated so that the feedback inhibition is suppressed can be used.

Native aspartokinase in the coryneform bacterium is a heteroprotein composed of an α-subunit and a β-subunit, and coding regions of the α-subunit and the β-subunit are partially overlapping. The sequence of the native, or wild-type, aspartokinase α-subunit derived from *Corynebacterium glutamicum* (*Brevibacterium lactofermentum*) ATCC13869 is shown in SEQ ID NO: 38. The suppression of the feedback inhibition to the aspartokinase is accomplished by introducing a mutation so that an alanine residue at position 279 from the N terminus is substituted with a threonine residue, or a threonine residue at position 311 from the N terminus is substituted with an isoleucine residue, or a serine residue at position 301 from the N terminus is substituted with a tyrosine residue, or a threonine residue at position 380 from the N terminus is substituted with an isoleucine residue, or a threonine residue at position 308 is substituted with an isoleucine residue, or an arginine residue at position 320 from the N terminus is substituted with a glycine residue, or a glycine residue at position 345 is substituted with an aspartic acid residue (WO94/25605 Publication Pamphlet, WO00/63388 Publication Pamphlet, U.S. Pat. No. 6,844,176, WO01/049854 Publication Pamphlet and the like). Even allelic variants of wild-type aspartokinase can exist, in which several amino acid residues are different from the sequence shown in SEQ ID NO: 38 depending on the strain of the coryneform bacterium from which the aspartokinase is derived. The definitions of such mutations are the same as those described for the aforementioned griI and griH. Sites to be modified for the cancellation of the feedback inhibition can be identified by performing a sequence alignment publicly known for those skilled in the art. A modification for the suppression of the feedback inhibition to the aspartokinase can be accomplished by publicly known methods for those skilled in the art, e.g., acquisition of a mutant strain having resistance to a lysine analog such as 2-aminoethylcysteine and the site specific mutagenesis by gene substitution utilizing homologous recombination. A coryneform bacterium having an enhanced activity of the mutated aspartokinase in which the feedback inhibition is suppressed can be obtained by transforming the coryneform bacterium with the plasmid containing the gene encoding the mutated aspartokinase in which the feedback inhibition is suppressed. In the Examples, *Corynebacterium glutamicum* AJ110135 strain (JP 2004-261150-A) having an aspartokinase in which the feedback inhibition is suppressed by substituting the alanine residue at position 279 from the N terminus with the threonine residue in aspartokinase was used. The lysI gene is deleted in the AJ110135 strain, which is the gene encoding a lysine permease.

The coryneform bacterium having the mutated aspartokinase in which the feedback inhibition is suppressed may be the coryneform bacterium in which the expression of a pyruvate carboxylase gene is enhanced additionally.

Any of the coryneform bacteria which act as the parent strain can be used as long as the bacterial strain can efficiently supply dihydroxyacetone phosphate and aspartate semialdehyde.

The transformation of the coryneform bacterium using the recombinant vector incorporating the DNA encoding the protein having the activity to form 3-amino-4-hydroxybenzoic acid from dihydroxyacetone phosphate and aspartate semialdehyde can be carried out according to methods publicly known in the art. For example, a protoplast method (Gene, 39, 281-286 (1985)), an electroporation method (Bio/Technology, 7, 1067-1070 (1989)) and the like can be used. When the transformation for cancelling the feedback inhibition to aspartokinase is performed, either the transformation for imparting the activity to form 3,4-AHBA or the transformation for cancelling the feedback inhibition to aspartokinase may be performed in advance.

<4> Method for Producing a 3-Amino-4-Hydroxybenzoic Acid-Type Compound

The 3-amino-4-hydroxybenzoic acid-type compound can be produced by culturing the transformant of the coryneform bacterium obtained above and recovering the 3-amino-4-hydroxybenzoic acid-type compound which is produced in the medium.

The medium for culturing the transformant is not particularly limited as long as the host cell grows, and the transformant can be cultured according to methods publicly known in the art. For example, the transformant can be cultured in an ordinary medium containing a carbon source, a nitrogen source, and inorganic ions. Organic trace nutrients such as vitamins and amino acids may be added if necessary in order to obtain higher proliferation. A cultivation temperature is typically 25 to 34° C., and it is desirable to control pH to 6.5 to 7.5. A cultivation time period is typically 20 to 90 hours.

It is desirable to perform the cultivation of the transformant under controlled supply of oxygen. Specifically, it is desirable to keep oxygen at 2.0 ppm or less when bacterial growth enters the logarithmic growth phase.

The recovery method used to recover and purify the 3-amino-4-hydroxybenzoic acid-type compound from the culture medium can be appropriately selected from publicly known methods. For example, a culture medium supernatant can be recovered by removing microbial cells by centrifugation or membrane filtration after adjusting pH of the culture medium to an acidic pH at which solubility of the 3-amino-4-hydroxybenzoic acid-type compound is high. The recovery method of 3-amino-4-hydroxybenzoic acid from the culture medium supernatant in which the microbial cells have been removed may include purification by a porous adsorbent, crystallization and precipitation.

The porous adsorbent can be a porous solid adsorbent having a large surface area, and specifically can include hydrophilic adsorbents typified by silica gel, alumina, zeolite, bauxite, magnesia, activated white earth and acrylic synthetic adsorbents, and hydrophobic adsorbents typified by vegetable charcoal, bone charcoal, activated charcoal and aromatic synthetic adsorbents. Any adsorbent can be used without particular limitation as long as the purity of the 3-amino-4-hydroxybenzoic acid-type compound can be enhanced by adsorbing the impurities. In this regard, however, the impurities adsorbed by the porous adsorbent abundantly contain aromatic compounds mainly produced in the process of biochemical synthesis. Thus, the hydrophobic adsorbent typified by the activated charcoal and the aromatic synthetic adsorbent to which these compounds easily adsorb can be suitably used. These hydrophobic adsorbents may be used alone or in combinations of two or more.

When activated charcoal is used, its raw material is not particularly limited, and may include, but is not particularly limited to, plant raw materials such as vegetable powder and palm shell, coal/petroleum-based raw materials such as smokeless coal, petroleum pitch and cokes, synthetic resin-based raw materials such as acrylic resins, phenol resins, epoxy resins and polyester resins. Shapes of the activated charcoal are powder, grain and fibrous, and secondary processed articles such as filters and cartridges, and that easily handled may be appropriately selected.

Meanwhile, when the aromatic synthetic adsorbent is used, the raw material thereof is not particularly limited, and for example, porous resins such as 1) unsubstituted aromatic resins, 2) aromatic resins having a hydrophobic substituent(s), and 3) aromatic resins obtained by giving a special treatment to the unsubstituted aromatic resins can be used. Specific compounds may include, for example, styrene- and divinylbenzene-based resins.

As mentioned above, an object of contacting the 3-amino-4-hydroxybenzoic acid-type compound in the culture medium with the porous adsorbent is to adsorb the impurities to the porous adsorbent to improve the purity of the 3-amino-4-hydroxybenzoic acid-type compound. However, 3-amino-4-hydroxybenzoic acid which is an objective product in no small part is adsorbed together with the impurities to the porous adsorbent in some cases. Thus, it is also possible to isolate and recover the 3-amino-4-hydroxybenzoic acid-type compound by contacting the 3-amino-4-hydroxybenzoic acid-type compound in the culture medium to the porous adsorbent, then contacting the porous adsorbent with a polar organic solvent to detach and dissolve the 3-amino-4-hydroxybenzoic acid-type compound in the polar organic solvent. The polar organic solvent can refer to the organic solvent composed of polar molecules having a high dielectric constant, and can be used without particular limitation as long as the 3-amino-4-hydroxybenzoic acid-type compound can be detached from the porous adsorbent and the 3-amino-4-hydroxybenzoic acid-type compound can be dissolved in the polar organic solvent. The polar organic solvent may be used alone or in combinations of two or more at a desired combination ratio.

The crystallization or the precipitation can refer to a manipulation to produce a crystal or a precipitate by evaporating the solvent in which an objective substance is dissolved to concentrate, or lowering the temperature, or keeping the concentration higher than a saturation solubility by adding a poor solvent to the solvent in which an objective substance is dissolved, and is not particularly limited including conventionally and publicly known methods. The produced crystal or precipitate can be separated by precipitation, filtration, centrifugation or the like.

The method for producing the polybenzoxazole polymer can include producing the polymer including polymerizing the 3-amino-4-hydroxybenzoic acid-type compound obtained by the aforementioned methods. As mentioned above, the 3-amino-4-hydroxybenzoic acid-type compound whose purity has been improved from the culture medium of the coryneform bacterium by using the porous adsorbent or by the crystallization, the precipitation or the like is polymerized by condensation polymerization in a non-oxidizing solvent acid such as methanesulfonic acid or polyphosphoric acid at high temperature (see U.S. Pat. No. 3,354,568). The method for polymerization is practicable by applying publicly known various methods (U.S. Pat. No. 5,142,021, U.S. Pat. No. 5,219,981 and U.S. Pat. No. 5,422,416).

EXAMPLES

Hereinafter, the present invention will be described more specifically with reference to the following non-limiting examples.

Example 1

Construction of a Plasmid for Expressing the Gene of the 3,4-AHBA Synthesis Enzyme Derived from *S. griseus* IFO13350

(1) Acquisition of the Gene Encoding the 3,4-AHBA Synthesis Enzyme Derived from *S. griseus* IFO13350

The sequence of a griI gene and a griH gene (hereinafter, both the genes are together referred to as the gene of the 3,4-AHBA synthesis enzyme) derived from *S. griseus* IFO13350 have been already reported (J. Bio. Chem., 281, 823-833 (2006)). Primers shown in SEQ ID NOS: 1 and 2 were synthesized with reference to this reported sequence, and a region encoding the genetic sequence of the 3,4-AHBA synthesis enzyme was amplified by PCR from the chromosomal DNA of *S. griseus* IFO13350 prepared according to a standard method (Saito and Miura's method [Biochem. Biophys. Acta., 72, 619 (1963)]). Pyrobest DNA polymerase (supplied from Takara Shuzo Co., Ltd.) was used for the PCR, and the reaction was performed under reaction conditions according to the protocol recommended by the manufacturer.

As a result, a fragment of about 2.1 kb amplified by PCR was obtained, the nucleotide sequence of this fragment was determined, and the fragment was confirmed to be a fragment which includes the griIH gene. The nucleotide sequence was determined using Dye Terminator Cycle Sequencing Kit (supplied from PE Applied Biosystems) and DNA sequencer 373A (supplied from PE Applied Biosystems). The sequence of the griIH gene is shown in SEQ ID NO: 7.

(2) Conversion of Promoter Region of the Gene Encoding the 3,4-AHBA Synthesis Enzyme It is necessary to effectively express the gene encoding the 3,4-AHBA synthesis enzyme derived from *S. griseus* IFO13350 in *Corynebacterium*. Thus, the promoter of the gene encoding PS2 from *Corynebacterium glutamicum* was introduced upstream of the griIH gene. The sequence of the gene encoding PS2, which is a cell surface layer protein in *C. glutamicum*, had already been reported (Mol. Microbiol., 9, 97-109 (1993)). The primers shown in SEQ ID NOS:3 and 4 were synthesized with reference to this reported sequence, and a region including the promoter in the 5'-up stream region of the initiation codon of the gene of the PS2 protein was amplified by PCR from the chromosomal DNA of *C. glutamicum* ATCC13869. Pyrobest DNA polymerase (supplied from Takara Shuzo Co., Ltd.) was used for PCR, and the reaction was performed under reaction conditions according to the protocol recommended by the manufacturer.

As a result, a fragment of about 0.5 kb amplified by PCR was obtained, the nucleotide sequence of this fragment was determined, and this fragment was confirmed to include the promoter in the 5' upstream region of the initiation codon of the gene of the PS2 protein. The nucleotide sequence was determined according to the aforementioned method.

The primer shown in SEQ ID NO: 6 was synthesized based on the sequence of the griIH gene determined in Example 1 (1), and the primer shown in SEQ ID NO: 5 was synthesized based on the nucleotide sequence of the region including the promoter in the 5' upstream region of the initiation codon of the gene of the PS2 protein. The primers shown in SEQ ID NOs: 5 and 6 are cassette primers of KpnI.

Subsequently, the amplified fragment of the region including the promoter of the PS2 gene from *C. glutamicum* ATCC13869 and 1 µL of the PCR solution of the amplified fragment of the griIH gene region were mixed to use as the template. A crossover PCR was performed using the primers of SEQ ID NOs: 5 and 6 to amplify the fused griIH gene linked to the region including the promoter of the gene of the cell surface layer protein from *C. glutamicum* ATCC13869. An amplified fragment of about 2.6 kb was detected on agarose gel electrophoresis. This fragment was recovered from the agarose gel using EASYTRAP Ver.2 (supplied from Takara Shuzo Co., Ltd.), and inserted into a KpnI site on the plasmid pPK4 described in JP Hei-9-322774-A to construct the plasmid pPK4griIH. The nucleotide sequence of the inserted fragment was determined according to the aforementioned method, and it was confirmed that the fusion gene was constructed as expected.

Example 2

Production of 3,4-AHBA by *Corynebacterium glutamicum* Using a Fusion Gene Encoding the griIH Gene Derived from *S. griseus* IFO13350

(1) Transformation of *Corynebacterium glutamicum* Using the Fusion Gene Encoding griIH Gene Derived from *S. griseus* IFO13350

*Corynebacterium glutamicum* wild-type strain, *C. glutamicum* ATCC13869 or *C. glutamicum* AJ110135 was transformed with the plasmid pPK4griIH constructed in Example 1 (promoter is derived from the PS2 gene of *C. glutamicum* ATCC13869 and the griIH gene is derived from *S. griseus* IFO13350). Bacterial strains were grown and selected in CM2G agar medium (yeast extract 10 g, trypton 10 g, glucose 5 g, NaCl 5 g and agar 15 g were prepared in 1 L of water, which was then sterilized at 120° C. for 20 minutes) containing 25 mg/L of kanamycin. In *C. glutamicum* AJ110135, aspartokinase was desensitized and the lysine permease was deleted by introducing the mutation which substitutes the alanine residue at position 279 with the threonine residue, as described in JP 2004-261150-A. This bacterial strain can be constructed from *C. glutamicum* ATCC13869 by the method described in JP 2004-261150-A.

(2) Production of 3,4-AHBA by *Corynebacterium glutamicum* Using a Flask

*C. glutamicum* ATCC13869 having pPK4griIH or *C. glutamicum* AJ110135 having pPK4griIH selected in Example 2 (1) was cultured in a flask evaluation medium (100 g of glucose, 1 g of magnesium sulfate heptahydrate, 55 g of ammonium sulfate, 1 g of potassium dihydrogen phosphate, 0.01 g of iron sulfate heptahydrate, 0.01 g of manganese sulfate pentahydrate, 2 mg of thiamine hydrochloride, 0.5 mg of biotin, 5 mg of nicotine amide, 1.05 g of soy concentrate (hydrolyzed soy protein, as total nitrogen content) and 50 g of calcium carbonate were adjusted in 1 L of water to pH 7.2, and sterilized at 115° C. for 15 minutes) at 30° C. for 71 hours at 120 rpm. As a control experiment, *C. glutamicum* ATCC13869 in which no pPK4griIH was introduced was also cultured. When the colony of *C. glutamicum* ATCC13869 having pPK4griIH or *C. glutamicum* AJ110135 having pPK4griIH was cultured, kanamycin at a final concentration of 25 mg/L was added to the flask evaluation medium. After culturing for 71 hours, glucose was completely consumed under all of the conditions. The *C. glutamicum* ATCC13869 having pPK4griIH and *C. glutamicum* AJ110135 having pPK4griIH accumulated 0.7 g/L and 1.4 g/L of 3,4-AHBA, respectively (Table 1). Meanwhile, the *C. glutamicum* ATCC13869 having no pPK4griIH produced no 3,4-AHBA. 3,4-AHBA was quantified using the reverse phase chromatography according to Suzuki et al's method (J. Bio. Chem., 281, 823-833 (2006)). From the above results, it was shown that 3,4-AHBA could be produced by introducing the griIH gene derived from *S. griseus* IFO13350 into *Corynebacterium glutamicum*. The *C. glutamicum* AJ110135 having the mutated aspartokinase in which feedback inhibition is desensitized accumulated 3,4-AHBA more abundantly than the wild-type strain *C. glutamicum* ATCC13869 due to introduction of pPK4griIH.

TABLE 1

|  | C.T. H | O.D. × 60,610 nm | AHBA g/L | Lys g/L | R.S. g/L |
|---|---|---|---|---|---|
| 2256 | 71 | 1.49 | N.D. | 0.5 | N.D. |
| 2256/griIH | 71 | 1.56 | 0.69 | 0.3 | N.D. |
| 2256 CI/griIH | 71 | 1.42 | 1.39 | 18.0 | N.D. |

(3) Production of 3,4-AHBA by *Corynebacterium glutamicum* Using Jar Fermenter

The following experiment was performed using *C. glutamicum* AJ110135 having pPK4griIH obtained in Example 2 (1).

50 mL of medium (5 g of glucose, 10 g of polypeptone, 10 g of yeast extract, 5 g of NaCl, 0.2 g of DL-methionine and 1000 mL of distilled water (pH 7.2)) was dispensed in each Sakaguchi flask, which was then sterilized at 120° C. for 20 minutes. The *C. glutamicum* AJ110135 having pPK4griIH was inoculated into this medium, and cultured with shaking at 30° C. for 24 hours.

The medium A composed of 40 g of glucose, 0.4 g of magnesium sulfate heptahydrate and 100 mL of distilled water, and the medium B composed of 1.2 g of ammonium sulfate, 0.4 g of potassium dihydrogen phosphate, 4 mg of iron sulfate heptahydrate, 4 mg of manganese sulfate pentahydrate, 800 µg of thiamine hydrochloride, 20 µg of biotin, 200 µg of nicotine amide, 0.42 g of soy concentrate (hydrolyzed soy protein, as total nitrogen content), 40 µL of GD-113K and 260 mL of distilled water, were sterilized at 120° C. for 20 minutes. The sterilized medium A and medium B were placed and mixed in a 1.5 L jar fermenter likewise sterilized at 120° C. for 20 minutes, and kanamycin was added to a final concentration of 25 mg/L. 40 mL of the above cultured medium was inoculated into this mixed medium, and the cultivation was performed under the following conditions. The cultivation was maintained at 30° C. at pH 7.2 with stifling at 600 rpm under a constant controlled supply of oxygen at a rate of 0.5 vvm. When glucose in the mixed medium was almost completely consumed, the addition of a 70% glucose solution was started, and a flow rate was manually controlled so that the glucose concentration was 10 g/L to 30 g/L. When about 180 mL of the 70% glucose solution was added, the addition was stopped. An aliquot was appropriately sampled from the medium. The sampled aliquot was diluted to 100 times with 0.1 N HCl, and centrifuged (14000 rpm, 5 minutes, 4° C.) to obtain a culture supernatant. The concentration of 3,4-AHBA in the culture supernatant was analyzed according to the method in Example 2 (2). As a result, about 17.7 g/L of 3,4-AHBA was accumulated in the culture supernatant obtained by culturing the *C. glutamicum* AJ110135 having pPK4griIH for 87 hours (FIG. 5).

Example 3

Confirmation of the Effect of the Enhanced Expression of the Mutated Aspartokinase Gene in Which Feedback Inhibition is Desensitized or Enhanced Expression of the Pyruvate Carboxylase Gene, on Improved Formation of 3,4-AHBA in *C. glutamicum* AJ110135

(1) Construction of a Plasmid Expressing the Mutated Aspartokinase Gene Derived from *C. glutamicum* AJ110135 in which Feedback Inhibition is Desensitized The sequence of the mutated aspartokinase gene derived from *C. glutamicum* AJ110135 in which feedback inhibition is desensitized (hereinafter described as $AK^{fbr}$) has been already determined and its mutation point had been reported (JP 2004-261150-A). The primers shown in SEQ ID NO: 39 and SEQ ID NO: 40 were synthesized with reference to this sequence, and a region including the promoter in the 5' upstream region of the initiation codon of the $AK^{fbr}$ gene was amplified by PCR from chromosomal DNA of *C. glutamicum* AJ110135 prepared according to standard methods. Pyrobest DNA polymerase (supplied from Takara Shuzo Co., Ltd.) was used for PCR, and the reaction was performed under reaction conditions according to the protocol recommended by its manufacturer.

As a result, a fragment of about 1.8 kb amplified by PCR was obtained, the nucleotide sequence of this fragment was determined, and this fragment was confirmed to be the fragment including the $AK^{fbr}$ gene. The nucleotide sequence was determined using Dye Terminator Cycle Sequencing Kit (supplied from PE Applied Biosystems) and DNA sequencer 373A (supplied from PE Applied Biosystems). The nucleotide sequence of the $AK^{fbr}$ gene and a corresponding amino acid sequence are shown in SEQ ID NO: 41 and SEQ ID NO: 42, respectively. This fragment was recovered from the agarose gel using EASYTRAP Ver.2 (supplied from Takara Shuzo Co., Ltd.), and inserted into a SmaI site of the plasmid pVC7 described in JP Hei-9-070291-A to construct the plasmid pVC7$AK^{fbr}$. The nucleotide sequence of the inserted fragment was determined according to the aforementioned method, and it was confirmed that the fusion gene had been constructed as expected.

(2) Transformation of *Corynebacterium glutamicum* Using a Fusion Gene Encoding the $AK^{fbr}$ Gene Derived from *C. glutamicum* AJ110135

The *C. glutamicum* AJ110135 strain was transformed with the plasmid pVC7$AK^{fbr}$ constructed in Example 3 (1). A bacterial strain (*C. glutamicum* AJ110135 having enhanced $AK^{fbr}$ gene) was grown and selected in CM2G agar medium (yeast extract 10 g, trypton 10 g, glucose 5 g, NaCl 5 g and agar 15 g were prepared in 1 L of water) containing 25 mg/L of kanamycin and 5.0 mg/L of chloramphenicol.

(3) Construction of Plasmid Expressing the Pyruvate Carboxylase Gene Derived from *C. glutamicum* ATCC13869

The sequence of the pyruvate carboxylase gene derived from *C. glutamicum* ATCC13869 (hereinafter described as PC gene) had been already determined (Appl. Microbiol. Biotechnol., 50, 346-352 (1998)). The primers shown in SEQ ID NO: 43 and SEQ ID NO: 44 were synthesized with reference to this sequence, and a region including the promoter in the 5' upstream region of the initiation codon of the PC gene was amplified by PCR from chromosomal DNA of *C. glutamicum* ATCC13869 prepared according to standard methods. Pyrobest DNA polymerase (supplied from Takara Shuzo Co., Ltd.) was used for PCR, and the reaction was performed under reaction conditions according to the protocol recommended by its manufacturer.

As a result, a fragment of about 4.1 kb amplified by PCR was obtained, the nucleotide sequence of this fragment was determined, and this fragment was confirmed to include the PC gene. The nucleotide sequence was determined using Dye Terminator Cycle Sequencing Kit (supplied from PE Applied Biosystems) and DNA sequencer 373A (supplied from PE Applied Biosystems). The nucleotide sequence of the PC gene and the corresponding amino acid sequence are shown in SEQ ID NO: 45 and SEQ ID NO: 46, respectively. This fragment was recovered from the agarose gel using EASYTRAP Ver.2 (supplied from Takara Shuzo Co., Ltd.), and inserted into the SmaI site of the plasmid pVC7 described in JP Hei-9-070291-A to construct the plasmid pVC7PC. The nucleotide sequence of the inserted fragment was determined according to the aforementioned method, and it was confirmed that the fusion gene had been constructed as expected.

(4) Transformation of *Corynebacterium glutamicum* Using a Fusion Gene Encoding PC Gene Derived from *C. glutamicum* ATCC13869

*C. glutamicum* AJ110135 was transformed with the plasmid pVC7PC constructed in Example 3 (3). A bacterial strain (*C. glutamicum* AJ110135 having enhanced PC gene) was grown and selected in CM2G agar medium (yeast extract 10 g, trypton 10 g, glucose 5 g, NaCl 5 g and agar 15 g were prepared in 1 L of water) containing 25 mg/L of kanamycin and 5.0 mg/L of chloramphenicol.

(5) Confirmation of the Effect of *C. glutamicum* AJ110135 Having an Enhanced $AK^{fbr}$ Gene and *C. glutamicum* AJ110135 Having an Enhanced PC Gene, on Improved Formation of 3,4-AHBA The *C. glutamicum* AJ110135 having an enhanced $AK^{fbr}$ gene and the *C. glutamicum* AJ110135 having an enhanced PC gene selected in Example 3 (2) and (3), respectively were cultured in the flask evaluation medium (100 g of glucose, 1 g of magnesium sulfate heptahydrate, 55 g of ammonium sulfate, 1 g of potassium dihydrogen phosphate, 0.01 g of iron sulfate heptahydrate, 0.01 g of manganese sulfate pentahydrate, 2 mg of thiamine hydrochloride, 0.5 mg of biotin, 5 mg of nicotine amide, 1.05 g of soy concentrate (hydrolyzed soy protein, as total nitrogen content) and 50 g of calcium carbonate were adjusted in 1 L of water to pH 7.2, and kanamycin was added at a final concentration of 25 mg/L and chloramphenicol was added at a final concentration of 5.0 mg/L) at 30° C. for 71 hours at 120 rpm. As the control experiment, the *C. glutamicum* AJ110135 with the pVC7 was cultured in the above flask evaluation medium with kanamycin at a final concentration of 25 mg/L for 71 hours. As a result, glucose was completely consumed in all of the experiments. 1.0 g/L of 3,4-AHBA was accumulated in the culture of *C. glutamicum* AJ110135 having the enhanced $AK^{fbr}$ gene, and 0.6 g/L of 3,4-AHBA was accumulated in the culture of *C. glutamicum* AJ110135 having the enhanced PC gene (Table 2). Meanwhile, 0.5 g/L of 3,4-AHBA was accumulated in the culture of *C. glutamicum* AJ110135 having introduced pVC7 as the control experiment. From the above results, the ability to form AHBA was improved in *C. glutamicum* AJ110135 having the enhanced $AK^{fbr}$ gene and *C. glutamicum* AJ110135 having the enhanced PC gene compared with *C. glutamicum* AJ110135 as the control.

TABLE 2

|  | C.T. H | O.D. × 60,610 nm | AHBA g/L | Lys g/L | R.S. g/L |
|---|---|---|---|---|---|
| 2256 CI/griIH/pVC7 | 71 | 1.32 | 0.5 | 25.9 | N.D. |
| 2256 CI/griIH/AK$^{fbr}$-1 | 71 | 1.36 | 1.0 | 18.6 | N.D. |
| 2256 CI/griIH/PC | 71 | 1.26 | 0.6 | 32.2 | N.D. |

DESCRIPTION OF SEQUENCE LISTING

SEQ ID NO:1 Primer for amplifying a DNA fragment including a griIH gene
SEQ ID NO:2 Primer for amplifying a DNA fragment including a griIH gene
SEQ ID NO:3 Primer for amplifying a DNA fragment including a promoter region of a gene of a PS2 protein
SEQ ID NO:4 Primer for amplifying a DNA fragment including a promoter region of a gene of a PS2 protein
SEQ ID NO:5 Primer for amplifying a DNA fragment including a promoter region of a gene of a PS2 protein, and a griIH gene
SEQ ID NO:6 Primer for amplifying a DNA fragment including a promoter region of a gene of a PS2 protein, and a griIH gene
SEQ ID NO:7 a griIH gene
SEQ ID NO:8 Sequence of a griI gene derived from *Streptomyces griseus*
SEQ ID NO:9 Amino acid sequence of a griI derived from *Streptomyces griseus*
SEQ ID NO:10 Sequence of a griI gene derived from *Frankia* sp.
SEQ ID NO:11 Amino acid sequence of a griI derived from *Frankia* sp.
SEQ ID NO:12 Sequence of a griI gene derived from *Frankia* sp.
SEQ ID NO:13 Amino acid sequence of a griI derived from *Frankia* sp.
SEQ ID NO:14 Sequence of a griI gene derived from *Streptomyces scabies*
SEQ ID NO:15 Amino acid sequence of a griI derived from *Streptomyces scabies*
SEQ ID NO:16 Sequence of a griI gene derived from *Burkholderia* sp. 383
SEQ ID NO:17 Amino acid sequence of a griI derived from *Burkholderia* sp. 383
SEQ ID NO:18 Sequence of a griI gene derived from *Methanococcus jannaschii*
SEQ ID NO:19 Amino acid sequence of a griI derived from *Methanococcus jannaschii*
SEQ ID NO:20 Sequence of a dhnA gene derived from *Escherichia coli*
SEQ ID NO:21 Amino acid sequence of a dhnA derived from *Escherichia coli*
SEQ ID NO:22 Sequence of a griH gene derived from *Streptomyces griseus*
SEQ ID NO:23 Amino acid sequence of a griH derived from *Streptomyces griseus*
SEQ ID NO:24 Sequence of a griH gene derived from *Frankia* sp.
SEQ ID NO:25 Amino acid sequence of a griH derived from *Frankia* sp.
SEQ ID NO:26 Sequence of a griH gene derived from *Frankia* sp.
SEQ ID NO:27 Amino acid sequence of a griH derived from *Frankia* sp.
SEQ ID NO:28 Sequence of a griH gene derived from *Burkholderia* sp. 383
SEQ ID NO:29 Amino acid sequence of a griH derived from *Burkholderia* sp. 383
SEQ ID NO:30 Sequence of a griH gene derived from *Burkholderia* sp. 383
SEQ ID NO:31 Amino acid sequence of a griH derived from *Burkholderia* sp. 383
SEQ ID NO:32 Sequence of a griH gene derived from *Streptomyces scabies*
SEQ ID NO:33 Amino acid sequence of a griH derived from *Streptomyces scabies*
SEQ ID NO:34 Sequence of a griH gene derived from *Methanococcus jannaschii*
SEQ ID NO:35 Amino acid sequence of a griH derived from *Methanococcus annaschii*
SEQ ID NO:36 griI consensus sequence
SEQ ID NO:37 griH consensus sequence
SEQ ID NO:38 Amino acid sequence of α-subunit of an aspartokinase derived from *Corynebacterium glutamicum* ATCC13869
SEQ ID NO:39 Primer for amplifying a DNA fragment including an AK$^{fbr}$ gene
SEQ ID NO:40 Primer for amplifying a DNA fragment including an AK$^{fbr}$ gene
SEQ ID NO:41 Nucleotide sequence of an AK$^{fbr}$ gene derived from *Corynebacterium glutamicum* ATCC13869
SEQ ID NO:42 Amino acid sequence of an AK$^{fbr}$ protein derived from *Corynebacterium glutamicum* ATCC13869
SEQ ID NO:43 Primer for amplifying a DNA fragment including a PC gene
SEQ ID NO:44 Primer for amplifying a DNA fragment including a PC gene
SEQ ID NO:45 Nucleotide sequence of a PC gene derived from *Corynebacterium glutamicum* ATCC13869
SEQ ID NO:46 Amino acid sequence of a PC protein derived from *Corynebacterium glutamicum* ATCC13869

INDUSTRIAL APPLICABILITY

According to the present invention, it is possible to conveniently and inexpensively produce an aminohydroxybenzoic acid-type compound which is useful as an intermediate in the manufacturer of dyes, agricultural chemicals, pharmaceuticals and other synthetic organic compounds, and as a monomer for polybenzoxazole. Thus, for example, polybenzoxazole (PBO) is obtained by polymerizing 3-amino-4-hydroxybenzoic acid obtained by the present invention, thereby inexpensively providing PBO fibers and PBO films having high strength, high elastic modulus, and high heat resistance. Since the 3-amino-4-hydroxybenzoic acid-type compound which is a raw material can be produced by biosynthesis, the method of the present invention is an environmentally low load-type process, and a global-environmentally friendly method.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing a 3-amino-4-hydroxybenzoic acid-compound comprising culturing a coryneform bacterium comprising:
    a) a gene encoding an aspartokinase which is not subject to feedback inhibition, and
    b) a recombinant vector comprising a DNA encoding a protein having an activity to form 3-amino-4-hydroxybenzoic acid from dihydroxyacetone phosphate and aspartate semialdehyde.

2. The method according to claim 1, wherein expression of a gene encoding said aspartokinase is enhanced.

3. The method according to claim 1, wherein expression of a pyruvate carboxylase gene is enhanced in said bacterium.

4. The method according to claim 1, wherein said DNA comprises a griI gene and a griH gene.

5. The method according to claim 1, wherein said griI gene and griH gene are derived from Actinomycetes.

6. The method according to claim 1, wherein said coryneform bacterium is *Corynebacterium glutamicum*.

7. A method for producing a polybenzoxazole polymer comprising polymerizing a 3-amino-4-hydroxybenzoic acid compound produced by the method according to claim 1.

8. The method according to claim 5, wherein said griI gene and griH gene are derived from genus *Streptomyces*.

9. The method according to claim 8, wherein said griI gene and griH gene are derived from *Streptomyces griseus*.

* * * * *

SEQUENCE LISTING

<160> NUMBER OF SEQ ID NOS: 46

<210> SEQ ID NO 1
<211> LENGTH: 50
<212> TYPE: DNA
<213> ORGANISM: Artificial
<220> FEATURE:
<223> OTHER INFORMATION: primer

<400> SEQUENCE: 1
acctattcaa ggagccttcg cctctatggc cccgaacgcg cccttcgcca          50

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
agactacttc tccaggcaga actcgttga                                 29

<210> SEQ ID NO 3
<211> LENGTH: 33
<212> TYPE: DNA
<213> ORGANISM: Artificial
<220> FEATURE:
<223> OTHER INFORMATION: primer

<400> SEQUENCE: 3
aaattcctgt gaattagctg atttagtact ttt                            33

<210> SEQ ID NO 4
<211> LENGTH: 50
<212> TYPE: DNA
<213> ORGANISM: Artificial
<220> FEATURE:
<223> OTHER INFORMATION: primer

<400> SEQUENCE: 4
tggcgaaggg cgcgttcggg gccatagagg cgaaggctcc ttgaataggt          50

<210> SEQ ID NO 5
<211> LENGTH: 40
<212> TYPE: DNA
<213> ORGANISM: Artificial
<220> FEATURE:
<223> OTHER INFORMATION: primer

<400> SEQUENCE: 5
ggtacccaaa ttcctgtgaa ttagctgatt tagtactttt                     40

<210> SEQ ID NO 6
<211> LENGTH: 35
<212> TYPE: DNA
<213> ORGANISM: Artificial
<220> FEATURE:
<223> OTHER INFORMATION: primer

<400> SEQUENCE: 6
ggtaccagac tacttctcca ggcagaactc gttga                          35

<210> SEQ ID NO 7
<211> LENGTH: 2091
<212> TYPE: DNA

<213> ORGANISM: Streptomyces griseus

<400> SEQUENCE: 7

```
atggccccga acgcgccctt cgccaggagt ctgcgactcc agcggctcca tcaccacgac      60
cccgaccggc tgttcatcgt gccgctcgac cactcgatca ccgacggccc gctgagccgt     120
gcccaccgcc tcgacccgct cgtcggcgaa ctggcctccc accacgtcga cgggatcgtc     180
ctgcacaagg gctcgctgcg ccacgtggac ccggagtggt tcacgcggac ctcgctgatc     240
gtgcacctca gcgccagcac cgtgcacgcg cccgacccga acgccaagta cctggtgtcg     300
agcgtcgagg agagcctgcg catgggcgcg gacgcggtga cgtccacgt caatctcggc      360
tccgagggg aacgccacca gatcgcggac atggcggcgg tcgcggaggc ctgcgaccgc      420
tggaacgtac cgctgctggc gatgatgtat ccgcgcggcc caagatcga cgacccgcgc      480
gatccggcgc tcgtcgccca tgccgtccag gtggccgtgg acctcggcgc cgacctggtc     540
aagacgctgt acgtcggatc ggtcgcgcg atggccgaga tcaccgcggc ctcgcccgtt      600
ccggtcgtcg tggtcggcgg accgcgcgac agtgacgaga gccggatcct cgcctacgtc     660
gacgacgcgc tgcgcggcgg cgcggccggt gtcgccatgg ccgcaacgt cttccaggcc      720
cctgatcccg gcgcgatggc ggacaagctc tccgacctca tccacaacag cggcaccagg     780
ggcgcggccc gggctccggc cggcgccgcc gccgagccg cctgatccgg ccgacgtcag      840
cgcccggaac cgcaccacga gtccccgttc accgtcccat cgccactgag gagttctctc     900
atgtcttcgt ctccgtctcc gtctccgtcc tcgtcgtcct cgtcatctgc gtcctcgtcg     960
gcttcgtcgt cgccttcgtc gtcgtcgaag ctgacctggc tcgacatccg ttccgtgggc    1020
gaggcccgtg ccgccatcgt ccaggaggcc ctgcaccacc gggtggaagc gctggtcgcc    1080
gacgaccccg cccacctcgc ggacctgccg cccaccgtgg ccaaggtcct gctggtggtg    1140
gggaagcaga tccggagga gttcggcgag gcgacggtcg tcgtcgtcga cccgtcgaag    1200
cacggtgtga ccccgccga actggcgctc aagcacccgg agatcgagtt cgggcggttc    1260
gtggagatca tcgacgcgcc gacgctggag gacgcctgcg agtcctcgcg gaccgagaag    1320
tggtccgtcc tgctgttccg cgacccgacc aagatcccgc tggagatcgt gatcgccgcc    1380
gccgcgcgcg cctccggttc gatggtgacc atcgcgcagg acctggagga ggcggagatc    1440
ctcttcggcg tgctggagca cggctcggac ggcgtgatga tggcccccga acggtcggt    1500
gacgccgccg agctgaagcg gatcgccgag gccggcatcc ccaacctcaa cctcaccgag    1560
ctgcgcgtcg tggagaccag ccacatcggc atgggcgagc gggcctgcgt ggacaccacc    1620
acgcatttcg gcgaggacga gggcatcctg gtcggctcgc actccaaggg catgatcctc    1680
tgcgtcagcg agacccaccc gctgccgtac atgccgaccc ggccgttccg cgtcaacgcc    1740
ggcgccatcc actcgtacac gctgggcagg gacgagcgca cgaactacct gagcgaactg    1800
aagacgggca gcaagctcac cgccgtcgac atcaagggca cacccggct ggtgaccgtg     1860
ggccgcgtga agatcgagac ccgcccgctg atctccatcg acgccgaggc cccggacggc    1920
cggcgcgtca acctgatcct ccaggacgac tggcacgtcc gggtcctcgg ccccggtggc    1980
acggtcctca acagcaccga gctgaagccc ggcgacacgg tcctcggcta cctgcccgtc    2040
gaggaccgtc acgtcggcta cccgatcaac gagttctgcc tggagaagta g             2091
```

<210> SEQ ID NO 8
<211> LENGTH: 825
<212> TYPE: DNA
<213> ORGANISM: Streptomyces griseus
<220> FEATURE:

<221> NAME/KEY: CDS
<222> LOCATION: (1)..(825)

<400> SEQUENCE: 8

```
atg gcc ccg aac gcg ccc ttc gcc agg agt ctg cga ctc cag cgg ctc      48
Met Ala Pro Asn Ala Pro Phe Ala Arg Ser Leu Arg Leu Gln Arg Leu
1               5                   10                  15 cat cac cac gac ccc gac cgg ctg ttc atc gtg ccg ctc gac cac tcg      96
His His His Asp Pro Asp Arg Leu Phe Ile Val Pro Leu Asp His Ser
            20                  25                  30 atc acc gac ggc ccg ctg agc cgt gcc cac cgc ctc gac ccg ctc gtc     144
Ile Thr Asp Gly Pro Leu Ser Arg Ala His Arg Leu Asp Pro Leu Val
        35                  40                  45 ggc gaa ctg gcc tcc cac cac gtc gac ggg atc gtc ctg cac aag ggc     192
Gly Glu Leu Ala Ser His His Val Asp Gly Ile Val Leu His Lys Gly
50                  55                  60 tcg ctg cgc cac gtg gac ccg gag tgg ttc acg cgg acc tcg ctg atc     240
Ser Leu Arg His Val Asp Pro Glu Trp Phe Thr Arg Thr Ser Leu Ile
65                  70                  75                  80 gtg cac ctc agc gcc agc acc gtg cac gcg ccc gac ccg aac gcc aag     288
Val His Leu Ser Ala Ser Thr Val His Ala Pro Asp Pro Asn Ala Lys
                85                  90                  95 tac ctg gtg tcg agc gtc gag gag agc ctg cgc atg ggc gcg gac gcg     336
Tyr Leu Val Ser Ser Val Glu Glu Ser Leu Arg Met Gly Ala Asp Ala
            100                 105                 110 gtg agc gtc cac gtc aat ctc ggc tcc gag ggg gaa cgc cac cag atc     384
Val Ser Val His Val Asn Leu Gly Ser Glu Gly Glu Arg His Gln Ile
        115                 120                 125 gcg gac atg gcg gcg gtc gcg gag gcc tgc gac cgc tgg aac gta ccg     432
Ala Asp Met Ala Ala Val Ala Glu Ala Cys Asp Arg Trp Asn Val Pro
130                 135                 140 ctg ctg gcg atg atg tat ccg cgc ggc ccc aag atc gac gac ccg cgc     480
Leu Leu Ala Met Met Tyr Pro Arg Gly Pro Lys Ile Asp Asp Pro Arg
145                 150                 155                 160 gat ccg gcg ctc gtc gcc cat gcc gtc cag gtg gcc gtg gac ctc ggc     528
Asp Pro Ala Leu Val Ala His Ala Val Gln Val Ala Val Asp Leu Gly
                165                 170                 175 gcc gac ctg gtc aag acg ctg tac gtc gga tcg gtc gcg gcg atg gcc     576
Ala Asp Leu Val Lys Thr Leu Tyr Val Gly Ser Val Ala Ala Met Ala
            180                 185                 190 gag atc acc gcg gcc tcg ccc gtt ccg gtc gtc gtg gtc ggc gga ccg     624
Glu Ile Thr Ala Ala Ser Pro Val Pro Val Val Val Val Gly Gly Pro
        195                 200                 205 cgc gac agt gac gag agc cgg atc ctc gcc tac gtc gac gac gcg ctg     672
Arg Asp Ser Asp Glu Ser Arg Ile Leu Ala Tyr Val Asp Asp Ala Leu
210                 215                 220 cgc ggc ggc gcc gcc ggt gtc gcc atg ggc cgc aac gtc ttc cag gcc     720
Arg Gly Gly Ala Ala Gly Val Ala Met Gly Arg Asn Val Phe Gln Ala
225                 230                 235                 240 cct gat ccc ggc gcg atg gcg gac aag ctc tcc gac ctc atc cac aac     768
Pro Asp Pro Gly Ala Met Ala Asp Lys Leu Ser Asp Leu Ile His Asn
                245                 250                 255 agc ggc acc agg ggc gcg gcc cgg gct ccg gcc ggc gcc gcc gcc gga     816
Ser Gly Thr Arg Gly Ala Ala Arg Ala Pro Ala Gly Ala Ala Ala Gly
            260                 265                 270 gcc gcc tga                                                         825
Ala Ala
```

<210> SEQ ID NO 9
<211> LENGTH: 274
<212> TYPE: PRT

<213> ORGANISM: Streptomyces griseus

<400> SEQUENCE: 9

```
Met Ala Pro Asn Ala Pro Phe Ala Arg Ser Leu Arg Leu Gln Arg Leu
1               5                   10                  15

His His His Asp Pro Asp Arg Leu Phe Ile Val Pro Leu Asp His Ser
            20                  25                  30

Ile Thr Asp Gly Pro Leu Ser Arg Ala His Arg Leu Asp Pro Leu Val
        35                  40                  45

Gly Glu Leu Ala Ser His His Val Asp Gly Ile Val Leu His Lys Gly
    50                  55                  60

Ser Leu Arg His Val Asp Pro Glu Trp Phe Thr Arg Thr Ser Leu Ile
65                  70                  75                  80

Val His Leu Ser Ala Ser Thr Val His Ala Pro Asp Pro Asn Ala Lys
                85                  90                  95

Tyr Leu Val Ser Ser Val Glu Glu Ser Leu Arg Met Gly Ala Asp Ala
            100                 105                 110

Val Ser Val His Val Asn Leu Gly Ser Glu Gly Arg His Gln Ile
        115                 120                 125

Ala Asp Met Ala Ala Val Ala Glu Ala Cys Asp Arg Trp Asn Val Pro
    130                 135                 140

Leu Leu Ala Met Met Tyr Pro Arg Gly Pro Lys Ile Asp Asp Pro Arg
145                 150                 155                 160

Asp Pro Ala Leu Val Ala His Ala Val Gln Val Ala Val Asp Leu Gly
                165                 170                 175

Ala Asp Leu Val Lys Thr Leu Tyr Val Gly Ser Val Ala Ala Met Ala
            180                 185                 190

Glu Ile Thr Ala Ala Ser Pro Val Pro Val Val Val Gly Gly Pro
        195                 200                 205

Arg Asp Ser Asp Glu Ser Arg Ile Leu Ala Tyr Val Asp Asp Ala Leu
    210                 215                 220

Arg Gly Gly Ala Ala Gly Val Ala Met Gly Arg Asn Val Phe Gln Ala
225                 230                 235                 240

Pro Asp Pro Gly Ala Met Ala Asp Lys Leu Ser Asp Leu Ile His Asn
                245                 250                 255

Ser Gly Thr Arg Gly Ala Ala Arg Ala Pro Ala Gly Ala Ala Ala Gly
            260                 265                 270

Ala Ala
```

<210> SEQ ID NO 10
<211> LENGTH: 819
<212> TYPE: DNA
<213> ORGANISM: Frankia sp.
<220> FEATURE:
<221> NAME/KEY: CDS
<222> LOCATION: (1)..(819)

<400> SEQUENCE: 10

```
atg ccc aac tac ccg ttc tcg cgg ctc gtt cgg ctt cgg agg ctg tat    48
Met Pro Asn Tyr Pro Phe Ser Arg Leu Val Arg Leu Arg Arg Leu Tyr
1               5                   10                  15 cgt cac cac cgt ggc cgt ctg ttt atg gtg ccg ctg gac cac tcc gtc    96
Arg His His Arg Gly Arg Leu Phe Met Val Pro Leu Asp His Ser Val
            20                  25                  30 acc gac ggt cca ctc agc cga cgt cgc tca ctt gat gag ctg atc gag   144
Thr Asp Gly Pro Leu Ser Arg Arg Ser Leu Asp Glu Leu Ile Glu
        35                  40                  45
```

```
gga atc tcc cgc ggc gcc gtc gac gcg gtt gta ctg cac aaa gga agc          192
Gly Ile Ser Arg Gly Ala Val Asp Ala Val Val Leu His Lys Gly Ser
 50                  55                  60 ctg cgg tac cta aac gcc gtc cgc ttc gac cac atg tcg ttg atc gtg          240
Leu Arg Tyr Leu Asn Ala Val Arg Phe Asp His Met Ser Leu Ile Val
 65                  70                  75                  80 caa ctt tca gcc agc acc aga cac gct ccg gac ccc gac gcg aag atc          288
Gln Leu Ser Ala Ser Thr Arg His Ala Pro Asp Pro Asp Ala Lys Ile
                 85                  90                  95 ctg gtg gcg agc gtc gaa gag gcg ctt cgt ctg ggg gcc gac gcc gtc          336
Leu Val Ala Ser Val Glu Glu Ala Leu Arg Leu Gly Ala Asp Ala Val
                100                 105                 110 agc gtc cac gtg aac ctg ggt tcg gca cag gag agc cgt cag atc gcg          384
Ser Val His Val Asn Leu Gly Ser Ala Gln Glu Ser Arg Gln Ile Ala
                115                 120                 125 gac ttg gcg gcg gtg gcg gac tcc tgt gac cgg tgg ggc gtt ccc ctg          432
Asp Leu Ala Ala Val Ala Asp Ser Cys Asp Arg Trp Gly Val Pro Leu
130                 135                 140 ctc gcc atg atg tat ccg cgg ggc ccg agg atc gct gac ccg ccc aac          480
Leu Ala Met Met Tyr Pro Arg Gly Pro Arg Ile Ala Asp Pro Pro Asn
145                 150                 155                 160 gcg gag ttg tgc atg cac gcg gct gtg ctg gcc gcg gac ctc ggt gcg          528
Ala Glu Leu Cys Met His Ala Ala Val Leu Ala Ala Asp Leu Gly Ala
                165                 170                 175 gac ata gtc aag att cct cgc ctc ggc tcg acc gac gag cta cgc gac          576
Asp Ile Val Lys Ile Pro Arg Leu Gly Ser Thr Asp Glu Leu Arg Asp
                180                 185                 190 gtg gtg gcc gcc tca ccg atc ccg acg gtc gtg gcg ggt ggc tcc tca          624
Val Val Ala Ala Ser Pro Ile Pro Thr Val Val Ala Gly Gly Ser Ser
                195                 200                 205 atg gaa ccc gaa gaa tac ctc gcc gaa ctc gcg gcg gcg atg cgg tcc          672
Met Glu Pro Glu Glu Tyr Leu Ala Glu Leu Ala Ala Ala Met Arg Ser
210                 215                 220 ggg gtc ggc ggt gtc gcg atc ggc cgg aat gtc ttt cag gcc ccc gac          720
Gly Val Gly Gly Val Ala Ile Gly Arg Asn Val Phe Gln Ala Pro Asp
225                 230                 235                 240 ccc tgc gcg atg gcg cgt cga atc gcc cag atc gtg cac gat ccg ctt          768
Pro Cys Ala Met Ala Arg Arg Ile Ala Gln Ile Val His Asp Pro Leu
                245                 250                 255 gag gtt gcc agg aag cag ccg agg gtg cag cat agc ggc gcg gtc ggc          816
Glu Val Ala Arg Lys Gln Pro Arg Val Gln His Ser Gly Ala Val Gly
                260                 265                 270 tga                                                                      819

<210> SEQ ID NO 11
<211> LENGTH: 272
<212> TYPE: PRT
<213> ORGANISM: Frankia sp.

<400> SEQUENCE: 11

Met Pro Asn Tyr Pro Phe Ser Arg Leu Val Arg Leu Arg Arg Leu Tyr
 1               5                  10                  15

Arg His His Arg Gly Arg Leu Phe Met Val Pro Leu Asp His Ser Val
                 20                  25                  30

Thr Asp Gly Pro Leu Ser Arg Arg Ser Leu Asp Glu Leu Ile Glu
                 35                  40                  45

Gly Ile Ser Arg Gly Ala Val Asp Ala Val Val Leu His Lys Gly Ser
 50                  55                  60

Leu Arg Tyr Leu Asn Ala Val Arg Phe Asp His Met Ser Leu Ile Val
 65                  70                  75                  80
```

```
Gln Leu Ser Ala Ser Thr Arg His Ala Pro Asp Pro Asp Ala Lys Ile
                85                  90                  95

Leu Val Ala Ser Val Glu Glu Ala Leu Arg Leu Gly Ala Asp Ala Val
            100                 105                 110

Ser Val His Val Asn Leu Gly Ser Ala Gln Glu Ser Arg Gln Ile Ala
        115                 120                 125

Asp Leu Ala Ala Val Ala Asp Ser Cys Asp Arg Trp Gly Val Pro Leu
    130                 135                 140

Leu Ala Met Met Tyr Pro Arg Gly Pro Arg Ile Ala Asp Pro Pro Asn
145                 150                 155                 160

Ala Glu Leu Cys Met His Ala Ala Val Leu Ala Ala Asp Leu Gly Ala
                165                 170                 175

Asp Ile Val Lys Ile Pro Arg Leu Gly Ser Thr Asp Glu Leu Arg Asp
            180                 185                 190

Val Val Ala Ala Ser Pro Ile Pro Thr Val Ala Gly Gly Ser Ser
        195                 200                 205

Met Glu Pro Glu Glu Tyr Leu Ala Glu Leu Ala Ala Met Arg Ser
    210                 215                 220

Gly Val Gly Gly Val Ala Ile Gly Arg Asn Val Phe Gln Ala Pro Asp
225                 230                 235                 240

Pro Cys Ala Met Ala Arg Arg Ile Ala Gln Ile Val His Asp Pro Leu
                245                 250                 255

Glu Val Ala Arg Lys Gln Pro Arg Val Gln His Ser Gly Ala Val Gly
            260                 265                 270

<210> SEQ ID NO 12
<211> LENGTH: 837
<212> TYPE: DNA
<213> ORGANISM: Frankia sp.
<220> FEATURE:
<221> NAME/KEY: CDS
<222> LOCATION: (1)..(837)

<400> SEQUENCE: 12 gtg aca gaa cag cac ttc gcc cgt gcg ctg agg atg gcc cgg ctc cac    48
Met Thr Glu Gln His Phe Ala Arg Ala Leu Arg Met Ala Arg Leu His
1               5                   10                  15 cgc tgg cac ccc gcc agg ctg gcg atc aca ccg ctc gac cac tcg atc    96
Arg Trp His Pro Ala Arg Leu Ala Ile Thr Pro Leu Asp His Ser Ile
            20                  25                  30 agc gac gga ccc gtg gtg ccg cgc ggc acc acc atc gac ggc ctc gca   144
Ser Asp Gly Pro Val Val Pro Arg Gly Thr Thr Ile Asp Gly Leu Ala
        35                  40                  45 ggt cag ctg gtg gag gcc ggc gtg gac gcc atc gtc gtc cac aag ggc   192
Gly Gln Leu Val Glu Ala Gly Val Asp Ala Ile Val Val His Lys Gly
    50                  55                  60 agc ctc cgg cac ctt cgt ccc gcc cgt ctc acc ggc atg tcg gtg atc   240
Ser Leu Arg His Leu Arg Pro Ala Arg Leu Thr Gly Met Ser Val Ile
65                  70                  75                  80 gtc cat ctc aac gca agc acc gct cac gca ccc gat ccg gat gcc aag   288
Val His Leu Asn Ala Ser Thr Ala His Ala Pro Asp Pro Asp Ala Lys
                85                  90                  95 tac ctg gtc acc gga gtg gag gaa gcg ctc agg ctg ggt gcg gac gca   336
Tyr Leu Val Thr Gly Val Glu Glu Ala Leu Arg Leu Gly Ala Asp Ala
            100                 105                 110 gtc agt ctg cac gtc aac ctc ggc tcc ctc gac gaa cgc cag cag atc   384
Val Ser Leu His Val Asn Leu Gly Ser Leu Asp Glu Arg Gln Gln Ile
        115                 120                 125
```

```
ggg gac ctc ggc cgg gtc gcg gag cgc tgc gag cag tgg aac ctg ccg    432
Gly Asp Leu Gly Arg Val Ala Glu Arg Cys Glu Gln Trp Asn Leu Pro
    130                 135                 140 ctg ctc gcg atg atg tac ccg cgc ggg ccg cgg atc agc gac ccg cat    480
Leu Leu Ala Met Met Tyr Pro Arg Gly Pro Arg Ile Ser Asp Pro His
145                 150                 155                 160 gat ccg gag ctg atc gcg cac gcg gtc aca ctc gcc gtg gac ctg ggc    528
Asp Pro Glu Leu Ile Ala His Ala Val Thr Leu Ala Val Asp Leu Gly
                165                 170                 175 gcg gac ctg gtc aag gcc ccc ttc ccc ggg tcc gtc ccg gcc ctg cgc    576
Ala Asp Leu Val Lys Ala Pro Phe Pro Gly Ser Val Pro Ala Leu Arg
            180                 185                 190 gac ctg acg gac gcc tgc ccc gtc ccc ctg ctg tgc gcc ggc gga ccc    624
Asp Leu Thr Asp Ala Cys Pro Val Pro Leu Leu Cys Ala Gly Gly Pro
        195                 200                 205 cgc cgc agt gag gac gac gtt ctg gcg tac gta cgc gac gtg ctg cac    672
Arg Arg Ser Glu Asp Asp Val Leu Ala Tyr Val Arg Asp Val Leu His
    210                 215                 220 ggc ggg gcc gcc ggc gtg gcc atg ggc cgc agc atc ttc cag gcc gac    720
Gly Gly Ala Ala Gly Val Ala Met Gly Arg Ser Ile Phe Gln Ala Asp
225                 230                 235                 240 gac ccg cgg cgg atg gct gcg gcg gtg gcc caa ctg gtc cat gcg gaa    768
Asp Pro Arg Arg Met Ala Ala Ala Val Ala Gln Leu Val His Ala Glu
                245                 250                 255 tcc gag cct cgt ctc gaa ccg act gca gaa ggg cag cga agt gaa cgc    816
Ser Glu Pro Arg Leu Glu Pro Thr Ala Glu Gly Gln Arg Ser Glu Arg
            260                 265                 270 aag gaa gct gtg ctg gct tga                                        837
Lys Glu Ala Val Leu Ala
        275

<210> SEQ ID NO 13
<211> LENGTH: 278
<212> TYPE: PRT
<213> ORGANISM: Frankia sp.

<400> SEQUENCE: 13

Met Thr Glu Gln His Phe Ala Arg Ala Leu Arg Met Ala Arg Leu His
1               5                   10                  15

Arg Trp His Pro Ala Arg Leu Ala Ile Thr Pro Leu Asp His Ser Ile
            20                  25                  30

Ser Asp Gly Pro Val Val Pro Arg Gly Thr Thr Ile Asp Gly Leu Ala
        35                  40                  45

Gly Gln Leu Val Glu Ala Gly Val Asp Ala Ile Val His Lys Gly
    50                  55                  60

Ser Leu Arg His Leu Arg Pro Ala Arg Leu Thr Gly Met Ser Val Ile
65              70                  75                  80

Val His Leu Asn Ala Ser Thr Ala His Ala Pro Asp Pro Ala Lys
                85                  90                  95

Tyr Leu Val Thr Gly Val Glu Glu Ala Leu Arg Leu Gly Ala Asp Ala
            100                 105                 110

Val Ser Leu His Val Asn Leu Gly Ser Leu Asp Glu Arg Gln Gln Ile
        115                 120                 125

Gly Asp Leu Gly Arg Val Ala Glu Arg Cys Glu Gln Trp Asn Leu Pro
    130                 135                 140

Leu Leu Ala Met Met Tyr Pro Arg Gly Pro Arg Ile Ser Asp Pro His
145                 150                 155                 160

Asp Pro Glu Leu Ile Ala His Ala Val Thr Leu Ala Val Asp Leu Gly
                165                 170                 175
```

```
Ala Asp Leu Val Lys Ala Pro Phe Pro Gly Ser Val Pro Ala Leu Arg
            180                 185                 190

Asp Leu Thr Asp Ala Cys Pro Val Pro Leu Leu Cys Ala Gly Gly Pro
        195                 200                 205

Arg Arg Ser Glu Asp Val Leu Ala Tyr Val Arg Asp Val Leu His
    210                 215                 220

Gly Gly Ala Ala Gly Val Ala Met Gly Arg Ser Ile Phe Gln Ala Asp
225                 230                 235                 240

Asp Pro Arg Arg Met Ala Ala Val Ala Gln Leu Val His Ala Glu
                245                 250                 255

Ser Glu Pro Arg Leu Glu Pro Thr Ala Glu Gly Gln Arg Ser Glu Arg
                260                 265                 270

Lys Glu Ala Val Leu Ala
            275

<210> SEQ ID NO 14
<211> LENGTH: 879
<212> TYPE: DNA
<213> ORGANISM: Streptomyces scabies
<220> FEATURE:
<221> NAME/KEY: CDS
<222> LOCATION: (1)..(879)

<400> SEQUENCE: 14
```

| atg cag cct cgg agc tgg gaa ggc gca tta ccc atg ctg aaa acc ggc | 48 |
|---|---|
| Met Gln Pro Arg Ser Trp Glu Gly Ala Leu Pro Met Leu Lys Thr Gly | |
| 1               5                   10                  15 | |

| aag cca tta cgt tgg aga agg ctt tcc cgg gcc ggt gat gac cgg cat | 96 |
|---|---|
| Lys Pro Leu Arg Trp Arg Arg Leu Ser Arg Ala Gly Asp Asp Arg His | |
|             20                  25                  30 | |

| ttg ctc ata cct ctg gac cac agt gtc tcg gac ggc ccg gtc gcc cct | 144 |
|---|---|
| Leu Leu Ile Pro Leu Asp His Ser Val Ser Asp Gly Pro Val Ala Pro | |
|         35                  40                  45 | |

| ccg gga cgg tgg gag gac ctg ctg cgg gag ctg gtg gcc ggc ggg gcc | 192 |
|---|---|
| Pro Gly Arg Trp Glu Asp Leu Leu Arg Glu Leu Val Ala Gly Gly Ala | |
|     50                  55                  60 | |

| gac ggg atc gtc gtc cac aag ggc cgg gcc cgc acc ctc gcg ccc gac | 240 |
|---|---|
| Asp Gly Ile Val Val His Lys Gly Arg Ala Arg Thr Leu Ala Pro Asp | |
| 65                  70                  75                  80 | |

| ctc ctc ggc gac tgc gcg ctg gtc gtg cac ctg agc gcc agt acg gcc | 288 |
|---|---|
| Leu Leu Gly Asp Cys Ala Leu Val Val His Leu Ser Ala Ser Thr Ala | |
|                 85                  90                  95 | |

| tgt tcc gcc gac gtg gac gcc aag gtg ctg gtc ggc gat gtc gag gag | 336 |
|---|---|
| Cys Ser Ala Asp Val Asp Ala Lys Val Leu Val Gly Asp Val Glu Glu | |
|             100                 105                 110 | |

| gcg gtg gca ctc ggc gcg gac gcg gtc agc gtc cat gtg aac atc ggc | 384 |
|---|---|
| Ala Val Ala Leu Gly Ala Asp Ala Val Ser Val His Val Asn Ile Gly | |
|         115                 120                 125 | |

| tcg gac acc gag ggc cgt cag ctc gcc gac ctc ggc gcg gtg gcc cgc | 432 |
|---|---|
| Ser Asp Thr Glu Gly Arg Gln Leu Ala Asp Leu Gly Ala Val Ala Arg | |
|     130                 135                 140 | |

| tcg tgc gac acc tgg ggc atg ccc ctg atc gcg atg gtc tat ccg cgc | 480 |
|---|---|
| Ser Cys Asp Thr Trp Gly Met Pro Leu Ile Ala Met Val Tyr Pro Arg | |
| 145                 150                 155                 160 | |

| ggc ccc cgg atc gag aac ccg cac gat ccc gcc ctg ctc gcc cac gtc | 528 |
|---|---|
| Gly Pro Arg Ile Glu Asn Pro His Asp Pro Ala Leu Leu Ala His Val | |
|                 165                 170                 175 | |

| gtg aac gtc gcc gcc gat ctg ggc gcc gac atg gtg aag acc acc gtc | 576 |
|---|---|
| Val Asn Val Ala Ala Asp Leu Gly Ala Asp Met Val Lys Thr Thr Val | |
|             180                 185                 190 | |

```
gcc ctg ccg ctg gaa cgg atg tcc gag gtg gtg gcc cac agc ccc atc     624
Ala Leu Pro Leu Glu Arg Met Ser Glu Val Val Ala His Ser Pro Ile
        195                 200                 205 ccc gtc ctc gcg gcc ggt ggc ccg ccg gac ggc tcc gac ctg atc gag     672
Pro Val Leu Ala Ala Gly Gly Pro Pro Asp Gly Ser Asp Leu Ile Glu
    210                 215                 220 tac ggc acc gcc gtg atg gcg gcc ggc tgc cgg gga ctc gcc gtc ggc     720
Tyr Gly Thr Ala Val Met Ala Ala Gly Cys Arg Gly Leu Ala Val Gly
225                 230                 235                 240 cgt cgg gtc ttc tcc tcc ccc tcc ccc acc tcc ctg gtc tcc cgc ctc     768
Arg Arg Val Phe Ser Ser Pro Ser Pro Thr Ser Leu Val Ser Arg Leu
                245                 250                 255 gcc gcg gtg gtg cac ggc acc gcc ggc gac ggc ctc ccg gac ggc agg     816
Ala Ala Val Val His Gly Thr Ala Gly Asp Gly Leu Pro Asp Gly Arg
            260                 265                 270 ggc atg tcc aac cag tcc tct tcc tct tcc cgt tac tcg acg atc gtg     864
Gly Met Ser Asn Gln Ser Ser Ser Ser Ser Arg Tyr Ser Thr Ile Val
        275                 280                 285 gca ggt gtc gca tga                                                 879
Ala Gly Val Ala
    290
```

<210> SEQ ID NO 15
<211> LENGTH: 292
<212> TYPE: PRT
<213> ORGANISM: Streptomyces scabies

<400> SEQUENCE: 15

```
Met Gln Pro Arg Ser Trp Glu Gly Ala Leu Pro Met Leu Lys Thr Gly
1               5                   10                  15

Lys Pro Leu Arg Trp Arg Arg Leu Ser Arg Ala Gly Asp Asp Arg His
            20                  25                  30

Leu Leu Ile Pro Leu Asp His Ser Val Ser Asp Gly Pro Val Ala Pro
        35                  40                  45

Pro Gly Arg Trp Glu Asp Leu Leu Arg Glu Leu Val Ala Gly Gly Ala
    50                  55                  60

Asp Gly Ile Val Val His Lys Gly Arg Ala Arg Thr Leu Ala Pro Asp
65                  70                  75                  80

Leu Leu Gly Asp Cys Ala Leu Val Val His Leu Ser Ala Ser Thr Ala
                85                  90                  95

Cys Ser Ala Asp Val Asp Ala Lys Val Leu Val Gly Asp Val Glu Glu
            100                 105                 110

Ala Val Ala Leu Gly Ala Asp Ala Val Ser Val His Val Asn Ile Gly
        115                 120                 125

Ser Asp Thr Glu Gly Arg Gln Leu Ala Asp Leu Gly Ala Val Ala Arg
    130                 135                 140

Ser Cys Asp Thr Trp Gly Met Pro Leu Ile Ala Met Val Tyr Pro Arg
145                 150                 155                 160

Gly Pro Arg Ile Glu Asn Pro His Asp Pro Ala Leu Leu Ala His Val
                165                 170                 175

Val Asn Val Ala Ala Asp Leu Gly Ala Asp Met Val Lys Thr Thr Val
            180                 185                 190

Ala Leu Pro Leu Glu Arg Met Ser Glu Val Val Ala His Ser Pro Ile
        195                 200                 205

Pro Val Leu Ala Ala Gly Gly Pro Pro Asp Gly Ser Asp Leu Ile Glu
    210                 215                 220

Tyr Gly Thr Ala Val Met Ala Ala Gly Cys Arg Gly Leu Ala Val Gly
```

```
                    225                 230                 235                 240
Arg Arg Val Phe Ser Ser Pro Ser Pro Thr Ser Leu Val Ser Arg Leu
                        245                 250                 255

Ala Ala Val Val His Gly Thr Ala Gly Asp Gly Leu Pro Asp Gly Arg
                260                 265                 270

Gly Met Ser Asn Gln Ser Ser Ser Ser Arg Tyr Ser Thr Ile Val
            275                 280                 285

Ala Gly Val Ala
        290

<210> SEQ ID NO 16
<211> LENGTH: 801
<212> TYPE: DNA
<213> ORGANISM: Burkholderia sp.
<220> FEATURE:
<221> NAME/KEY: CDS
<222> LOCATION: (1)..(801)

<400> SEQUENCE: 16 atg aac gct ctt cta tcg gtt tct ggc aag gcg ctc agg atg cgg cgg      48
Met Asn Ala Leu Leu Ser Val Ser Gly Lys Ala Leu Arg Met Arg Arg
1               5                   10                  15 gtg gtg cgt gcc gcg tcg ggc aag tgc ctg atg gtg ccg ctc gat cat      96
Val Val Arg Ala Ala Ser Gly Lys Cys Leu Met Val Pro Leu Asp His
                20                  25                  30 tcg ctc gcg gac ggg ccc atc gcc cat ccg cag cag ttg cgg caa ctg     144
Ser Leu Ala Asp Gly Pro Ile Ala His Pro Gln Gln Leu Arg Gln Leu
            35                  40                  45 gtt ggc gac atc gcc gtg cat ggc ggc gat gcg atc gtc gtg cat cgc     192
Val Gly Asp Ile Ala Val His Gly Gly Asp Ala Ile Val Val His Arg
        50                  55                  60 ggc cgc gcg cgc ttc ctg tcg ccc gac gtg ctg aac gat ctc gcg ctc     240
Gly Arg Ala Arg Phe Leu Ser Pro Asp Val Leu Asn Asp Leu Ala Leu
65                  70                  75                  80 gtc gtg cac ctg aac ggc tgc acg cgc tac gcg gag gac gtg aac gcg     288
Val Val His Leu Asn Gly Cys Thr Arg Tyr Ala Glu Asp Val Asn Ala
                85                  90                  95 aag acg ctg ttc gcg agc gtc gag gat gcg ctg gca tgc ggc gcg gac     336
Lys Thr Leu Phe Ala Ser Val Glu Asp Ala Leu Ala Cys Gly Ala Asp
            100                 105                 110 gcg gtc agc gtg cac gtg aat ctc ggc tcg aag acg gaa agc cag caa     384
Ala Val Ser Val His Val Asn Leu Gly Ser Lys Thr Glu Ser Gln Gln
        115                 120                 125 ctg ctc gac ctg agc cgc atc gcg acc gag tgt gcg cgc tgg tcg ctg     432
Leu Leu Asp Leu Ser Arg Ile Ala Thr Glu Cys Ala Arg Trp Ser Leu
130                 135                 140 ccg ctg ctc gcg atg atc tat ccg cgc ggc ccg ggc ctc ggc gat cgt     480
Pro Leu Leu Ala Met Ile Tyr Pro Arg Gly Pro Gly Leu Gly Asp Arg
                150                 155                 160
145 ccg cag acc gaa ctg att gcc cac gcg gcg aac gtc gcg gcg gat ctc     528
Pro Gln Thr Glu Leu Ile Ala His Ala Ala Asn Val Ala Ala Asp Leu
            165                 170                 175 ggc gcc gac atc gtc aag ctg ccg tac agc ggc gat gcc gcg agc atg     576
Gly Ala Asp Ile Val Lys Leu Pro Tyr Ser Gly Asp Ala Ala Ser Met
        180                 185                 190 gcc gac atc atc gcc ggc tcg tcg ctg ccg gtg ctg gtc gcg ggc ggc     624
Ala Asp Ile Ile Ala Gly Ser Ser Leu Pro Val Leu Val Ala Gly Gly
    195                 200                 205 gcg aag ctg ccg gaa gac gag ttc gtc gcg ttc acg tcg cgc gtg atg     672
Ala Lys Leu Pro Glu Asp Glu Phe Val Ala Phe Thr Ser Arg Val Met
210                 215                 220
```

```
aat gca ggt gcg ctc ggc att gca gcc ggc cgc aac gtg ttc gcc gcg      720
Asn Ala Gly Ala Leu Gly Ile Ala Ala Gly Arg Asn Val Phe Ala Ala
225             230                 235                 240 ccg aag gcc gca ccg ctg atc cgc cgc ctg tcc gat gcc gtg cac ggc      768
Pro Lys Ala Ala Pro Leu Ile Arg Arg Leu Ser Asp Ala Val His Gly
            245                 250                 255 gtc gag cgg cgt gcc gcg cac ctg gcc gcc tga                          801
Val Glu Arg Arg Ala Ala His Leu Ala Ala
        260                 265
```

<210> SEQ ID NO 17
<211> LENGTH: 266
<212> TYPE: PRT
<213> ORGANISM: Burkholderia sp.

<400> SEQUENCE: 17

```
Met Asn Ala Leu Leu Ser Val Ser Gly Lys Ala Leu Arg Met Arg Arg
1               5                   10                  15

Val Val Arg Ala Ala Ser Gly Lys Cys Leu Met Val Pro Leu Asp His
                20                  25                  30

Ser Leu Ala Asp Gly Pro Ile Ala His Pro Gln Gln Leu Arg Gln Leu
            35                  40                  45

Val Gly Asp Ile Ala Val His Gly Gly Asp Ala Ile Val His Arg
        50                  55                  60

Gly Arg Ala Arg Phe Leu Ser Pro Asp Val Leu Asn Asp Leu Ala Leu
65                  70                  75                  80

Val Val His Leu Asn Gly Cys Thr Arg Tyr Ala Glu Asp Val Asn Ala
                85                  90                  95

Lys Thr Leu Phe Ala Ser Val Glu Asp Ala Leu Ala Cys Gly Ala Asp
            100                 105                 110

Ala Val Ser Val His Val Asn Leu Gly Ser Lys Thr Glu Ser Gln Gln
        115                 120                 125

Leu Leu Asp Leu Ser Arg Ile Ala Thr Glu Cys Ala Arg Trp Ser Leu
130                 135                 140

Pro Leu Leu Ala Met Ile Tyr Pro Arg Gly Pro Gly Leu Gly Asp Arg
145                 150                 155                 160

Pro Gln Thr Glu Leu Ile Ala His Ala Ala Asn Val Ala Ala Asp Leu
                165                 170                 175

Gly Ala Asp Ile Val Lys Leu Pro Tyr Ser Gly Asp Ala Ala Ser Met
            180                 185                 190

Ala Asp Ile Ile Ala Gly Ser Ser Leu Pro Val Leu Val Ala Gly Gly
        195                 200                 205

Ala Lys Leu Pro Glu Asp Glu Phe Val Ala Phe Thr Ser Arg Val Met
210                 215                 220

Asn Ala Gly Ala Leu Gly Ile Ala Ala Gly Arg Asn Val Phe Ala Ala
225                 230                 235                 240

Pro Lys Ala Ala Pro Leu Ile Arg Arg Leu Ser Asp Ala Val His Gly
                245                 250                 255

Val Glu Arg Arg Ala Ala His Leu Ala Ala
            260                 265
```

<210> SEQ ID NO 18
<211> LENGTH: 822
<212> TYPE: DNA
<213> ORGANISM: Methanococcus jannaschii
<220> FEATURE:
<221> NAME/KEY: CDS
<222> LOCATION: (1)..(822)

<400> SEQUENCE: 18

```
atg gaa tta ttt aaa gac ata aag aat ctt gga aaa ctt gta agg ttg      48
Met Glu Leu Phe Lys Asp Ile Lys Asn Leu Gly Lys Leu Val Arg Leu
1               5                   10                  15 gag aga ata ttt aac aga gaa agt gaa aaa act gta att gtt cca atg      96
Glu Arg Ile Phe Asn Arg Glu Ser Glu Lys Thr Val Ile Val Pro Met
            20                  25                  30 gac cat ggg gta tca aac ggt cca att aag ggg ctt ata gat ata aga     144
Asp His Gly Val Ser Asn Gly Pro Ile Lys Gly Leu Ile Asp Ile Arg
        35                  40                  45 aaa acc gta aat gat gtt gcc gaa gga gga gct aat gct gtc ctc tta     192
Lys Thr Val Asn Asp Val Ala Glu Gly Gly Ala Asn Ala Val Leu Leu
    50                  55                  60 cat aag gga att gta aga cat gga cac aga gga tat ggc aaa gat gtt     240
His Lys Gly Ile Val Arg His Gly His Arg Gly Tyr Gly Lys Asp Val
65                  70                  75                  80 ggt tta atc atc cat ctc tct ggt gga act gca ata tca cca aat cca     288
Gly Leu Ile Ile His Leu Ser Gly Gly Thr Ala Ile Ser Pro Asn Pro
                85                  90                  95 ttg aag aag gtt att gtt aca act gtt gaa gaa gct atc aga atg ggt     336
Leu Lys Lys Val Ile Val Thr Thr Val Glu Glu Ala Ile Arg Met Gly
            100                 105                 110 gct gat gct gtc tca att cac gta aat gtt ggt tca gat gaa gat tgg     384
Ala Asp Ala Val Ser Ile His Val Asn Val Gly Ser Asp Glu Asp Trp
        115                 120                 125 gaa gca tac aga gat ttg ggg atg ata gct gaa aca tgt gaa tac tgg     432
Glu Ala Tyr Arg Asp Leu Gly Met Ile Ala Glu Thr Cys Glu Tyr Trp
    130                 135                 140 gga atg ccg tta att gct atg atg tat cca aga gga aaa cac att caa     480
Gly Met Pro Leu Ile Ala Met Met Tyr Pro Arg Gly Lys His Ile Gln
145                 150                 155                 160 aat gag aga gac cct gaa tta gtt gct cat gca gca aga ttg gga gct     528
Asn Glu Arg Asp Pro Glu Leu Val Ala His Ala Ala Arg Leu Gly Ala
                165                 170                 175 gag tta gga gct gac ata gtt aaa aca agt tat act gga gat att gat     576
Glu Leu Gly Ala Asp Ile Val Lys Thr Ser Tyr Thr Gly Asp Ile Asp
            180                 185                 190 tca ttt aga gat gtt gtt aag ggt tgt cca gct cca gtt gtg gtt gct     624
Ser Phe Arg Asp Val Val Lys Gly Cys Pro Ala Pro Val Val Val Ala
        195                 200                 205 gga ggg cca aag aca aac aca gat gaa gag ttc ttg caa atg att aaa     672
Gly Gly Pro Lys Thr Asn Thr Asp Glu Glu Phe Leu Gln Met Ile Lys
    210                 215                 220 gat gct atg gag gct gga gct gct ggt gtt gca gtg ggt aga aat atc     720
Asp Ala Met Glu Ala Gly Ala Ala Gly Val Ala Val Gly Arg Asn Ile
225                 230                 235                 240 ttc cag cat gat gat gtt gtt ggc ata aca aga gct gtt tgt aag ata     768
Phe Gln His Asp Asp Val Val Gly Ile Thr Arg Ala Val Cys Lys Ile
                245                 250                 255 gtc cat gaa aat gca gac gtt gag gag gcg tta aaa gag att agg aag     816
Val His Glu Asn Ala Asp Val Glu Glu Ala Leu Lys Glu Ile Arg Lys
            260                 265                 270 aaa taa                                                             822
Lys
```

<210> SEQ ID NO 19
<211> LENGTH: 273
<212> TYPE: PRT
<213> ORGANISM: Methanococcus jannaschii

<400> SEQUENCE: 19

```
Met Glu Leu Phe Lys Asp Ile Lys Asn Leu Gly Lys Leu Val Arg Leu
1               5                   10                  15

Glu Arg Ile Phe Asn Arg Glu Ser Lys Thr Val Ile Val Pro Met
            20                  25                  30

Asp His Gly Val Ser Asn Gly Pro Ile Lys Gly Leu Ile Asp Ile Arg
            35                  40                  45

Lys Thr Val Asn Asp Val Ala Glu Gly Gly Ala Asn Ala Val Leu Leu
50                  55                  60

His Lys Gly Ile Val Arg His Gly His Arg Gly Tyr Gly Lys Asp Val
65                  70                  75                  80

Gly Leu Ile Ile His Leu Ser Gly Gly Thr Ala Ile Ser Pro Asn Pro
                85                  90                  95

Leu Lys Lys Val Ile Val Thr Thr Val Glu Ala Ile Arg Met Gly
            100                 105                 110

Ala Asp Ala Val Ser Ile His Val Asn Val Gly Ser Asp Glu Asp Trp
            115                 120                 125

Glu Ala Tyr Arg Asp Leu Gly Met Ile Ala Glu Thr Cys Glu Tyr Trp
130                 135                 140

Gly Met Pro Leu Ile Ala Met Met Tyr Pro Arg Gly Lys His Ile Gln
145                 150                 155                 160

Asn Glu Arg Asp Pro Glu Leu Val Ala His Ala Arg Leu Gly Ala
            165                 170                 175

Glu Leu Gly Ala Asp Ile Val Lys Thr Ser Tyr Thr Gly Asp Ile Asp
            180                 185                 190

Ser Phe Arg Asp Val Val Lys Gly Cys Pro Ala Pro Val Val Ala
            195                 200                 205

Gly Gly Pro Lys Thr Asn Thr Asp Glu Glu Phe Leu Gln Met Ile Lys
210                 215                 220

Asp Ala Met Glu Ala Gly Ala Ala Gly Val Ala Val Gly Arg Asn Ile
225                 230                 235                 240

Phe Gln His Asp Asp Val Val Gly Ile Thr Arg Ala Val Cys Lys Ile
            245                 250                 255

Val His Glu Asn Ala Asp Val Glu Glu Ala Leu Lys Glu Ile Arg Lys
            260                 265                 270

Lys
```

<210> SEQ ID NO 20
<211> LENGTH: 1053
<212> TYPE: DNA
<213> ORGANISM: Escherichia coli
<220> FEATURE:
<221> NAME/KEY: CDS
<222> LOCATION: (1)..(1053)

<400> SEQUENCE: 20

```
atg aca gat att gcg cag ttg ctt ggc aaa gac gcc gac aac ctt tta     48
Met Thr Asp Ile Ala Gln Leu Leu Gly Lys Asp Ala Asp Asn Leu Leu
1               5                   10                  15 cag cac cgt tgt atg aca att cct tct gac cag ctt tat ctc ccc gga     96
Gln His Arg Cys Met Thr Ile Pro Ser Asp Gln Leu Tyr Leu Pro Gly
            20                  25                  30 cat gac tac gta gac cgc gta atg att gac aat aat cgc ccg cca gcg    144
His Asp Tyr Val Asp Arg Val Met Ile Asp Asn Asn Arg Pro Pro Ala
            35                  40                  45 gtg tta cgt aat atg cag acg ttg tac aac acc ggg cgt ctg gct ggc    192
Val Leu Arg Asn Met Gln Thr Leu Tyr Asn Thr Gly Arg Leu Ala Gly
```

```
              50                  55                  60
aca gga tat ctt tct att ctg ccg gtt gac cag ggc gtt gag cac tct     240
Thr Gly Tyr Leu Ser Ile Leu Pro Val Asp Gln Gly Val Glu His Ser
 65                  70                  75                  80 gcc gga gct tca ttt gct gct aac ccg ctc tac ttt gac ccg aaa aac     288
Ala Gly Ala Ser Phe Ala Ala Asn Pro Leu Tyr Phe Asp Pro Lys Asn
                 85                  90                  95 att gtt gaa ctg gcg atc gaa gcg ggc tgt aac tgt gtg gcg tca act     336
Ile Val Glu Leu Ala Ile Glu Ala Gly Cys Asn Cys Val Ala Ser Thr
            100                 105                 110 tac ggc gtg ctg gcg tcg gta tcg cgg cgt tat gcg cat cgc att cca     384
Tyr Gly Val Leu Ala Ser Val Ser Arg Arg Tyr Ala His Arg Ile Pro
        115                 120                 125 ttc ctc gtc aaa ctt aat cac aac gag acg cta agt tac ccg aat acc     432
Phe Leu Val Lys Leu Asn His Asn Glu Thr Leu Ser Tyr Pro Asn Thr
    130                 135                 140 tac gat caa acg ctg tat gcc agc gtg gag cag gcg ttc aac atg ggc     480
Tyr Asp Gln Thr Leu Tyr Ala Ser Val Glu Gln Ala Phe Asn Met Gly
145                 150                 155                 160 gcg gtt gcg gtt ggt gcg act atc tat ttt ggc tcg gaa gag tca cgt     528
Ala Val Ala Val Gly Ala Thr Ile Tyr Phe Gly Ser Glu Glu Ser Arg
                165                 170                 175 cgc cag att gaa gaa att tct gcg gct ttt gaa cgt gcg cac gag ctg     576
Arg Gln Ile Glu Glu Ile Ser Ala Ala Phe Glu Arg Ala His Glu Leu
            180                 185                 190 ggt atg gtg aca gtg ctg tgg gcc tat ttg cgt aac tcc gcc ttt aag     624
Gly Met Val Thr Val Leu Trp Ala Tyr Leu Arg Asn Ser Ala Phe Lys
        195                 200                 205 aaa gat ggc gtt gat tac cat gtt tcc gcc gac ctg acc ggt cag gca     672
Lys Asp Gly Val Asp Tyr His Val Ser Ala Asp Leu Thr Gly Gln Ala
    210                 215                 220 aac cat ctg gcg gca acc atc ggt gca gat atc gtc aaa caa aaa atg     720
Asn His Leu Ala Ala Thr Ile Gly Ala Asp Ile Val Lys Gln Lys Met
225                 230                 235                 240 gcg gaa aat aac ggc ggc tat aaa gca att aat tac ggt tac acc gac     768
Ala Glu Asn Asn Gly Gly Tyr Lys Ala Ile Asn Tyr Gly Tyr Thr Asp
                245                 250                 255 gat cgt gtt tac agc aaa ttg acc agc gaa aac ccg att gat ctg gtg     816
Asp Arg Val Tyr Ser Lys Leu Thr Ser Glu Asn Pro Ile Asp Leu Val
            260                 265                 270 cgt tat cag tta gct aac tgc tat atg ggt cgg gct ggg ttg ata aac     864
Arg Tyr Gln Leu Ala Asn Cys Tyr Met Gly Arg Ala Gly Leu Ile Asn
        275                 280                 285 tcc ggc ggt gct gcg ggc ggt gaa act gac ctc agc gat gca gtg cgt     912
Ser Gly Gly Ala Ala Gly Gly Glu Thr Asp Leu Ser Asp Ala Val Arg
    290                 295                 300 act gcg gtt atc aac aaa cgc gca ggc gga atg ggg ctg att ctt gga     960
Thr Ala Val Ile Asn Lys Arg Ala Gly Gly Met Gly Leu Ile Leu Gly
305                 310                 315                 320 cgt aaa gcg ttc aag aaa tcg atg gct gac ggc gtg aaa ctg att aac    1008
Arg Lys Ala Phe Lys Lys Ser Met Ala Asp Gly Val Lys Leu Ile Asn
                325                 330                 335 gcc gtg cag gac gtt tat ctc gat agc aaa att act atc gcc tga        1053
Ala Val Gln Asp Val Tyr Leu Asp Ser Lys Ile Thr Ile Ala
            340                 345                 350

<210> SEQ ID NO 21
<211> LENGTH: 350
<212> TYPE: PRT
<213> ORGANISM: Escherichia coli
```

```
<400> SEQUENCE: 21

Met Thr Asp Ile Ala Gln Leu Leu Gly Lys Asp Ala Asp Asn Leu Leu
1               5                   10                  15

Gln His Arg Cys Met Thr Ile Pro Ser Asp Gln Leu Tyr Leu Pro Gly
            20                  25                  30

His Asp Tyr Val Asp Arg Val Met Ile Asp Asn Asn Arg Pro Pro Ala
        35                  40                  45

Val Leu Arg Asn Met Gln Thr Leu Tyr Asn Thr Gly Arg Leu Ala Gly
    50                  55                  60

Thr Gly Tyr Leu Ser Ile Leu Pro Val Asp Gln Gly Val Glu His Ser
65                  70                  75                  80

Ala Gly Ala Ser Phe Ala Ala Asn Pro Leu Tyr Phe Asp Pro Lys Asn
                85                  90                  95

Ile Val Glu Leu Ala Ile Glu Ala Gly Cys Asn Cys Val Ala Ser Thr
            100                 105                 110

Tyr Gly Val Leu Ala Ser Val Ser Arg Arg Tyr Ala His Arg Ile Pro
        115                 120                 125

Phe Leu Val Lys Leu Asn His Asn Glu Thr Leu Ser Tyr Pro Asn Thr
    130                 135                 140

Tyr Asp Gln Thr Leu Tyr Ala Ser Val Glu Gln Ala Phe Asn Met Gly
145                 150                 155                 160

Ala Val Ala Val Gly Ala Thr Ile Tyr Phe Gly Ser Glu Glu Ser Arg
                165                 170                 175

Arg Gln Ile Glu Glu Ile Ser Ala Ala Phe Glu Arg Ala His Glu Leu
            180                 185                 190

Gly Met Val Thr Val Leu Trp Ala Tyr Leu Arg Asn Ser Ala Phe Lys
        195                 200                 205

Lys Asp Gly Val Asp Tyr His Val Ser Ala Asp Leu Thr Gly Gln Ala
    210                 215                 220

Asn His Leu Ala Ala Thr Ile Gly Ala Asp Ile Val Lys Gln Lys Met
225                 230                 235                 240

Ala Glu Asn Asn Gly Gly Tyr Lys Ala Ile Asn Tyr Gly Tyr Thr Asp
                245                 250                 255

Asp Arg Val Tyr Ser Lys Leu Thr Ser Glu Asn Pro Ile Asp Leu Val
            260                 265                 270

Arg Tyr Gln Leu Ala Asn Cys Tyr Met Gly Arg Ala Gly Leu Ile Asn
        275                 280                 285

Ser Gly Gly Ala Ala Gly Gly Glu Thr Asp Leu Ser Asp Ala Val Arg
    290                 295                 300

Thr Ala Val Ile Asn Lys Arg Ala Gly Gly Met Gly Leu Ile Leu Gly
305                 310                 315                 320

Arg Lys Ala Phe Lys Lys Ser Met Ala Asp Gly Val Lys Leu Ile Asn
                325                 330                 335

Ala Val Gln Asp Val Tyr Leu Asp Ser Lys Ile Thr Ile Ala
            340                 345                 350

<210> SEQ ID NO 22
<211> LENGTH: 1191
<212> TYPE: DNA
<213> ORGANISM: Streptomyces griseus
<220> FEATURE:
<221> NAME/KEY: CDS
<222> LOCATION: (1)..(1191)

<400> SEQUENCE: 22 atg tct tcg tct ccg tct ccg tct ccg tcc tcg tcg tcc tcg tca tct      48
```

```
                Met Ser Ser Ser Pro Ser Pro Ser Pro Ser Ser Ser Ser Ser Ser
                1               5               10                  15 gcg tcc tcg tcg gct tcg tcg tcg cct tcg tcg tcg aag ctg acc              96
Ala Ser Ser Ser Ala Ser Ser Ser Pro Ser Ser Ser Lys Leu Thr
            20              25              30 tgg ctc gac atc cgt tcc gtg ggc gag gcc cgt gcc gcc atc gtc cag         144
Trp Leu Asp Ile Arg Ser Val Gly Glu Ala Arg Ala Ala Ile Val Gln
        35              40              45 gag gcc ctg cac cac cgg gtg gaa gcg ctg gtc gcc gac gac ccc gcc         192
Glu Ala Leu His His Arg Val Glu Ala Leu Val Ala Asp Asp Pro Ala
    50              55              60 cac ctc gcg gac ctg ccg ccc acc gtg gcc aag gtc ctg ctg gtg gtg         240
His Leu Ala Asp Leu Pro Pro Thr Val Ala Lys Val Leu Leu Val Val
65              70              75              80 ggg aag cag atc ccg gag gag ttc ggc gag gcg acg gtc gtc gtc gtc         288
Gly Lys Gln Ile Pro Glu Glu Phe Gly Glu Ala Thr Val Val Val Val
            85              90              95 gac ccg tcg aag cac ggt gtg acc ccc gcc gaa ctg gcg ctc aag cac         336
Asp Pro Ser Lys His Gly Val Thr Pro Ala Glu Leu Ala Leu Lys His
        100             105             110 ccg gag atc gag ttc ggg cgg ttc gtg gag atc atc gac gcg ccg acg         384
Pro Glu Ile Glu Phe Gly Arg Phe Val Glu Ile Ile Asp Ala Pro Thr
    115             120             125 ctg gag gac gcc tgc gag tcc tcg cgg acc gag aag tgg tcc gtc ctg         432
Leu Glu Asp Ala Cys Glu Ser Ser Arg Thr Glu Lys Trp Ser Val Leu
130             135             140 ctg ttc cgc gac ccg acc aag atc ccg ctg gag atc gtg atc gcc gcc         480
Leu Phe Arg Asp Pro Thr Lys Ile Pro Leu Glu Ile Val Ile Ala Ala
145             150             155             160 gcc gcg cgc gcc tcc ggt tcg atg gtg acc atc gcg cag gac ctg gag         528
Ala Ala Arg Ala Ser Gly Ser Met Val Thr Ile Ala Gln Asp Leu Glu
            165             170             175 gag gcg gag atc ctc ttc ggc gtg ctg gag cac ggc tcg gac ggc gtg         576
Glu Ala Glu Ile Leu Phe Gly Val Leu Glu His Gly Ser Asp Gly Val
        180             185             190 atg atg gcc ccg aag acg gtc ggt gac gcc gcc gag ctg aag cgg atc         624
Met Met Ala Pro Lys Thr Val Gly Asp Ala Ala Glu Leu Lys Arg Ile
    195             200             205 gcc gag gcc ggc atc ccc aac ctc aac ctc acc gag ctg cgc gtc gtg         672
Ala Glu Ala Gly Ile Pro Asn Leu Asn Leu Thr Glu Leu Arg Val Val
210             215             220 gag acc agc cac atc ggc atg ggc gag cgg gcc tgc gtg gac acc acc         720
Glu Thr Ser His Ile Gly Met Gly Glu Arg Ala Cys Val Asp Thr Thr
225             230             235             240 acg cat ttc ggc gag gac gag ggc atc ctg gtc ggc tcg cac tcc aag         768
Thr His Phe Gly Glu Asp Glu Gly Ile Leu Val Gly Ser His Ser Lys
            245             250             255 ggc atg atc ctc tgc gtc agc gag acc cac ccg ctg ccg tac atg ccg         816
Gly Met Ile Leu Cys Val Ser Glu Thr His Pro Leu Pro Tyr Met Pro
        260             265             270 acc cgg ccg ttc cgc gtc aac gcc ggc gcc atc cac tcg tac acg ctg         864
Thr Arg Pro Phe Arg Val Asn Ala Gly Ala Ile His Ser Tyr Thr Leu
    275             280             285 ggc agg gac gag cgc acg aac tac ctg agc gaa ctg aag acg ggc agc         912
Gly Arg Asp Glu Arg Thr Asn Tyr Leu Ser Glu Leu Lys Thr Gly Ser
290             295             300 aag ctc acc gcc gtc gac atc aag ggc aac acc cgg ctg gtg acc gtg         960
Lys Leu Thr Ala Val Asp Ile Lys Gly Asn Thr Arg Leu Val Thr Val
305             310             315             320 ggc cgc gtg aag atc gag acc cgc ccg ctg atc tcc atc gac gcc gag        1008
```

```
Gly Arg Val Lys Ile Glu Thr Arg Pro Leu Ile Ser Ile Asp Ala Glu
                325                 330                 335 gcc ccg gac ggc cgg cgc gtc aac ctg atc ctc cag gac gac tgg cac      1056
Ala Pro Asp Gly Arg Arg Val Asn Leu Ile Leu Gln Asp Asp Trp His
                340                 345                 350 gtc cgg gtc ctc ggc ccc ggt ggc acg gtc ctc aac agc acc gag ctg      1104
Val Arg Val Leu Gly Pro Gly Gly Thr Val Leu Asn Ser Thr Glu Leu
                355                 360                 365 aag ccc ggc gac acg gtc ctc ggc tac ctg ccc gtc gag gac cgt cac      1152
Lys Pro Gly Asp Thr Val Leu Gly Tyr Leu Pro Val Glu Asp Arg His
                370                 375                 380 gtc ggc tac ccg atc aac gag ttc tgc ctg gag aag tag                  1191
Val Gly Tyr Pro Ile Asn Glu Phe Cys Leu Glu Lys
385                 390                 395

<210> SEQ ID NO 23
<211> LENGTH: 396
<212> TYPE: PRT
<213> ORGANISM: Streptomyces griseus

<400> SEQUENCE: 23

Met Ser Ser Pro Ser Pro Ser Pro Ser Ser Ser Ser Ser Ser Ser Ser
1               5                   10                  15

Ala Ser Ser Ala Ser Ser Ser Pro Ser Ser Ser Lys Leu Thr
                20                  25                  30

Trp Leu Asp Ile Arg Ser Val Gly Glu Ala Arg Ala Ala Ile Val Gln
            35                  40                  45

Glu Ala Leu His His Arg Val Glu Ala Leu Val Ala Asp Asp Pro Ala
        50                  55                  60

His Leu Ala Asp Leu Pro Pro Thr Val Ala Lys Val Leu Leu Val Val
65                  70                  75                  80

Gly Lys Gln Ile Pro Glu Glu Phe Gly Glu Ala Thr Val Val Val
                85                  90                  95

Asp Pro Ser Lys His Gly Val Thr Pro Ala Glu Leu Ala Leu Lys His
                100                 105                 110

Pro Glu Ile Glu Phe Gly Arg Phe Val Glu Ile Ile Asp Ala Pro Thr
            115                 120                 125

Leu Glu Asp Ala Cys Glu Ser Ser Arg Thr Glu Lys Trp Ser Val Leu
    130                 135                 140

Leu Phe Arg Asp Pro Thr Lys Ile Pro Leu Glu Ile Val Ile Ala Ala
145                 150                 155                 160

Ala Ala Arg Ala Ser Gly Ser Met Val Thr Ile Ala Gln Asp Leu Glu
                165                 170                 175

Glu Ala Glu Ile Leu Phe Gly Val Leu Glu His Gly Ser Asp Gly Val
            180                 185                 190

Met Met Ala Pro Lys Thr Val Gly Asp Ala Ala Glu Leu Lys Arg Ile
        195                 200                 205

Ala Glu Ala Gly Ile Pro Asn Leu Asn Leu Thr Glu Leu Arg Val Val
    210                 215                 220

Glu Thr Ser His Ile Gly Met Gly Glu Arg Ala Cys Val Asp Thr Thr
225                 230                 235                 240

Thr His Phe Gly Glu Asp Glu Gly Ile Leu Val Gly Ser His Ser Lys
                245                 250                 255

Gly Met Ile Leu Cys Val Ser Glu Thr His Pro Leu Pro Tyr Met Pro
            260                 265                 270

Thr Arg Pro Phe Arg Val Asn Ala Gly Ala Ile His Ser Tyr Thr Leu
    275                 280                 285
```

```
Gly Arg Asp Glu Arg Thr Asn Tyr Leu Ser Glu Leu Lys Thr Gly Ser
        290                 295                 300

Lys Leu Thr Ala Val Asp Ile Lys Gly Asn Thr Arg Leu Val Thr Val
305                 310                 315                 320

Gly Arg Val Lys Ile Glu Thr Arg Pro Leu Ile Ser Ile Asp Ala Glu
                325                 330                 335

Ala Pro Asp Gly Arg Arg Val Asn Leu Ile Leu Gln Asp Asp Trp His
            340                 345                 350

Val Arg Val Leu Gly Pro Gly Thr Val Leu Asn Ser Thr Glu Leu
        355                 360                 365

Lys Pro Gly Asp Thr Val Leu Gly Tyr Leu Pro Val Glu Asp Arg His
    370                 375                 380

Val Gly Tyr Pro Ile Asn Glu Phe Cys Leu Glu Lys
385                 390                 395

<210> SEQ ID NO 24
<211> LENGTH: 1101
<212> TYPE: DNA
<213> ORGANISM: Frankia sp.
<220> FEATURE:
<221> NAME/KEY: CDS
<222> LOCATION: (1)..(1101)

<400> SEQUENCE: 24 atg aaa ctg tac tgg gtt gag atc cat ggc gct gga ccg ctc ttg acc      48
Met Lys Leu Tyr Trp Val Glu Ile His Gly Ala Gly Pro Leu Leu Thr
1               5                   10                  15 gcg gtc gcg gag gag gcg att cac cag agg gtc gac gcc gtc gtc tcc     96
Ala Val Ala Glu Glu Ala Ile His Gln Arg Val Asp Ala Val Val Ser
            20                  25                  30 gac gat ccc gcc aac ctg tcc acg ttg ccg ccg acg gtc aag aag gtt    144
Asp Asp Pro Ala Asn Leu Ser Thr Leu Pro Pro Thr Val Lys Lys Val
        35                  40                  45 ctg ctg acc aag gac ggc tcc ctg ggc gaa gac ctg gac ggc gtt gat    192
Leu Leu Thr Lys Asp Gly Ser Leu Gly Glu Asp Leu Asp Gly Val Asp
    50                  55                  60 gtc gtc atc ctc gat gcc gaa cgg gag cgg att cac gag ctg tca gct    240
Val Val Ile Leu Asp Ala Glu Arg Glu Arg Ile His Glu Leu Ser Ala
65                  70                  75                  80 acc tac ccg cac gtc gag ttc ggc agg tat ctc gag gtg acc gat gcg    288
Thr Tyr Pro His Val Glu Phe Gly Arg Tyr Leu Glu Val Thr Asp Ala
                85                  90                  95 cag acg ctc gat gcc gcc tgc gca gcc gcc cag gaa tgg gcg tgg acc    336
Gln Thr Leu Asp Ala Ala Cys Ala Ala Ala Gln Glu Trp Ala Trp Thr
            100                 105                 110 gtc ctc cgg ttc cgc gac gag acg aag atc ccg ctg gag atc gtc ctg    384
Val Leu Arg Phe Arg Asp Glu Thr Lys Ile Pro Leu Glu Ile Val Leu
        115                 120                 125 gcc gcg gcg cac aag tcc cag ggc agc gtg atc acc gtt gtt cac gac    432
Ala Ala Ala His Lys Ser Gln Gly Ser Val Ile Thr Val Val His Asp
    130                 135                 140 acg gac gag gcc aac gtc gtg ctc ggc tgc ctg gag cgt ggc gcc gac    480
Thr Asp Glu Ala Asn Val Val Leu Gly Cys Leu Glu Arg Gly Ala Asp
145                 150                 155                 160 ggc atc atg ctg gcg ccg aag gct gtc ggc gag ttg tcc gcg ctt aag    528
Gly Ile Met Leu Ala Pro Lys Ala Val Gly Glu Leu Ser Ala Leu Lys
                165                 170                 175 gcc gtg gcc gcc ggg ggt tcc ttc tcg ctc cag ctc gag gaa ctg gaa    576
Ala Val Ala Ala Gly Gly Ser Phe Ser Leu Gln Leu Glu Glu Leu Glu
            180                 185                 190
```

```
gtc atc gag acc agt cat gtg gga atg ggc gag cgg gcc tgc gtc gac    624
Val Ile Glu Thr Ser His Val Gly Met Gly Glu Arg Ala Cys Val Asp
        195                 200                 205 acc tgc agc atg ttc ggc gag aac gag gga atc cta gtg ggc tca cac    672
Thr Cys Ser Met Phe Gly Glu Asn Glu Gly Ile Leu Val Gly Ser His
210                 215                 220 tcc aag gga atg atc ctt gcg tgc agc gag acg cat cca ctg ccc tac    720
Ser Lys Gly Met Ile Leu Ala Cys Ser Glu Thr His Pro Leu Pro Tyr
225                 230                 235                 240 atg ccg aca cgg ccg ttt cgg gta aac gcc ggc gcg gtt cat tcc tac    768
Met Pro Thr Arg Pro Phe Arg Val Asn Ala Gly Ala Val His Ser Tyr
                245                 250                 255 acg atg tcg atg gcc ggc cgc acc aac tac ctc agc gag cta cag gcg    816
Thr Met Ser Met Ala Gly Arg Thr Asn Tyr Leu Ser Glu Leu Gln Ala
        260                 265                 270 ggc gga aga gtg ctg gcc gtc gac gcg gac ggc cgc gct cgg ccg gtg    864
Gly Gly Arg Val Leu Ala Val Asp Ala Asp Gly Arg Ala Arg Pro Val
    275                 280                 285 acc gtc ggc cgg atc aag atc gag acg cga cct ctt cga atg atc acc    912
Thr Val Gly Arg Ile Lys Ile Glu Thr Arg Pro Leu Arg Met Ile Thr
290                 295                 300 gcg aag tcc ccg tcc ggc cga gtg gca gat ctc atc gtc cag gac gat    960
Ala Lys Ser Pro Ser Gly Arg Val Ala Asp Leu Ile Val Gln Asp Asp
305                 310                 315                 320 tgg cac gtg cgg gtt ctc ggg ccg ggc ggc gtg gtc atc aac gtc acc   1008
Trp His Val Arg Val Leu Gly Pro Gly Gly Val Val Ile Asn Val Thr
                325                 330                 335 gag ctc caa ccg ggt aca aag gtg ctc gga tac ctg ccg gtc gaa gac   1056
Glu Leu Gln Pro Gly Thr Lys Val Leu Gly Tyr Leu Pro Val Glu Asp
        340                 345                 350 cgg cac gtc ggc tac ccg atc gac gag ttc tgc atc gaa aaa tag      1101
Arg His Val Gly Tyr Pro Ile Asp Glu Phe Cys Ile Glu Lys
    355                 360                 365

<210> SEQ ID NO 25
<211> LENGTH: 366
<212> TYPE: PRT
<213> ORGANISM: Frankia sp.

<400> SEQUENCE: 25

Met Lys Leu Tyr Trp Val Glu Ile His Gly Ala Gly Pro Leu Leu Thr
1               5                   10                  15

Ala Val Ala Glu Glu Ala Ile His Gln Arg Val Asp Ala Val Val Ser
            20                  25                  30

Asp Asp Pro Ala Asn Leu Ser Thr Leu Pro Pro Thr Val Lys Lys Val
        35                  40                  45

Leu Leu Thr Lys Asp Gly Ser Leu Gly Glu Asp Leu Asp Gly Val Asp
    50                  55                  60

Val Val Ile Leu Asp Ala Glu Arg Glu Arg Ile His Glu Leu Ser Ala
65                  70                  75                  80

Thr Tyr Pro His Val Glu Phe Gly Arg Tyr Leu Glu Val Thr Asp Ala
                85                  90                  95

Gln Thr Leu Asp Ala Ala Cys Ala Ala Ala Gln Glu Trp Ala Trp Thr
            100                 105                 110

Val Leu Arg Phe Arg Asp Glu Thr Lys Ile Pro Leu Glu Ile Val Leu
        115                 120                 125

Ala Ala Ala His Lys Ser Gln Gly Ser Val Ile Thr Val Val His Asp
    130                 135                 140
```

```
Thr Asp Glu Ala Asn Val Val Leu Gly Cys Leu Arg Gly Ala Asp
145                 150                 155                 160

Gly Ile Met Leu Ala Pro Lys Ala Val Gly Glu Leu Ser Ala Leu Lys
                165                 170                 175

Ala Val Ala Ala Gly Gly Ser Phe Ser Leu Gln Leu Glu Glu Leu Glu
            180                 185                 190

Val Ile Glu Thr Ser His Val Gly Met Gly Glu Arg Ala Cys Val Asp
        195                 200                 205

Thr Cys Ser Met Phe Gly Glu Asn Glu Gly Ile Leu Val Gly Ser His
210                 215                 220

Ser Lys Gly Met Ile Leu Ala Cys Ser Glu Thr His Pro Leu Pro Tyr
225                 230                 235                 240

Met Pro Thr Arg Pro Phe Arg Val Asn Ala Gly Ala Val His Ser Tyr
                245                 250                 255

Thr Met Ser Met Ala Gly Arg Thr Asn Tyr Leu Ser Glu Leu Gln Ala
            260                 265                 270

Gly Gly Arg Val Leu Ala Val Asp Ala Asp Gly Arg Ala Arg Pro Val
        275                 280                 285

Thr Val Gly Arg Ile Lys Ile Glu Thr Arg Pro Leu Arg Met Ile Thr
290                 295                 300

Ala Lys Ser Pro Ser Gly Arg Val Ala Asp Leu Ile Val Gln Asp Asp
305                 310                 315                 320

Trp His Val Arg Val Leu Gly Pro Gly Gly Val Val Ile Asn Val Thr
                325                 330                 335

Glu Leu Gln Pro Gly Thr Lys Val Leu Gly Tyr Leu Pro Val Glu Asp
            340                 345                 350

Arg His Val Gly Tyr Pro Ile Asp Glu Phe Cys Ile Glu Lys
        355                 360                 365

<210> SEQ ID NO 26
<211> LENGTH: 1122
<212> TYPE: DNA
<213> ORGANISM: Frankia sp.
<220> FEATURE:
<221> NAME/KEY: CDS
<222> LOCATION: (1)..(1122)

<400> SEQUENCE: 26 gtg aac gca agg aag ctg tgc tgg ctt gac atc cgc gag gcc ggc gaa      48
Met Asn Ala Arg Lys Leu Cys Trp Leu Asp Ile Arg Glu Ala Gly Glu
1               5                   10                  15 gcc cgg gcc gca gtc ctc gat gag gct gtg cac cag cgg atc gac ggc      96
Ala Arg Ala Ala Val Leu Asp Glu Ala Val His Gln Arg Ile Asp Gly
            20                  25                  30 atc gtg agc gac gat ccg gcg gac ctc ggc ggg ctg ccg ccc acg gtc     144
Ile Val Ser Asp Asp Pro Ala Asp Leu Gly Gly Leu Pro Pro Thr Val
        35                  40                  45 cgc aag ata ctt ctc tat gac ggc ccc aca gcc gaa gca cca gag act     192
Arg Lys Ile Leu Leu Tyr Asp Gly Pro Thr Ala Glu Ala Pro Glu Thr
    50                  55                  60 cct gac ctc tcg gcg gcg gac atc gtg atc ctg ccg tcc ggt ctc acg     240
Pro Asp Leu Ser Ala Ala Asp Ile Val Ile Leu Pro Ser Gly Leu Thr
65                  70                  75                  80 ggg cgc cgc gca ctg gag gag cgc cat ccc gcc gtc cag ttc ggg cgc     288
Gly Arg Arg Ala Leu Glu Glu Arg His Pro Ala Val Gln Phe Gly Arg
                85                  90                  95 cgc gtc gag atc gtt gac gcc ccg agt ctg gag gag gcg tgc gac gcg     336
Arg Val Glu Ile Val Asp Ala Pro Ser Leu Glu Glu Ala Cys Asp Ala
            100                 105                 110
```

```
gcc cat acc gag ccg tgg agc ctg ctc gac ttc cgg gac ccg acc aag       384
Ala His Thr Glu Pro Trp Ser Leu Leu Asp Phe Arg Asp Pro Thr Lys
        115                 120                 125 ata ccg ctg gag att gtg atc gct gca gcc gtg gga gcc gag ggt tcc       432
Ile Pro Leu Glu Ile Val Ile Ala Ala Ala Val Gly Ala Glu Gly Ser
    130                 135                 140 att gtc act cgc gcc gac gac gcg gtg gag gcg cag atc gtc ttc ggg       480
Ile Val Thr Arg Ala Asp Asp Ala Val Glu Ala Gln Ile Val Phe Gly
145                 150                 155                 160 gtc ctg gaa ctg gga tcc gac gga gtc atg atg ccg gga cgg gca gtg       528
Val Leu Glu Leu Gly Ser Asp Gly Val Met Met Pro Gly Arg Ala Val
                165                 170                 175 ggg gac gcg act gcc ctg aaa cgc gcc acg gag gcc gcc acc ggc gaa       576
Gly Asp Ala Thr Ala Leu Lys Arg Ala Thr Glu Ala Ala Thr Gly Glu
            180                 185                 190 ctg gag ctg gtc gaa ctg gag atc acg gcc acc acc cac atc ggc atc       624
Leu Glu Leu Val Glu Leu Glu Ile Thr Ala Thr Thr His Ile Gly Ile
        195                 200                 205 ggt gaa cgg gcg tgt gtg gac acc tgc gcc tac ctg cgc gag gac gaa       672
Gly Glu Arg Ala Cys Val Asp Thr Cys Ala Tyr Leu Arg Glu Asp Glu
    210                 215                 220 gga atc ctc gtc ggc tcg tac tcc aag ggc atg att ctc tgc gtc agc       720
Gly Ile Leu Val Gly Ser Tyr Ser Lys Gly Met Ile Leu Cys Val Ser
225                 230                 235                 240 gaa acc cat ccc ctg ccc tac atg ccg acc cgt ccg ttc cgc gtg aac       768
Glu Thr His Pro Leu Pro Tyr Met Pro Thr Arg Pro Phe Arg Val Asn
                245                 250                 255 gcc ggc gcg atc cac tcc tac acg gtt tcg gcc ggc ggc agg acc cag       816
Ala Gly Ala Ile His Ser Tyr Thr Val Ser Ala Gly Gly Arg Thr Gln
            260                 265                 270 tac ctc agc gaa ctc cac tcg ggc agc aag gtc ctg gcc gtc gac gtg       864
Tyr Leu Ser Glu Leu His Ser Gly Ser Lys Val Leu Ala Val Asp Val
        275                 280                 285 aag ggc cgg acg cgg atc gtc ccg gtc ggc cgg gtc aag atc gag aag       912
Lys Gly Arg Thr Arg Ile Val Pro Val Gly Arg Val Lys Ile Glu Lys
    290                 295                 300 cgc ccg ctc atc tcc gtg gac gcc gtg gcc gga aac ggc cga gaa gtc       960
Arg Pro Leu Ile Ser Val Asp Ala Val Ala Gly Asn Gly Arg Glu Val
305                 310                 315                 320 aat ctg att ctt cag gac gac tgg cat gtc cgt gtt ctc ggc ccc gga      1008
Asn Leu Ile Leu Gln Asp Asp Trp His Val Arg Val Leu Gly Pro Gly
                325                 330                 335 ggc gcc gtg ctc aac agc acc gaa ctc aag ccc ggc gac cgg gtg ctg      1056
Gly Ala Val Leu Asn Ser Thr Glu Leu Lys Pro Gly Asp Arg Val Leu
            340                 345                 350 ggg cat cta ccg acg gcg gac cgg cac gtc ggc tac ccg atc gac gag      1104
Gly His Leu Pro Thr Ala Asp Arg His Val Gly Tyr Pro Ile Asp Glu
        355                 360                 365 ttc tgc cgc gag cag tga                                              1122
Phe Cys Arg Glu Gln
    370

<210> SEQ ID NO 27
<211> LENGTH: 373
<212> TYPE: PRT
<213> ORGANISM: Frankia sp.

<400> SEQUENCE: 27

Met Asn Ala Arg Lys Leu Cys Trp Leu Asp Ile Arg Glu Ala Gly Glu
1               5                   10                  15
```

```
Ala Arg Ala Ala Val Leu Asp Glu Ala Val His Gln Arg Ile Asp Gly
         20                  25                  30

Ile Val Ser Asp Asp Pro Ala Asp Leu Gly Gly Leu Pro Thr Val
         35                  40                  45

Arg Lys Ile Leu Leu Tyr Asp Gly Pro Thr Ala Glu Ala Pro Glu Thr
 50                  55                  60

Pro Asp Leu Ser Ala Ala Asp Ile Val Ile Leu Pro Ser Gly Leu Thr
 65                  70                  75                  80

Gly Arg Arg Ala Leu Glu Glu Arg His Pro Ala Val Gln Phe Gly Arg
                 85                  90                  95

Arg Val Glu Ile Val Asp Ala Pro Ser Leu Glu Ala Cys Asp Ala
                100                 105                 110

Ala His Thr Glu Pro Trp Ser Leu Leu Asp Phe Arg Asp Pro Thr Lys
                115                 120                 125

Ile Pro Leu Glu Ile Val Ile Ala Ala Val Gly Ala Glu Gly Ser
130                 135                 140

Ile Val Thr Arg Ala Asp Asp Ala Val Glu Ala Gln Ile Val Phe Gly
145                 150                 155                 160

Val Leu Glu Leu Gly Ser Asp Gly Val Met Met Pro Gly Arg Ala Val
                165                 170                 175

Gly Asp Ala Thr Ala Leu Lys Arg Ala Thr Glu Ala Ala Thr Gly Glu
                180                 185                 190

Leu Glu Leu Val Glu Leu Glu Ile Thr Ala Thr Thr His Ile Gly Ile
                195                 200                 205

Gly Glu Arg Ala Cys Val Asp Thr Cys Ala Tyr Leu Arg Glu Asp Glu
                210                 215                 220

Gly Ile Leu Val Gly Ser Tyr Ser Lys Gly Met Ile Leu Cys Val Ser
225                 230                 235                 240

Glu Thr His Pro Leu Pro Tyr Met Pro Thr Arg Pro Phe Arg Val Asn
                245                 250                 255

Ala Gly Ala Ile His Ser Tyr Thr Val Ser Ala Gly Arg Thr Gln
                260                 265                 270

Tyr Leu Ser Glu Leu His Ser Gly Ser Lys Val Leu Ala Val Asp Val
                275                 280                 285

Lys Gly Arg Thr Arg Ile Val Pro Val Gly Arg Val Lys Ile Glu Lys
                290                 295                 300

Arg Pro Leu Ile Ser Val Asp Ala Val Ala Gly Asn Gly Arg Glu Val
305                 310                 315                 320

Asn Leu Ile Leu Gln Asp Asp Trp His Val Arg Val Leu Gly Pro Gly
                325                 330                 335

Gly Ala Val Leu Asn Ser Thr Glu Leu Lys Pro Gly Asp Arg Val Leu
                340                 345                 350

Gly His Leu Pro Thr Ala Asp Arg His Val Gly Tyr Pro Ile Asp Glu
                355                 360                 365

Phe Cys Arg Glu Gln
    370

<210> SEQ ID NO 28
<211> LENGTH: 1065
<212> TYPE: DNA
<213> ORGANISM: Burkholderia sp.
<220> FEATURE:
<221> NAME/KEY: CDS
<222> LOCATION: (1)..(1065)

<400> SEQUENCE: 28
```

```
atg cat cgc tat ccg tgg atc gac ctg cgc gcg ctc ggc gcg cag gca      48
Met His Arg Tyr Pro Trp Ile Asp Leu Arg Ala Leu Gly Ala Gln Ala
 1               5                  10                  15 ggc gcc gtc gcg gcc gac gcg gcg agg gcc ggt gtg ggc cgt gtc gtc      96
Gly Ala Val Ala Ala Asp Ala Ala Arg Ala Gly Val Gly Arg Val Val
             20                  25                  30 gtg gcc gag gcc gat cgc gac acc ttc gcg gcc ggc gcg gca gcg caa     144
Val Ala Glu Ala Asp Arg Asp Thr Phe Ala Ala Gly Ala Ala Ala Gln
         35                  40                  45 ctg gcc gtt tcg acg gcg ggc gtc gcg aca ctg gtc gac gac gcg cat     192
Leu Ala Val Ser Thr Ala Gly Val Ala Thr Leu Val Asp Asp Ala His
 50                  55                  60 gcg ccg ctc gca ggc gtt cgc gtg agg atc gac ggc gcg gcg gat ttc     240
Ala Pro Leu Ala Gly Val Arg Val Arg Ile Asp Gly Ala Ala Asp Phe
 65                  70                  75                  80 gac gcc gcg cgc act gca atc gcg cgg cac gcg ctc gtg ctg atc gac     288
Asp Ala Ala Arg Thr Ala Ile Ala Arg His Ala Leu Val Leu Ile Asp
                 85                  90                  95 tat gcg ctc gcg acc acg gtg ccg ctc gag cgc ctg ctc gcg gat gcc     336
Tyr Ala Leu Ala Thr Thr Val Pro Leu Glu Arg Leu Leu Ala Asp Ala
            100                 105                 110 ggc gat gct gcg tgc cgc atc gtc gtg tcg ctg gcc gat ccg cac ggc     384
Gly Asp Ala Ala Cys Arg Ile Val Val Ser Leu Ala Asp Pro His Gly
        115                 120                 125 gcg gcc tac ctc gtg cgc aag cat gcg cag tcg ccg gtc gac atc gcg     432
Ala Ala Tyr Leu Val Arg Lys His Ala Gln Ser Pro Val Asp Ile Ala
    130                 135                 140 ttc gca ccg cgc gat gcg gtc gcg ttg cgc agc gtg ctg gcc gcg tgc     480
Phe Ala Pro Arg Asp Ala Val Ala Leu Arg Ser Val Leu Ala Ala Cys
145                 150                 155                 160 ggc gag ctg cgc gca cgc gag ccg ctg aag ctg aaa aca ttc gag gtg     528
Gly Glu Leu Arg Ala Arg Glu Pro Leu Lys Leu Lys Thr Phe Glu Val
                165                 170                 175 cag cgc gtc gag ccg ctc ggc gtc ggg ctg cat gcg gtg atc gac ggc     576
Gln Arg Val Glu Pro Leu Gly Val Gly Leu His Ala Val Ile Asp Gly
            180                 185                 190 tgt tcg cag ctg gac ggc gaa gag tgc gtg ctg gcc ggc gcg agc gcg     624
Cys Ser Gln Leu Asp Gly Glu Glu Cys Val Leu Ala Gly Ala Ser Ala
        195                 200                 205 acc agc atg ctg ctc gtc gtc gcg gcc ggc gcg cat ccg ccg ggc         672
Thr Ser Met Leu Leu Val Val Ala Ala Gly Ala Ala His Pro Pro Gly
    210                 215                 220 cgg ccg ctc acg ttc ggc atc gat gcg ggc tcg gcc gaa tcg ttc gtg     720
Arg Pro Leu Thr Phe Gly Ile Asp Ala Gly Ser Ala Glu Ser Phe Val
225                 230                 235                 240 ttc tgc ggc ggc gac cgc gcg cgc cag ctt tcg ctg ctg cgt tcg ggc     768
Phe Cys Gly Gly Asp Arg Ala Arg Gln Leu Ser Leu Leu Arg Ser Gly
                245                 250                 255 gag cgg atc ctg acg gtc ggt gcg gcg ggc gac acg cgc gcg atc gtg     816
Glu Arg Ile Leu Thr Val Gly Ala Ala Gly Asp Thr Arg Ala Ile Val
            260                 265                 270 gtc ggc cgc gtg cgg atc gaa tcc gcg ccg ctc gtt gcg ctg cac acg     864
Val Gly Arg Val Arg Ile Glu Ser Ala Pro Leu Val Ala Leu His Thr
        275                 280                 285 cgc agc gcc tcc ggc gcg aac acg cgc gtc gtg atg cgc ggc gac cgc     912
Arg Ser Ala Ser Gly Ala Asn Thr Arg Val Val Met Arg Gly Asp Arg
    290                 295                 300 gca gtg cgt ttc cgg acc gac gac ggc gcg cgc gtc ggt ctt gcc gat     960
Ala Val Arg Phe Arg Thr Asp Asp Gly Ala Arg Val Gly Leu Ala Asp
305                 310                 315                 320
```

```
gtc gcg ccc ggt atc cgg ctt gcc ggc tac gaa ccg ggc gcc ggc tgg      1008
Val Ala Pro Gly Ile Arg Leu Ala Gly Tyr Glu Pro Gly Ala Gly Trp
            325                 330                 335 gtg gat tgc cgg atg agg gcc gcc gcg tcg cgt tcg gtt tcc gtc          1056
Val Asp Cys Arg Met Arg Ala Ala Ala Ser Arg Ser Val Val Ser Val
        340                 345                 350 agc cgc tag                                                          1065
Ser Arg <210> SEQ ID NO 29
<211> LENGTH: 354
<212> TYPE: PRT
<213> ORGANISM: Burkholderia sp.

<400> SEQUENCE: 29

Met His Arg Tyr Pro Trp Ile Asp Leu Arg Ala Leu Gly Ala Gln Ala
1               5                   10                  15

Gly Ala Val Ala Ala Asp Ala Ala Arg Ala Gly Val Gly Arg Val Val
            20                  25                  30

Val Ala Glu Ala Asp Arg Asp Thr Phe Ala Gly Ala Ala Ala Gln
        35                  40                  45

Leu Ala Val Ser Thr Ala Gly Val Ala Thr Leu Val Asp Asp Ala His
    50                  55                  60

Ala Pro Leu Ala Gly Val Arg Val Arg Ile Asp Gly Ala Ala Asp Phe
65                  70                  75                  80

Asp Ala Ala Arg Thr Ala Ile Ala Arg His Ala Leu Val Leu Ile Asp
                85                  90                  95

Tyr Ala Leu Ala Thr Thr Val Pro Leu Glu Arg Leu Leu Ala Asp Ala
            100                 105                 110

Gly Asp Ala Ala Cys Arg Ile Val Val Ser Leu Ala Asp Pro His Gly
        115                 120                 125

Ala Ala Tyr Leu Val Arg Lys His Ala Gln Ser Pro Val Asp Ile Ala
    130                 135                 140

Phe Ala Pro Arg Asp Ala Val Ala Leu Arg Ser Val Leu Ala Ala Cys
145                 150                 155                 160

Gly Glu Leu Arg Ala Arg Glu Pro Leu Lys Leu Lys Thr Phe Glu Val
                165                 170                 175

Gln Arg Val Glu Pro Leu Gly Val Gly Leu His Ala Val Ile Asp Gly
            180                 185                 190

Cys Ser Gln Leu Asp Gly Glu Glu Cys Val Leu Ala Gly Ala Ser Ala
        195                 200                 205

Thr Ser Met Leu Leu Val Val Ala Gly Ala Ala His Pro Pro Gly
    210                 215                 220

Arg Pro Leu Thr Phe Gly Ile Asp Ala Gly Ser Ala Glu Ser Phe Val
225                 230                 235                 240

Phe Cys Gly Gly Asp Arg Ala Arg Gln Leu Ser Leu Leu Arg Ser Gly
                245                 250                 255

Glu Arg Ile Leu Thr Val Gly Ala Ala Gly Asp Thr Arg Ala Ile Val
            260                 265                 270

Val Gly Arg Val Arg Ile Glu Ser Ala Pro Leu Val Ala Leu His Thr
        275                 280                 285

Arg Ser Ala Ser Gly Ala Asn Thr Arg Val Val Met Arg Gly Asp Arg
    290                 295                 300

Ala Val Arg Phe Arg Thr Asp Asp Gly Ala Arg Val Gly Leu Ala Asp
305                 310                 315                 320

Val Ala Pro Gly Ile Arg Leu Ala Gly Tyr Glu Pro Gly Ala Gly Trp
```

```
                        325                 330                 335
        Val Asp Cys Arg Met Arg Ala Ala Ala Ser Arg Ser Val Val Ser Val
                340                 345                 350

Ser Arg

<210> SEQ ID NO 30
<211> LENGTH: 1101
<212> TYPE: DNA
<213> ORGANISM: Burkholderia sp.
<220> FEATURE:
<221> NAME/KEY: CDS
<222> LOCATION: (1)..(1101)

<400> SEQUENCE: 30 ttg aag aag ctt tcc tgg att gac ctg cgc aac atc ggt gag ctc gcg        48
Met Lys Lys Leu Ser Trp Ile Asp Leu Arg Asn Ile Gly Glu Leu Ala
1               5                   10                  15 gac gag atc acc gag gaa gcg ttg cat gtc ggc gtg tcc gca ttc gtc        96
Asp Glu Ile Thr Glu Glu Ala Leu His Val Gly Val Ser Ala Phe Val
            20                  25                  30 gtg aag gat gcg gag cag gcc ggg cgg ttg ccg ccg agc gcg tgc aag       144
Val Lys Asp Ala Glu Gln Ala Gly Arg Leu Pro Pro Ser Ala Cys Lys
        35                  40                  45 gtc gcg gtc gtc gat cgg cag ccg gcc gat gcc gcg ctg ctg gag cag       192
Val Ala Val Val Asp Arg Gln Pro Ala Asp Ala Ala Leu Leu Glu Gln
    50                  55                  60 gtg cag atc atc ctc gtg aag gat ggc ctg ccg gtc gat ttc gcg gtg       240
Val Gln Ile Ile Leu Val Lys Asp Gly Leu Pro Val Asp Phe Ala Val
65                  70                  75                  80 ccg gac ggc gtt gag atc ggc gtg ttc atc gag gtg acg ggc gag gcg       288
Pro Asp Gly Val Glu Ile Gly Val Phe Ile Glu Val Thr Gly Glu Ala
                85                  90                  95 acg ctc acg cgc gca tgc gag ctg tcg acc acg acg ccg tgg ctg ctc       336
Thr Leu Thr Arg Ala Cys Glu Leu Ser Thr Thr Thr Pro Trp Leu Leu
            100                 105                 110 gtc gaa ttc ctg cag gac ccg agc aag atc ccg ctc gag atc ctg ctg       384
Val Glu Phe Leu Gln Asp Pro Ser Lys Ile Pro Leu Glu Ile Leu Leu
        115                 120                 125 gcc gcc gcc gat cag gcg tcg ggc gag ctg atc acc gtc gtg gcc gac       432
Ala Ala Ala Asp Gln Ala Ser Gly Glu Leu Ile Thr Val Val Ala Asp
    130                 135                 140 ctg gag gat gcg gag gtc acg ctg aac gta ctg cag cgc ggc ccc gaa       480
Leu Glu Asp Ala Glu Val Thr Leu Asn Val Leu Gln Arg Gly Pro Glu
145                 150                 155                 160 ggc gtg ctg gtc tcg ccg acg cag gtc ggg cag gcc acg cag ctc gtg       528
Gly Val Leu Val Ser Pro Thr Gln Val Gly Gln Ala Thr Gln Leu Val
                165                 170                 175 tcg atc tgc agc gac acg gtc gag gat ctg cag ctc gag gaa atc gag       576
Ser Ile Cys Ser Asp Thr Val Glu Asp Leu Gln Leu Glu Glu Ile Glu
            180                 185                 190 atc gtc gga ctc acg cac ctc ggg ccg ggc gaa cgc gtg tgc gtc gat       624
Ile Val Gly Leu Thr His Leu Gly Pro Gly Glu Arg Val Cys Val Asp
        195                 200                 205 acc tgc tcg cgt ttc gaa cag gac gag ggc atc ctc gtc ggc tcg tat       672
Thr Cys Ser Arg Phe Glu Gln Asp Glu Gly Ile Leu Val Gly Ser Tyr
    210                 215                 220 tcg acc ggc atg atc ctc atc agc agc gag acg cac ccg ctg ccg tac       720
Ser Thr Gly Met Ile Leu Ile Ser Ser Glu Thr His Pro Leu Pro Tyr
225                 230                 235                 240 atg ccg acc cgc ccg ttc cgc gtg aac gcg gcc gcg ctt cat tcg tac       768
Met Pro Thr Arg Pro Phe Arg Val Asn Ala Ala Ala Leu His Ser Tyr
```

```
                    245                 250                 255
gtc gtc gcg ccg gac aac cgc acg cgc tat ctc gcc gag ctt gaa tcg      816
Val Val Ala Pro Asp Asn Arg Thr Arg Tyr Leu Ala Glu Leu Glu Ser
            260                 265                 270 ggc gcg gag atc ctc gcc gtc aac gtg cag ggc aag gca cgc cgc gtc      864
Gly Ala Glu Ile Leu Ala Val Asn Val Gln Gly Lys Ala Arg Arg Val
        275                 280                 285 gtg gtc ggg cgc gcg aaa gtc gag acg cgg ccg ctg ctg ctg atc gaa      912
Val Val Gly Arg Ala Lys Val Glu Thr Arg Pro Leu Leu Leu Ile Glu
    290                 295                 300 gcg aag aat gcc gcc aat cgc gcg atc aac atc atc gcg cag gac gac      960
Ala Lys Asn Ala Ala Asn Arg Ala Ile Asn Ile Ile Ala Gln Asp Asp
305                 310                 315                 320 tgg cac gtg cgc gtg ctc ggg ccg aag ggc agc gtg cac aac atc acg     1008
Trp His Val Arg Val Leu Gly Pro Lys Gly Ser Val His Asn Ile Thr
                325                 330                 335 gag ctc aag cgc ggc gac cgc atc ctc ggc tac acg ctc gat gcg cag     1056
Glu Leu Lys Arg Gly Asp Arg Ile Leu Gly Tyr Thr Leu Asp Ala Gln
            340                 345                 350 cgc cac gtc ggc tac ccg atc acg gaa ttc ctg cac gag cag tga         1101
Arg His Val Gly Tyr Pro Ile Thr Glu Phe Leu His Glu Gln
        355                 360                 365

<210> SEQ ID NO 31
<211> LENGTH: 366
<212> TYPE: PRT
<213> ORGANISM: Burkholderia sp.

<400> SEQUENCE: 31

Met Lys Lys Leu Ser Trp Ile Asp Leu Arg Asn Ile Gly Glu Leu Ala
1               5                   10                  15

Asp Glu Ile Thr Glu Glu Ala Leu His Val Gly Val Ser Ala Phe Val
            20                  25                  30

Val Lys Asp Ala Glu Gln Ala Gly Arg Leu Pro Pro Ser Ala Cys Lys
        35                  40                  45

Val Ala Val Val Asp Arg Gln Pro Ala Asp Ala Leu Leu Glu Gln
    50                  55                  60

Val Gln Ile Ile Leu Val Lys Asp Gly Leu Pro Val Asp Phe Ala Val
65                  70                  75                  80

Pro Asp Gly Val Glu Ile Gly Val Phe Ile Glu Val Thr Gly Glu Ala
                85                  90                  95

Thr Leu Thr Arg Ala Cys Glu Leu Ser Thr Thr Thr Pro Trp Leu Leu
            100                 105                 110

Val Glu Phe Leu Gln Asp Pro Ser Lys Ile Pro Leu Glu Ile Leu Leu
        115                 120                 125

Ala Ala Ala Asp Gln Ala Ser Gly Glu Leu Ile Thr Val Val Ala Asp
    130                 135                 140

Leu Glu Asp Ala Glu Val Thr Leu Asn Val Leu Gln Arg Gly Pro Glu
145                 150                 155                 160

Gly Val Leu Val Ser Pro Thr Gln Val Gly Gln Ala Thr Gln Leu Val
                165                 170                 175

Ser Ile Cys Ser Asp Thr Val Glu Asp Leu Gln Leu Glu Ile Glu
            180                 185                 190

Ile Val Gly Leu Thr His Leu Gly Pro Gly Glu Arg Val Cys Val Asp
        195                 200                 205

Thr Cys Ser Arg Phe Glu Gln Asp Glu Gly Ile Leu Val Gly Ser Tyr
    210                 215                 220
```

```
Ser Thr Gly Met Ile Leu Ile Ser Ser Glu Thr His Pro Leu Pro Tyr
225                 230                 235                 240

Met Pro Thr Arg Pro Phe Arg Val Asn Ala Ala Leu His Ser Tyr
            245                 250                 255

Val Val Ala Pro Asp Asn Arg Thr Arg Tyr Leu Ala Glu Leu Glu Ser
            260                 265                 270

Gly Ala Glu Ile Leu Ala Val Asn Val Gln Gly Lys Ala Arg Arg Val
            275                 280                 285

Val Val Gly Arg Ala Lys Val Glu Thr Arg Pro Leu Leu Leu Ile Glu
290                 295                 300

Ala Lys Asn Ala Ala Asn Arg Ala Ile Asn Ile Ile Ala Gln Asp Asp
305                 310                 315                 320

Trp His Val Arg Val Leu Gly Pro Lys Gly Ser Val His Asn Ile Thr
            325                 330                 335

Glu Leu Lys Arg Gly Asp Arg Ile Leu Gly Tyr Thr Leu Asp Ala Gln
            340                 345                 350

Arg His Val Gly Tyr Pro Ile Thr Glu Phe Leu His Glu Gln
            355                 360             365

<210> SEQ ID NO 32
<211> LENGTH: 1242
<212> TYPE: DNA
<213> ORGANISM: Streptomyces scabies
<220> FEATURE:
<221> NAME/KEY: CDS
<222> LOCATION: (1)..(1242)

<400> SEQUENCE: 32
```

| | | | | | | | | | | | | | | | | |
|---|---|---|---|---|---|---|---|---|---|---|---|---|---|---|---|---|
| atg | agg | ttc | gcg | tgg | atc | gat | ctc | cgt | gaa | gtc | ccc | cgt | cca | cag | ctc | 48 |
| Met | Arg | Phe | Ala | Trp | Ile | Asp | Leu | Arg | Glu | Val | Pro | Arg | Pro | Gln | Leu | |
| 1 | | | | 5 | | | | | 10 | | | | | 15 | | |
| cag | gcg | gtg | gtg | gac | gcg | gcc | gtc | cac | gcc | cgg | atg | gcc | gga | gtg | gtc | 96 |
| Gln | Ala | Val | Val | Asp | Ala | Ala | Val | His | Ala | Arg | Met | Ala | Gly | Val | Val | |
| | | | 20 | | | | | 25 | | | | | 30 | | | |
| tcc | gcg | gac | gcc | gag | ctc | ctg | ggg | acc | ctg | ccg | ccg | acg | gtg | acc | cgg | 144 |
| Ser | Ala | Asp | Ala | Glu | Leu | Leu | Gly | Thr | Leu | Pro | Pro | Thr | Val | Thr | Arg | |
| | 35 | | | | | 40 | | | | | 45 | | | | | |
| gtg | ctg | gcc | tcc | gag | tcc | cgg | acc | gcg | gcc | ccc | gcg | aag | aag | ccc | gcg | 192 |
| Val | Leu | Ala | Ser | Glu | Ser | Arg | Thr | Ala | Ala | Pro | Ala | Lys | Lys | Pro | Ala | |
| 50 | | | | | 55 | | | | | 60 | | | | | | |
| gac | aag | aac | gcc | aag | ggc | gac | agg | agc | gac | gcg | ggc | cag | ggc | ggc | ggc | 240 |
| Asp | Lys | Asn | Ala | Lys | Gly | Asp | Arg | Ser | Asp | Ala | Gly | Gln | Gly | Gly | Gly | |
| 65 | | | | 70 | | | | | 75 | | | | | 80 | | |
| aag | gac | acg | cag | gct | gcc | gac | ggc | gcc | ggg | ccc | gcg | agc | ggc | gcc | cct | 288 |
| Lys | Asp | Thr | Gln | Ala | Ala | Asp | Gly | Ala | Gly | Pro | Ala | Ser | Gly | Ala | Pro | |
| | | | | 85 | | | | | 90 | | | | | 95 | | |
| gcc | ggc | acc | gga | tgc | gac | ctg | ctg | ctg | cgg | aag | ttc | acc | acc | cag | gac | 336 |
| Ala | Gly | Thr | Gly | Cys | Asp | Leu | Leu | Leu | Arg | Lys | Phe | Thr | Thr | Gln | Asp | |
| | | | 100 | | | | | 105 | | | | | 110 | | | |
| gaa | ctg | gac | gcg | ctc | gcc | gcc | gag | aac | cgg | ggc | acc | acc | ggc | aca | ccg | 384 |
| Glu | Leu | Asp | Ala | Leu | Ala | Ala | Glu | Asn | Arg | Gly | Thr | Thr | Gly | Thr | Pro | |
| | 115 | | | | | 120 | | | | | 125 | | | | | |
| gtg | ccc | cgt | acg | ccc | gtc | gcc | ggc | ttc | gtc | gac | gta | cgg | gac | gac | cgc | 432 |
| Val | Pro | Arg | Thr | Pro | Val | Ala | Gly | Phe | Val | Asp | Val | Arg | Asp | Asp | Arg | |
| 130 | | | | | 135 | | | | | 140 | | | | | | |
| acg | ctc | cgg | ctg | tcg | tgc | gtc | ggc | gcg | atg | gca | ctg | ccg | tac | acg | gtg | 480 |
| Thr | Leu | Arg | Leu | Ser | Cys | Val | Gly | Ala | Met | Ala | Leu | Pro | Tyr | Thr | Val | |
| 145 | | | | 150 | | | | | 155 | | | | | 160 | | |
| atc | cat | ttc | gcc | gac | ccg | acg | aag | atc | ccg | ctg | gag | atc | gtg | ctc | gcg | 528 |
| Ile | His | Phe | Ala | Asp | Pro | Thr | Lys | Ile | Pro | Leu | Glu | Ile | Val | Leu | Ala | |

```
                     165                 170                 175
gcg gcc gag tcg gcc gag ggg aag ctg gtg acc gtc gtc ggg gac ctg         576
Ala Ala Glu Ser Ala Glu Gly Lys Leu Val Thr Val Val Gly Asp Leu
            180                 185                 190 gag gag gcg gcc atc gtc ttc gac gtg ctc gaa cgc ggc tcc gac ggc         624
Glu Glu Ala Ala Ile Val Phe Asp Val Leu Glu Arg Gly Ser Asp Gly
                195                 200                 205 atc ctg ttc acc ccc cgg agc gcg gac gac gtg ttc gcg ctg gcc cgg         672
Ile Leu Phe Thr Pro Arg Ser Ala Asp Asp Val Phe Ala Leu Ala Arg
    210                 215                 220 ctg ctg gag gcg acg acc ccg cag ctg gag atg tcc acg ctg acg gtg         720
Leu Leu Glu Ala Thr Thr Pro Gln Leu Glu Met Ser Thr Leu Thr Val
225                 230                 235                 240 gag agc atc cgg cac gtc ggg ctc ggc gac cgg gtc tgt gtg gac acc         768
Glu Ser Ile Arg His Val Gly Leu Gly Asp Arg Val Cys Val Asp Thr
                245                 250                 255 tgc tcg cac ttc gag gag gac gag ggc atc ctc gtc ggc tcg tac tcg         816
Cys Ser His Phe Glu Glu Asp Glu Gly Ile Leu Val Gly Ser Tyr Ser
            260                 265                 270 tcc ggt ttc gtg ctc tgc tgc agc gag acg cac ccg ctg ccg tac atg         864
Ser Gly Phe Val Leu Cys Cys Ser Glu Thr His Pro Leu Pro Tyr Met
        275                 280                 285 ccg acc cgg ccg ttc cgg gtc aac gcc ggc gcc ctg cac tcg tac acg         912
Pro Thr Arg Pro Phe Arg Val Asn Ala Gly Ala Leu His Ser Tyr Thr
    290                 295                 300 ctg ggc ccc gac aac cgc acc agc tac ctc agc gag gtc ggt tcc ggc         960
Leu Gly Pro Asp Asn Arg Thr Ser Tyr Leu Ser Glu Val Gly Ser Gly
305                 310                 315                 320 agc gcg ctg ctg gcg gtc ggt gcc gac ggc cgt acc cgg cgg gtg gtc         1008
Ser Ala Leu Leu Ala Val Gly Ala Asp Gly Arg Thr Arg Arg Val Val
                325                 330                 335 gtc ggg cgg gcc aag ctg gag tcc cgg ccg ctg ctg gag atc cgc acg         1056
Val Gly Arg Ala Lys Leu Glu Ser Arg Pro Leu Leu Glu Ile Arg Thr
            340                 345                 350 cac gcg gag gac ggg cgg ctg gtg agc ctg acc gtg cag gac gac tgg         1104
His Ala Glu Asp Gly Arg Leu Val Ser Leu Thr Val Gln Asp Asp Trp
        355                 360                 365 cac gtc cgg gtg ctc ggg ccg ggc ggc aag gtc ctc aat gtc acc gaa         1152
His Val Arg Val Leu Gly Pro Gly Gly Lys Val Leu Asn Val Thr Glu
    370                 375                 380 ctg cgg gcc ggg gat gag ctg ctc ggc tat ctg gcg cag gac aag cgc         1200
Leu Arg Ala Gly Asp Glu Leu Leu Gly Tyr Leu Ala Gln Asp Lys Arg
385                 390                 395                 400 cat gtg ggc ctg ccc atc ggc gag ttc tgc aag gag gtc tga               1242
His Val Gly Leu Pro Ile Gly Glu Phe Cys Lys Glu Val
                405                 410

<210> SEQ ID NO 33
<211> LENGTH: 413
<212> TYPE: PRT
<213> ORGANISM: Streptomyces scabies

<400> SEQUENCE: 33

Met Arg Phe Ala Trp Ile Asp Leu Arg Glu Val Pro Arg Pro Gln Leu
1               5                   10                  15

Gln Ala Val Val Asp Ala Ala Val His Ala Arg Met Ala Gly Val Val
            20                  25                  30

Ser Ala Asp Ala Glu Leu Leu Gly Thr Leu Pro Pro Thr Val Thr Arg
        35                  40                  45

Val Leu Ala Ser Glu Ser Arg Thr Ala Ala Pro Ala Lys Lys Pro Ala
```

```
              50                  55                  60
Asp Lys Asn Ala Lys Gly Asp Arg Ser Asp Ala Gly Gln Gly Gly
 65                  70                  75                  80

Lys Asp Thr Gln Ala Ala Asp Gly Ala Gly Pro Ala Ser Gly Ala Pro
                 85                  90                  95

Ala Gly Thr Gly Cys Asp Leu Leu Leu Arg Lys Phe Thr Thr Gln Asp
                100                 105                 110

Glu Leu Asp Ala Leu Ala Ala Glu Asn Arg Gly Thr Thr Gly Thr Pro
                115                 120                 125

Val Pro Arg Thr Pro Val Ala Gly Phe Val Asp Val Arg Asp Asp Arg
130                 135                 140

Thr Leu Arg Leu Ser Cys Val Gly Ala Met Ala Leu Pro Tyr Thr Val
145                 150                 155                 160

Ile His Phe Ala Asp Pro Thr Lys Ile Pro Leu Glu Ile Val Leu Ala
                165                 170                 175

Ala Ala Glu Ser Ala Glu Gly Lys Leu Val Thr Val Val Gly Asp Leu
                180                 185                 190

Glu Glu Ala Ala Ile Val Phe Asp Val Leu Glu Arg Gly Ser Asp Gly
                195                 200                 205

Ile Leu Phe Thr Pro Arg Ser Ala Asp Asp Val Phe Ala Leu Ala Arg
210                 215                 220

Leu Leu Glu Ala Thr Thr Pro Gln Leu Glu Met Ser Thr Leu Thr Val
225                 230                 235                 240

Glu Ser Ile Arg His Val Gly Leu Gly Asp Arg Val Cys Val Asp Thr
                245                 250                 255

Cys Ser His Phe Glu Glu Asp Glu Gly Ile Leu Val Gly Ser Tyr Ser
                260                 265                 270

Ser Gly Phe Val Leu Cys Cys Ser Glu Thr His Pro Leu Pro Tyr Met
                275                 280                 285

Pro Thr Arg Pro Phe Arg Val Asn Ala Gly Ala Leu His Ser Tyr Thr
290                 295                 300

Leu Gly Pro Asp Asn Arg Thr Ser Tyr Leu Ser Glu Val Gly Ser Gly
305                 310                 315                 320

Ser Ala Leu Leu Ala Val Gly Ala Asp Gly Arg Thr Arg Arg Val Val
                325                 330                 335

Val Gly Arg Ala Lys Leu Glu Ser Arg Pro Leu Leu Glu Ile Arg Thr
                340                 345                 350

His Ala Glu Asp Gly Arg Leu Val Ser Leu Thr Val Gln Asp Asp Trp
                355                 360                 365

His Val Arg Val Leu Gly Pro Gly Gly Lys Val Leu Asn Val Thr Glu
                370                 375                 380

Leu Arg Ala Gly Asp Glu Leu Leu Gly Tyr Leu Ala Gln Asp Lys Arg
385                 390                 395                 400

His Val Gly Leu Pro Ile Gly Glu Phe Cys Lys Glu Val
                405                 410

<210> SEQ ID NO 34
<211> LENGTH: 1086
<212> TYPE: DNA
<213> ORGANISM: Methanococcus jannaschii
<220> FEATURE:
<221> NAME/KEY: CDS
<222> LOCATION: (1)..(1086)

<400> SEQUENCE: 34 atg aaa ttt gga tgg gtt aat gtt att gga gat aac tgg gaa gag aaa      48
```

```
Met Lys Phe Gly Trp Val Asn Val Ile Gly Asp Asn Trp Glu Glu Lys
1               5                   10                  15 aag aag ata gta aca aca gca tta gag tca tca atc cca gta gtt gtt        96
Lys Lys Ile Val Thr Thr Ala Leu Glu Ser Ser Ile Pro Val Val Val
            20                  25                  30 gct gaa cca gaa gat att gaa aaa att aaa gaa ctt gga aat att aaa       144
Ala Glu Pro Glu Asp Ile Glu Lys Ile Lys Glu Leu Gly Asn Ile Lys
        35                  40                  45 gtt gcc tcc cat tcc tta gac gcg gat att gtt tta gta aat aaa aat       192
Val Ala Ser His Ser Leu Asp Ala Asp Ile Val Leu Val Asn Lys Asn
    50                  55                  60 gac aac ata gag ttt tta aaa gag gca aag aac tta gga aaa gaa aca       240
Asp Asn Ile Glu Phe Leu Lys Glu Ala Lys Asn Leu Gly Lys Glu Thr
65                  70                  75                  80 gcc ata tac att cca att gaa tca aag gaa gat gaa gag ttt gct tca       288
Ala Ile Tyr Ile Pro Ile Glu Ser Lys Glu Asp Glu Glu Phe Ala Ser
                85                  90                  95 gag gtt gca agg ttt gga ttt gtt gat aac att atc tta gag ggg aga       336
Glu Val Ala Arg Phe Gly Phe Val Asp Asn Ile Ile Leu Glu Gly Arg
            100                 105                 110 gat tgg aca atc att cca tta gaa aat tta ata gct gat tta ttc cat       384
Asp Trp Thr Ile Ile Pro Leu Glu Asn Leu Ile Ala Asp Leu Phe His
        115                 120                 125 agg gat gtt aag att gta gca agt gtt aat tca gtt gat gag gca aag       432
Arg Asp Val Lys Ile Val Ala Ser Val Asn Ser Val Asp Glu Ala Lys
    130                 135                 140 gtt gcc tat gaa att tta gag aaa ggg act gat ggg gtt ctc tta aat       480
Val Ala Tyr Glu Ile Leu Glu Lys Gly Thr Asp Gly Val Leu Leu Asn
145                 150                 155                 160 cca aaa aac tta gag gat ata aag gag tta tca aaa tta att gaa gag       528
Pro Lys Asn Leu Glu Asp Ile Lys Glu Leu Ser Lys Leu Ile Glu Glu
                165                 170                 175 atg aat aaa gag aaa gtg gct tta gat gta gca aca gta aca aag gtt       576
Met Asn Lys Glu Lys Val Ala Leu Asp Val Ala Thr Val Thr Lys Val
            180                 185                 190 gag cca ata ggt agt gga gac agg gtt tgt ata gat acc tgc tca cta       624
Glu Pro Ile Gly Ser Gly Asp Arg Val Cys Ile Asp Thr Cys Ser Leu
        195                 200                 205 atg aag ata gga gaa gga atg tta att ggc tcc tac tca aga gct ctc       672
Met Lys Ile Gly Glu Gly Met Leu Ile Gly Ser Tyr Ser Arg Ala Leu
    210                 215                 220 ttc tta gtt cat tct gag act gtt gag aac cct tac gta gct aca agg       720
Phe Leu Val His Ser Glu Thr Val Glu Asn Pro Tyr Val Ala Thr Arg
225                 230                 235                 240 cca ttc aga gtt aat gct gga cct gtt cat gca tac ata tta tgc cct       768
Pro Phe Arg Val Asn Ala Gly Pro Val His Ala Tyr Ile Leu Cys Pro
                245                 250                 255 ggt aat aaa aca aaa tat ctc agt gag cta aaa gct gga gat aag gtt       816
Gly Asn Lys Thr Lys Tyr Leu Ser Glu Leu Lys Ala Gly Asp Lys Val
            260                 265                 270 ttg att gta gat aag gat gga aat aca agg gag gca ata gtt ggc agg       864
Leu Ile Val Asp Lys Asp Gly Asn Thr Arg Glu Ala Ile Val Gly Arg
        275                 280                 285 gta aag att gaa aga aga cct tta gtg tta att gag gca gag tat aaa       912
Val Lys Ile Glu Arg Arg Pro Leu Val Leu Ile Glu Ala Glu Tyr Lys
    290                 295                 300 ggg gat att att aga act ata ctg cag aat gct gaa act ata aga ttg       960
Gly Asp Ile Ile Arg Thr Ile Leu Gln Asn Ala Glu Thr Ile Arg Leu
305                 310                 315                 320 gtt aat gaa aaa gga gaa cca att tct gtt gtt gat tta aaa cct gga      1008
```

```
Val Asn Glu Lys Gly Glu Pro Ile Ser Val Val Asp Leu Lys Pro Gly
                325                 330                 335 gac aaa gtt tta ata aaa cca gag gag tat gca agg cat ttt gga atg    1056
Asp Lys Val Leu Ile Lys Pro Glu Glu Tyr Ala Arg His Phe Gly Met
        340                 345                 350 gca ata aaa gag acg att att gaa aag tga                            1086
Ala Ile Lys Glu Thr Ile Ile Glu Lys
        355                 360

<210> SEQ ID NO 35
<211> LENGTH: 361
<212> TYPE: PRT
<213> ORGANISM: Methanococcus jannaschii

<400> SEQUENCE: 35
```

Met Lys Phe Gly Trp Val Asn Val Ile Gly Asp Asn Trp Glu Lys
1               5                   10                  15

Lys Lys Ile Val Thr Thr Ala Leu Glu Ser Ser Ile Pro Val Val
            20                  25                  30

Ala Glu Pro Glu Asp Ile Glu Lys Ile Lys Glu Leu Gly Asn Ile Lys
            35                  40                  45

Val Ala Ser His Ser Leu Asp Ala Asp Ile Val Leu Val Asn Lys Asn
50                  55                  60

Asp Asn Ile Glu Phe Leu Lys Glu Ala Lys Asn Leu Gly Lys Glu Thr
65                  70                  75                  80

Ala Ile Tyr Ile Pro Ile Glu Ser Lys Glu Asp Glu Glu Phe Ala Ser
                85                  90                  95

Glu Val Ala Arg Phe Gly Phe Val Asp Asn Ile Ile Leu Glu Gly Arg
            100                 105                 110

Asp Trp Thr Ile Ile Pro Leu Glu Asn Leu Ile Ala Asp Leu Phe His
        115                 120                 125

Arg Asp Val Lys Ile Val Ala Ser Val Asn Ser Val Asp Glu Ala Lys
130                 135                 140

Val Ala Tyr Glu Ile Leu Glu Lys Gly Thr Asp Gly Val Leu Leu Asn
145                 150                 155                 160

Pro Lys Asn Leu Glu Asp Ile Lys Glu Leu Ser Lys Leu Ile Glu Glu
                165                 170                 175

Met Asn Lys Glu Lys Val Ala Leu Asp Val Ala Thr Val Thr Lys Val
            180                 185                 190

Glu Pro Ile Gly Ser Gly Asp Arg Val Cys Ile Asp Thr Cys Ser Leu
        195                 200                 205

Met Lys Ile Gly Glu Gly Met Leu Ile Gly Ser Tyr Ser Arg Ala Leu
210                 215                 220

Phe Leu Val His Ser Glu Thr Val Glu Asn Pro Tyr Val Ala Thr Arg
225                 230                 235                 240

Pro Phe Arg Val Asn Ala Gly Pro Val His Ala Tyr Ile Leu Cys Pro
                245                 250                 255

Gly Asn Lys Thr Lys Tyr Leu Ser Glu Leu Lys Ala Gly Asp Lys Val
            260                 265                 270

Leu Ile Val Asp Lys Asp Gly Asn Thr Arg Glu Ala Ile Val Gly Arg
        275                 280                 285

Val Lys Ile Glu Arg Arg Pro Leu Val Leu Ile Glu Ala Glu Tyr Lys
290                 295                 300

Gly Asp Ile Ile Arg Thr Ile Leu Gln Asn Ala Glu Thr Ile Arg Leu
305                 310                 315                 320

Val Asn Glu Lys Gly Glu Pro Ile Ser Val Val Asp Leu Lys Pro Gly

```
                    325                 330                 335
Asp Lys Val Leu Ile Lys Pro Glu Glu Tyr Ala Arg His Phe Gly Met
            340                 345                 350

Ala Ile Lys Glu Thr Ile Ile Glu Lys
            355                 360

<210> SEQ ID NO 36
<211> LENGTH: 274
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(274)
<223> OTHER INFORMATION: Xaa represents any amino acid.

<400> SEQUENCE: 36

Ala Lys Xaa Leu Arg Leu Xaa Arg Leu His Arg Xaa Xaa Xaa Xaa Xaa
1               5                   10                  15

Xaa Xaa Gly Arg Leu Xaa Ile Val Pro Leu Asp His Ser Val Ser Asp
            20                  25                  30

Gly Pro Ile Ala Xaa Xaa Xaa Xaa Xaa Xaa Xaa Xaa Xaa Xaa Leu Asp
        35                  40                  45

Xaa Leu Val Xaa Asp Leu Ala Xaa Gly Gly Xaa Asp Ala Ile Val Leu
50                  55                  60

His Lys Gly Xaa Leu Arg His Leu Xaa Pro Xaa Xaa Xaa Xaa Xaa Met
65                  70                  75                  80

Ser Leu Ile Val His Leu Ser Ala Ser Thr Xaa His Ala Xaa Pro Asp
                85                  90                  95

Pro Xaa Ala Lys Xaa Leu Val Ala Ser Val Glu Glu Ala Leu Arg Leu
            100                 105                 110

Gly Ala Asp Ala Val Ser Val His Val Asn Leu Gly Ser Asp Xaa Glu
        115                 120                 125

Xaa Xaa Gln Ile Ala Asp Leu Gly Ala Val Ala Glu Xaa Cys Asp Xaa
130                 135                 140

Trp Gly Met Pro Leu Leu Ala Met Met Tyr Pro Arg Gly Pro Arg Ile
145                 150                 155                 160

Xaa Asp Pro Xaa Xaa Xaa Xaa Xaa Asp Pro Glu Leu Ile Ala His
            165                 170                 175

Ala Xaa Xaa Leu Ala Ala Asp Leu Gly Ala Asp Ile Val Lys Xaa Xaa
            180                 185                 190

Tyr Xaa Gly Xaa Val Xaa Ala Met Arg Asp Ile Val Ala Ala Ser Pro
        195                 200                 205

Ile Pro Val Val Val Ala Gly Gly Pro Lys Xaa Xaa Xaa Glu Asp Asp
        210                 215                 220

Leu Leu Ala Tyr Val Xaa Xaa Xaa Met Xaa Ala Gly Ala Ala Gly Val
225                 230                 235                 240

Ala Met Gly Arg Asn Val Phe Gln Ala Pro Asp Pro Xaa Ala Met Ala
            245                 250                 255

Xaa Arg Leu Ala Xaa Ile Val His Xaa Xaa Ala Xaa Xaa Gly Xaa Xaa
            260                 265                 270

Xaa Ala

<210> SEQ ID NO 37
<211> LENGTH: 417
<212> TYPE: PRT
<213> ORGANISM: Artificial
```

```
<220> FEATURE:
<223> OTHER INFORMATION: griH, consensus
<220> FEATURE:
<221> NAME/KEY: MISC_FEATURE
<222> LOCATION: (1)..(417)
<223> OTHER INFORMATION: Xaa represents any amino acid.

<400> SEQUENCE: 37
```

| | | | | | | | | | | | | | | |
|---|---|---|---|---|---|---|---|---|---|---|---|---|---|---|
| Lys | Leu | Xaa | Trp | Ile | Asp | Ile | Arg | Xaa | Val | Gly | Xaa | Glu | Xaa | Xaa |
| 1 | | | | 5 | | | | | 10 | | | | | 15 |
| Ala | Val | Val | Asp | Glu | Ala | Leu | His | Xaa | Arg | Val | Xaa | Ala | Val | Ser |
| | | | | 20 | | | | | 25 | | | | | 30 |
| Asp | Asp | Xaa | Asp | Xaa | Leu | Gly | Xaa | Leu | Pro | Pro | Thr | Val | Xaa | Lys | Val |
| | | 35 | | | | | 40 | | | | | 45 | | | |
| Leu | Leu | Xaa | Xaa | Xaa | Xaa | Xaa | Xaa | Xaa | Xaa | Xaa | Xaa | Xaa | Xaa |
| 50 | | | | | 55 | | | | | 60 | | | |
| Xaa | Xaa | Xaa | Asp | Ile | Val | Xaa | Leu | Xaa | Xaa | Xaa | Xaa | Xaa | Xaa | Xaa |
| 65 | | | | 70 | | | | | 75 | | | | | 80 |
| Xaa | Xaa | Xaa | Xaa | Xaa | Xaa | Xaa | Xaa | Xaa | Xaa | Xaa | Xaa | Xaa | Xaa | Xaa |
| | | | | 85 | | | | | 90 | | | | | 95 |
| Xaa | Xaa | Xaa | Xaa | Xaa | Xaa | Xaa | Xaa | Xaa | Xaa | Xaa | Xaa | Xaa | Xaa | Xaa |
| | | | | 100 | | | | | 105 | | | | | 110 |
| Xaa | Xaa | Xaa | Xaa | Xaa | Xaa | Glu | Xaa | Leu | Xaa | Xaa | Leu | Xaa | Xaa | Xaa | Xaa |
| | | | | 115 | | | | | 120 | | | | | 125 | |
| Pro | Xaa | Val | Xaa | Xaa | Gly | Xaa | Phe | Val | Glu | Ile | Xaa | Asp | Ala | Xaa | Thr |
| 130 | | | | | 135 | | | | | 140 | | | | | |
| Leu | Asp | Xaa | Ala | Cys | Xaa | Ala | Ala | Xaa | Xaa | Xaa | Trp | Ser | Leu | Leu |
| 145 | | | | 150 | | | | | 155 | | | | | 160 |
| Asp | Phe | Arg | Xaa | Asp | Pro | Thr | Lys | Ile | Pro | Leu | Glu | Ile | Val | Leu | Ala |
| | | | 165 | | | | | 170 | | | | | 175 | | |
| Ala | Ala | Xaa | Xaa | Ala | Xaa | Gly | Xaa | Ile | Val | Thr | Val | Val | Xaa | Asp | Leu |
| | | | 180 | | | | | 185 | | | | | 190 | | |
| Glu | Glu | Ala | Xaa | Ile | Val | Phe | Xaa | Val | Leu | Glu | Arg | Gly | Ser | Asp | Gly |
| | | | 195 | | | | | 200 | | | | | 205 | | |
| Val | Leu | Leu | Ala | Pro | Lys | Xaa | Ala | Val | Gly | Asp | Xaa | Ser | Xaa | Leu | Xaa |
| | 210 | | | | | 215 | | | | | 220 | | | | |
| Arg | Ile | Xaa | Glu | Ala | Xaa | Xaa | Xaa | Xaa | Xaa | Leu | Xaa | Leu | Xaa | Glu | Leu |
| 225 | | | | | 230 | | | | | 235 | | | | | 240 |
| Glu | Val | Xaa | Xaa | Val | Ser | His | Ile | Gly | Met | Gly | Glu | Arg | Ala | Cys | Val |
| | | | | 245 | | | | | 250 | | | | | 255 | |
| Asp | Thr | Cys | Ser | Xaa | Phe | Xaa | Glu | Asp | Glu | Gly | Ile | Leu | Val | Gly | Ser |
| | | | | 260 | | | | | 265 | | | | | 270 | |
| Tyr | Ser | Lys | Gly | Met | Ile | Leu | Xaa | Xaa | Ser | Glu | Thr | His | Pro | Leu | Pro |
| | | | 275 | | | | | 280 | | | | | 285 | | |
| Tyr | Met | Pro | Thr | Arg | Pro | Phe | Arg | Val | Asn | Ala | Gly | Ala | Ile | His | Ser |
| | 290 | | | | | 295 | | | | | 300 | | | | |
| Tyr | Thr | Leu | Xaa | Xaa | Gly | Xaa | Arg | Thr | Xaa | Tyr | Leu | Ser | Glu | Leu | Xaa |
| 305 | | | | | 310 | | | | | 315 | | | | | 320 |
| Ser | Gly | Ser | Lys | Val | Leu | Ala | Val | Asp | Xaa | Xaa | Gly | Arg | Thr | Arg | Xaa |
| | | | | 325 | | | | | 330 | | | | | 335 | |
| Val | Val | Val | Gly | Arg | Val | Lys | Ile | Glu | Thr | Arg | Pro | Leu | Ile | Xaa | Ile |
| | | | 340 | | | | | 345 | | | | | 350 | | |
| Asp | Ala | Xaa | Ala | Xaa | Xaa | Gly | Arg | Xaa | Val | Xaa | Leu | Ile | Leu | Gln | Asp |
| | | 355 | | | | | 360 | | | | | 365 | | | |
| Asp | Trp | His | Val | Arg | Val | Leu | Gly | Pro | Gly | Gly | Xaa | Val | Leu | Asn | Val |
| | 370 | | | | | 375 | | | | | 380 | | | | |

Thr Glu Leu Lys Pro Gly Asp Arg Val Leu Gly Tyr Leu Pro Xaa Xaa
385                 390                 395                 400

Xaa Xaa Xaa Asp Arg His Val Gly Tyr Pro Ile Xaa Glu Phe Cys Ile
            405                 410                 415

Glu

<210> SEQ ID NO 38
<211> LENGTH: 421
<212> TYPE: PRT
<213> ORGANISM: Corynebacterium glutamicum

<400> SEQUENCE: 38

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

```
Asn Val Leu Tyr Asp Asp Gln Val Gly Lys Val Ser Leu Val Gly Ala
            340                 345                 350
Gly Met Lys Ser His Pro Gly Val Thr Ala Glu Phe Met Glu Ala Leu
        355                 360                 365
Arg Asp Val Asn Val Asn Ile Glu Leu Ile Ser Thr Ser Glu Ile Arg
370                 375                 380
Ile Ser Val Leu Ile Arg Glu Asp Asp Leu Asp Ala Ala Arg Ala
385                 390                 395                 400
Leu His Glu Gln Phe Gln Leu Gly Gly Glu Asp Glu Ala Val Tyr
            405                 410                 415
Ala Gly Thr Gly Arg
            420

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gacaggacaa gcactggttg cactaccaag                                    30

<210> SEQ ID NO 40
<211> LENGTH: 30
<212> TYPE: DNA
<213> ORGANISM: Artificial
<220> FEATURE:
<223> OTHER INFORMATION: primer

<400> SEQUENCE: 40
ggtggtcatt gtaaaactac tcctttaaaa                                    30

<210> SEQ ID NO 41
<211> LENGTH: 1266
<212> TYPE: DNA
<213> ORGANISM: Corynebacterium glutamicum
<220> FEATURE:
<221> NAME/KEY: CDS
<222> LOCATION: (1)..(1263)

<400> SEQUENCE: 41 gtg gcc ctg gtc gta cag aaa tat ggc ggt tcc tcg ctt gag agt gcg    48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct    96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat   144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt   192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc   240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg   288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc   336
Gly Ser Gln Ala Gly Val Leu Thr Thr Glu Arg His Gly Asn Ala Arg
            100                 105                 110
```

| | | |
|---|---|---|
| att gtt gat gtc act cca ggt cgt gtg cgt gaa gca ctc gat gag ggc<br>Ile Val Asp Val Thr Pro Gly Arg Val Arg Glu Ala Leu Asp Glu Gly<br>115 120 125 | | 384 |
| aag atc tgc att gtt gct ggt ttc cag ggt gtt aat aaa gaa acc cgc<br>Lys Ile Cys Ile Val Ala Gly Phe Gln Gly Val Asn Lys Glu Thr Arg<br>130 135 140 | | 432 |
| gat gtc acc acg ttg ggt cgt ggt ggt tct gac act act gca gtt gcg<br>Asp Val Thr Thr Leu Gly Arg Gly Gly Ser Asp Thr Thr Ala Val Ala<br>145 150 155 160 | | 480 |
| ttg gca gct gct ttg aac gct gat gtg tgt gag att tac tcg gac gtt<br>Leu Ala Ala Ala Leu Asn Ala Asp Val Cys Glu Ile Tyr Ser Asp Val<br>165 170 175 | | 528 |
| gac ggt gtg tat acc gct gac ccg cgc atc gtt cct aat gca cag aag<br>Asp Gly Val Tyr Thr Ala Asp Pro Arg Ile Val Pro Asn Ala Gln Lys<br>180 185 190 | | 576 |
| ctg gaa aag ctc agc ttc gaa gaa atg ctg gaa ctt gct gct gtt ggc<br>Leu Glu Lys Leu Ser Phe Glu Glu Met Leu Glu Leu Ala Ala Val Gly<br>195 200 205 | | 624 |
| tcc aag att ttg gtg ctg cgc agt gtt gaa tac gct cgt gca ttc aat<br>Ser Lys Ile Leu Val Leu Arg Ser Val Glu Tyr Ala Arg Ala Phe Asn<br>210 215 220 | | 672 |
| gtg cca ctt cgc gta cgc tcg tct tat agt aat gat ccc ggc act ttg<br>Val Pro Leu Arg Val Arg Ser Ser Tyr Ser Asn Asp Pro Gly Thr Leu<br>225 230 235 240 | | 720 |
| att gcc ggc tct atg gag gat att ccc gtg gaa gaa gca gtc ctt acc<br>Ile Ala Gly Ser Met Glu Asp Ile Pro Val Glu Glu Ala Val Leu Thr<br>245 250 255 | | 768 |
| ggt gtc gca acc gac aag tcc gaa gcc aaa gta acc gtt ctg ggt att<br>Gly Val Ala Thr Asp Lys Ser Glu Ala Lys Val Thr Val Leu Gly Ile<br>260 265 270 | | 816 |
| tcc gat aag cca ggc gag act gcg aag gtt ttc cgt gcg ttg gct gat<br>Ser Asp Lys Pro Gly Glu Thr Ala Lys Val Phe Arg Ala Leu Ala Asp<br>275 280 285 | | 864 |
| gca gaa atc aac att gac atg gtt ctg cag aac gtc tct tct gta gaa<br>Ala Glu Ile Asn Ile Asp Met Val Leu Gln Asn Val Ser Ser Val Glu<br>290 295 300 | | 912 |
| gac ggc acc acc gac atc acc ttc acc tgc cct cgt tcc gac ggc cgc<br>Asp Gly Thr Thr Asp Ile Thr Phe Thr Cys Pro Arg Ser Asp Gly Arg<br>305 310 315 320 | | 960 |
| cgc gcg atg gag atc ttg aag aag ctt cag gtt cag ggc aac tgg acc<br>Arg Ala Met Glu Ile Leu Lys Lys Leu Gln Val Gln Gly Asn Trp Thr<br>325 330 335 | | 1008 |
| aat gtg ctt tac gac gac cag gtc ggc aaa gtc tcc ctc gtg ggt gct<br>Asn Val Leu Tyr Asp Asp Gln Val Gly Lys Val Ser Leu Val Gly Ala<br>340 345 350 | | 1056 |
| ggc atg aag tct cac cca ggt gtt acc gca gag ttc atg gaa gct ctg<br>Gly Met Lys Ser His Pro Gly Val Thr Ala Glu Phe Met Glu Ala Leu<br>355 360 365 | | 1104 |
| cgc gat gtc aac gtg aac atc gaa ttg att tcc acc tct gag att cgt<br>Arg Asp Val Asn Val Asn Ile Glu Leu Ile Ser Thr Ser Glu Ile Arg<br>370 375 380 | | 1152 |
| att tcc gtg ctg atc cgt gaa gat gat ctg gat gct gct gca cgt gca<br>Ile Ser Val Leu Ile Arg Glu Asp Asp Leu Asp Ala Ala Ala Arg Ala<br>385 390 395 400 | | 1200 |
| ttg cat gag cag ttc cag ctg ggc ggc gaa gac gaa gcc gtc gtt tat<br>Leu His Glu Gln Phe Gln Leu Gly Gly Glu Asp Glu Ala Val Val Tyr<br>405 410 415 | | 1248 |
| gca ggc acc gga cgc taa<br>Ala Gly Thr Gly Arg<br>420 | | 1266 |

<210> SEQ ID NO 42
<211> LENGTH: 421
<212> TYPE: PRT
<213> ORGANISM: Corynebacterium glutamicum

<400> SEQUENCE: 42

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Thr Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

```
Ile Ser Val Leu Ile Arg Glu Asp Leu Asp Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
            420

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
cgaccgcgtc tgagctgatc ctaccgatcg                                    30

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44
gccccgcctc ctccatgagg aagaagcggg                                    30

<210> SEQ ID NO 45
<211> LENGTH: 3423
<212> TYPE: DNA
<213> ORGANISM: Corynebacterium glutamicum
<220> FEATURE:
<221> NAME/KEY: CDS
<222> LOCATION: (1)..(3420)

<400> SEQUENCE: 45 gtg tcg act cac aca tct tca acg ctt cca gca ttc aaa aag atc ttg    48
Val Ser Thr His Thr Ser Ser Thr Leu Pro Ala Phe Lys Lys Ile Leu
1               5                   10                  15 gta gca aac cgc ggc gaa atc gcg gtc cgt gct ttc cgt gca gca ctc    96
Val Ala Asn Arg Gly Glu Ile Ala Val Arg Ala Phe Arg Ala Ala Leu
            20                  25                  30 gaa acc ggt gca gcc acg gta gct att tac ccc cgt gaa gat cgg gga   144
Glu Thr Gly Ala Ala Thr Val Ala Ile Tyr Pro Arg Glu Asp Arg Gly
        35                  40                  45 tca ttc cac cgc tct ttt gct tct gaa gct gtc cgc att ggt acc gaa   192
Ser Phe His Arg Ser Phe Ala Ser Glu Ala Val Arg Ile Gly Thr Glu
    50                  55                  60 ggc tca cca gtc aag gcg tac ctg gac atc gat gaa att atc ggt gca   240
Gly Ser Pro Val Lys Ala Tyr Leu Asp Ile Asp Glu Ile Ile Gly Ala
65                  70                  75                  80 gct aaa aaa gtt aaa gca gat gcc att tac ccg gga tac ggc ttc ctg   288
Ala Lys Lys Val Lys Ala Asp Ala Ile Tyr Pro Gly Tyr Gly Phe Leu
                85                  90                  95 tct gaa aat gcc cag ctt gcc cgc gag tgt gcg gaa aac ggc att act   336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct   384
Phe Ile Gly Pro Thr Pro Glu Val Leu Asp Leu Thr Gly Asp Lys Ser
        115                 120                 125 cgc gcg gta acc gcc gcg aag aag gct ggt ctg cca gtt ttg gcg gaa   432
Arg Ala Val Thr Ala Ala Lys Lys Ala Gly Leu Pro Val Leu Ala Glu
    130                 135                 140
```

```
tcc acc ccg agc aaa aac atc gat gag atc gtt aaa agc gct gaa ggc    480
Ser Thr Pro Ser Lys Asn Ile Asp Glu Ile Val Lys Ser Ala Glu Gly
145                 150                 155                 160 cag act tac ccc atc ttt gtg aag gca gtt gcc ggt ggt gga cgc        528
Gln Thr Tyr Pro Ile Phe Val Lys Ala Val Ala Gly Gly Gly Arg
                165                 170                 175 ggt atg cgt ttt gtt gct tca cct gat gag ctt cgc aaa tta gca aca    576
Gly Met Arg Phe Val Ala Ser Pro Asp Glu Leu Arg Lys Leu Ala Thr
            180                 185                 190 gaa gca tct cgt gaa gct gaa gcg gct ttc ggc gat ggc gcg gta tat    624
Glu Ala Ser Arg Glu Ala Glu Ala Ala Phe Gly Asp Gly Ala Val Tyr
        195                 200                 205 gtc gaa cgt gct gtg att aac cct cag cat att gaa gtg cag atc ctt    672
Val Glu Arg Ala Val Ile Asn Pro Gln His Ile Glu Val Gln Ile Leu
    210                 215                 220 ggc gat cac act gga gaa gtt gta cac ctt tat gaa cgt gac tgc tca    720
Gly Asp His Thr Gly Glu Val Val His Leu Tyr Glu Arg Asp Cys Ser
225                 230                 235                 240 ctg cag cgt cgt cac caa aaa gtt gtc gaa att gcg cca gca cag cat    768
Leu Gln Arg Arg His Gln Lys Val Val Glu Ile Ala Pro Ala Gln His
                245                 250                 255 ttg gat cca gaa ctg cgt gat cgc att tgt gcg gat gca gta aag ttc    816
Leu Asp Pro Glu Leu Arg Asp Arg Ile Cys Ala Asp Ala Val Lys Phe
            260                 265                 270 tgc cgc tcc att ggt tac cag ggc gcg gga acc gtg gaa ttc ttg gtc    864
Cys Arg Ser Ile Gly Tyr Gln Gly Ala Gly Thr Val Glu Phe Leu Val
        275                 280                 285 gat gaa aag ggc aac cac gtc ttc atc gaa atg aac cca cgt atc cag    912
Asp Glu Lys Gly Asn His Val Phe Ile Glu Met Asn Pro Arg Ile Gln
    290                 295                 300 gtt gag cac acc gtg act gaa gaa gtc acc gag gtg gac ctg gtg aag    960
Val Glu His Thr Val Thr Glu Glu Val Thr Glu Val Asp Leu Val Lys
305                 310                 315                 320 gcg cag atg cgc ttg gct gct ggt gca acc ttg aag gaa ttg ggt ctg    1008
Ala Gln Met Arg Leu Ala Ala Gly Ala Thr Leu Lys Glu Leu Gly Leu
                325                 330                 335 acc caa gat aag atc aag acc cac ggt gca gca ctg cag tgc cgc atc    1056
Thr Gln Asp Lys Ile Lys Thr His Gly Ala Ala Leu Gln Cys Arg Ile
            340                 345                 350 acc acg gaa gat cca aac aac ggc ttc cgc cca gat acc gga act atc    1104
Thr Thr Glu Asp Pro Asn Asn Gly Phe Arg Pro Asp Thr Gly Thr Ile
        355                 360                 365 acc gcg tac cgc tca cca ggc gga gct ggc gtt cgt ctt gac ggt gca    1152
Thr Ala Tyr Arg Ser Pro Gly Gly Ala Gly Val Arg Leu Asp Gly Ala
    370                 375                 380 gct cag ctc ggt ggc gaa atc acc gca cac ttt gac tcc atg ctg gtg    1200
Ala Gln Leu Gly Gly Glu Ile Thr Ala His Phe Asp Ser Met Leu Val
385                 390                 395                 400 aaa atg acc tgc cgt ggt tcc gac ttt gaa act gct gtt gct cgt gca    1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att    1296
Gln Arg Ala Leu Ala Glu Phe Thr Val Ser Gly Val Ala Thr Asn Ile
            420                 425                 430 ggt ttc ttg cgt gcg ttg ctg cgg gaa gag gac ttc act tcc aag cgc    1344
Gly Phe Leu Arg Ala Leu Leu Arg Glu Glu Asp Phe Thr Ser Lys Arg
        435                 440                 445 atc gcc acc gga ttc att gcc gat cac ccg cac ctc ctt cag gct cca    1392
Ile Ala Thr Gly Phe Ile Ala Asp His Pro His Leu Leu Gln Ala Pro
    450                 455                 460
```

```
cct gct gat gat gag cag gga cgc atc ctg gat tac ttg gca gat gtc    1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gct cct    1488
Thr Val Asn Lys Pro His Gly Val Arg Pro Lys Asp Val Ala Ala Pro
                485                 490                 495 atc gat aag ctg cct aac atc aag gat ctg cca ctg cca cgc ggt tcc    1536
Ile Asp Lys Leu Pro Asn Ile Lys Asp Leu Pro Leu Pro Arg Gly Ser
            500                 505                 510 cgt gac cgc ctg aag cag ctt ggc cca gcc gcg ttt gct cgt gat ctc    1584
Arg Asp Arg Leu Lys Gln Leu Gly Pro Ala Ala Phe Ala Arg Asp Leu
        515                 520                 525 cgt gag cag gac gca ctg gca gtt act gat acc acc ttc cgc gat gca    1632
Arg Glu Gln Asp Ala Leu Ala Val Thr Asp Thr Thr Phe Arg Asp Ala
    530                 535                 540 cac cag tct ttg ctt gcg acc cga gtc cgc tca ttc gca ctg aag cct    1680
His Gln Ser Leu Leu Ala Thr Arg Val Arg Ser Phe Ala Leu Lys Pro
545                 550                 555                 560 gcg gca gag gcc gtc gca aag ctg act cct gag ctt ttg tcc gtg gag    1728
Ala Ala Glu Ala Val Ala Lys Leu Thr Pro Glu Leu Leu Ser Val Glu
                565                 570                 575 gcc tgg ggc ggc gcg acc tac gat gtg gcg atg cgt ttc ctc ttt gag    1776
Ala Trp Gly Gly Ala Thr Tyr Asp Val Ala Met Arg Phe Leu Phe Glu
            580                 585                 590 gat ccg tgg gac agg ctc gac gag ctg cgc gag gcg atg ccg aat gta    1824
Asp Pro Trp Asp Arg Leu Asp Glu Leu Arg Glu Ala Met Pro Asn Val
        595                 600                 605 aac att cag atg ctg ctt cgc ggc cgc aac acc gtg gga tac acc ccg    1872
Asn Ile Gln Met Leu Leu Arg Gly Arg Asn Thr Val Gly Tyr Thr Pro
    610                 615                 620 tac cca gac tcc gtc tgc cgc gcg ttt gtt aag gaa gct gcc agc tcc    1920
Tyr Pro Asp Ser Val Cys Arg Ala Phe Val Lys Glu Ala Ala Ser Ser
625                 630                 635                 640 ggc gtg gac atc ttc cgc atc ttc gac gcg ctt aac gac gtc tcc cag    1968
Gly Val Asp Ile Phe Arg Ile Phe Asp Ala Leu Asn Asp Val Ser Gln
                645                 650                 655 atg cgt cca gca atc gac gca gtc ctg gag acc aac acc gcg gta gcc    2016
Met Arg Pro Ala Ile Asp Ala Val Leu Glu Thr Asn Thr Ala Val Ala
            660                 665                 670 gag gtg gct atg gct tat tct ggt gat ctc tct gat cca aat gaa aag    2064
Glu Val Ala Met Ala Tyr Ser Gly Asp Leu Ser Asp Pro Asn Glu Lys
        675                 680                 685 ctc tac acc ctg gat tac tac cta aag atg gca gag gag atc gtc aag    2112
Leu Tyr Thr Leu Asp Tyr Tyr Leu Lys Met Ala Glu Glu Ile Val Lys
    690                 695                 700 tct ggc gct cac atc ttg gcc att aag gat atg gct ggt ctg ctt cgc    2160
Ser Gly Ala His Ile Leu Ala Ile Lys Asp Met Ala Gly Leu Leu Arg
705                 710                 715                 720 cca gct gcg gta acc aag ctg gtc acc gca ctg cgc cgt gaa ttc gat    2208
Pro Ala Ala Val Thr Lys Leu Val Thr Ala Leu Arg Arg Glu Phe Asp
                725                 730                 735 ctg cca gtg cac gtg cac acc cac gac act gcg ggt ggc cag ctg gca    2256
Leu Pro Val His Val His Thr His Asp Thr Ala Gly Gly Gln Leu Ala
            740                 745                 750 acc tac ttt gct gca gct caa gct ggt gca gat gct gtt gac ggt gct    2304
Thr Tyr Phe Ala Ala Ala Gln Ala Gly Ala Asp Ala Val Asp Gly Ala
        755                 760                 765 tcc gca cca ctg tct ggc acc acc tcc cag cca tcc ctg tct gcc att    2352
Ser Ala Pro Leu Ser Gly Thr Thr Ser Gln Pro Ser Leu Ser Ala Ile
    770                 775                 780
```

```
gtt gct gca ttc gcg cac acc cgt cgc gat acc ggt ttg agc ctc gag         2400
Val Ala Ala Phe Ala His Thr Arg Arg Asp Thr Gly Leu Ser Leu Glu
785             790                 795                 800 gct gtt tct gac ctc gag ccg tac tgg gaa gca gtg cgc gga ctg tac         2448
Ala Val Ser Asp Leu Glu Pro Tyr Trp Glu Ala Val Arg Gly Leu Tyr
                805                 810                 815 ctg cca ttt gag tct gga acc cca ggc cca acc ggt cgc gtc tac cgc         2496
Leu Pro Phe Glu Ser Gly Thr Pro Gly Pro Thr Gly Arg Val Tyr Arg
            820                 825                 830 cac gaa atc cca ggc gga cag ttg tcc aac ctg cgt gca cag gcc acc         2544
His Glu Ile Pro Gly Gly Gln Leu Ser Asn Leu Arg Ala Gln Ala Thr
835             835                 840                 845 gca ctg ggc ctt gcg gat cgt ttc gaa ctc atc gaa gac aac tac gca         2592
Ala Leu Gly Leu Ala Asp Arg Phe Glu Leu Ile Glu Asp Asn Tyr Ala
850                 855                 860 gcc gtt aat gag atg ctg gga cgc cca acc aag gtc acc cca tcc tcc         2640
Ala Val Asn Glu Met Leu Gly Arg Pro Thr Lys Val Thr Pro Ser Ser
865             870                 875                 880 aag gtt gtt ggc gac ctc gca ctc cac ctc gtt ggt gcg ggt gtg gat         2688
Lys Val Val Gly Asp Leu Ala Leu His Leu Val Gly Ala Gly Val Asp
                885                 890                 895 cca gca gac ttt gct gcc gat cca caa aag tac gac atc cca gac tct         2736
Pro Ala Asp Phe Ala Ala Asp Pro Gln Lys Tyr Asp Ile Pro Asp Ser
            900                 905                 910 gtc atc gcg ttc ctg cgc ggc gag ctt ggt aac cct cca ggt ggc tgg         2784
Val Ile Ala Phe Leu Arg Gly Glu Leu Gly Asn Pro Pro Gly Gly Trp
            915                 920                 925 cca gag cca ctg cgc acc cgc gca ctg gaa ggc cgc tcc gaa ggc aag         2832
Pro Glu Pro Leu Arg Thr Arg Ala Leu Glu Gly Arg Ser Glu Gly Lys
930                 935                 940 gca cct ctg acg gaa gtt cct gag gaa gag cag gcg cac ctc gac gct         2880
Ala Pro Leu Thr Glu Val Pro Glu Glu Glu Gln Ala His Leu Asp Ala
945             950                 955                 960 gat gat tcc aag gaa cgt cgc aat agc ctc aac cgc ctg ctg ttc ccg         2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc         2976
Lys Pro Thr Glu Glu Phe Leu Glu His Arg Arg Arg Phe Gly Asn Thr
            980                 985                 990 tct gcg ctg gat gat cgt gaa ttc ttc tac ggc ctg gtc gaa ggc cgc         3024
Ser Ala Leu Asp Asp Arg Glu Phe Phe Tyr Gly Leu Val Glu Gly Arg
            995                 1000                1005 gag act ttg atc cgc ctg cca gat gtg cgc acc cca ctg ctt gtt cgc         3072
Glu Thr Leu Ile Arg Leu Pro Asp Val Arg Thr Pro Leu Leu Val Arg
    1010                1015                1020 ctg gat gcg atc tct gag cca gac gat aag ggt atg cgc aat gtt gtg         3120
Leu Asp Ala Ile Ser Glu Pro Asp Asp Lys Gly Met Arg Asn Val Val
1025                1030                1035                1040 gcc aac gtc aac ggc cag atc cgc cca atg cgt gtg cgt gac cgc tcc         3168
Ala Asn Val Asn Gly Gln Ile Arg Pro Met Arg Val Arg Asp Arg Ser
                1045                1050                1055 gtt gag tct gtc acc gca acc gca gaa aag gca gat tcc tcc aac aag         3216
Val Glu Ser Val Thr Ala Thr Ala Glu Lys Ala Asp Ser Ser Asn Lys
            1060                1065                1070 ggc cat gtt gct gca cca ttc gct ggt gtt gtc acc gtg act gtt gct         3264
Gly His Val Ala Ala Pro Phe Ala Gly Val Val Thr Val Thr Val Ala
            1075                1080                1085 gaa ggt gat gag gtc aag gct gga gat gca gtc gca atc atc gag gct         3312
Glu Gly Asp Glu Val Lys Ala Gly Asp Ala Val Ala Ile Ile Glu Ala
            1090                1095                1100
```

```
atg aag atg gaa gca aca atc act gct tct gtt gac ggc aaa atc gat    3360
Met Lys Met Glu Ala Thr Ile Thr Ala Ser Val Asp Gly Lys Ile Asp
1105            1110                1115                1120 cgc gtt gtg gtt cct gct gca acg aag gtg gaa ggt ggc gac ttg atc    3408
Arg Val Val Val Pro Ala Ala Thr Lys Val Glu Gly Gly Asp Leu Ile
                1125                1130                1135 gtc gtc gtt tcc taa                                                3423
Val Val Val Ser
        1140

<210> SEQ ID NO 46
<211> LENGTH: 1140
<212> TYPE: PRT
<213> ORGANISM: Corynebacterium glutamicum

<400> SEQUENCE: 46

Val Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320
```

```
Ala Gln Met Arg Leu Ala Ala Gly Ala Thr Leu Lys Glu Leu Gly Leu
            325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
            450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
            530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
            610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
```

```
                    740                 745                 750
Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
        850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Pro Ala Ala Thr Lys Val Glu Gly Asp Leu Ile
                1125                1130                1135

Val Val Val Ser
            1140
```